(12) United States Patent
Clarke et al.

(10) Patent No.: US 12,036,109 B2
(45) Date of Patent: Jul. 16, 2024

(54) DEVICES TO SUPPORT AND POSITION AN INTRAOCULAR LENS WITHIN THE EYE AND METHODS OF USE

(71) Applicant: Long Bridge Medical, Inc., Brisbane, CA (US)

(72) Inventors: Matthew Clarke, Brisbane, CA (US); Ayman Naseri, Brisbane, CA (US)

(73) Assignee: Long Bridge Medical, Inc., South San Francisco, CA (US)

( * ) Notice: Subject to any disclaimer, the term of this patent is extended or adjusted under 35 U.S.C. 154(b) by 807 days.

(21) Appl. No.: 17/190,169

(22) Filed: Mar. 2, 2021

(65) Prior Publication Data

US 2021/0338417 A1    Nov. 4, 2021

Related U.S. Application Data

(63) Continuation of application No. 16/989,567, filed on Aug. 10, 2020, now Pat. No. 10,973,624, which is a
(Continued)

(51) Int. Cl.
*A61F 2/16*    (2006.01)
*A61F 2/14*    (2006.01)

(52) U.S. Cl.
CPC ............... *A61F 2/16* (2013.01); *A61F 2/14* (2013.01); *A61F 2/15* (2015.04);
(Continued)

(58) Field of Classification Search
CPC ...... A61F 2/14; A61F 2/15; A61F 2/16; A61F 2002/1681; A61F 2002/169; A61F 2002/16902; A61F 2002/169053
See application file for complete search history.

(56) References Cited

U.S. PATENT DOCUMENTS 3,673,616 A    7/1972    Fedorov et al.
3,866,249 A    2/1975    Flom
(Continued)

FOREIGN PATENT DOCUMENTS

CA    2928918 A1    3/2017
CN    2328346 Y     7/1999
(Continued)

OTHER PUBLICATIONS

Carlevale Lens (Carlo Carlevale) by Soleko, "Scleral Suturefree IOL—Product Description." Alyko Medical, www.alykomedical.com/en-GB/products/implants/scleral-sutureless-iol-34097888. Accessed Oct. 29, 2020. 1 page.
(Continued)

*Primary Examiner* — William H Matthews
(74) *Attorney, Agent, or Firm* — Mintz Levin Cohn Ferris Glovsky and Popeo, P.C.

(57) ABSTRACT

A device for supporting an intraocular lens in an eye. The device has a lens support structure having an inner perimeter surface defining, at least in part, a central opening. When implanted, light may pass through the central opening towards the retina. The device has at least three fixation arms, each having an origin portion coupled to the lens support structure and a terminal portion comprising an anchor for trans-scleral fixation of the device. Prior to implantation, at least one fixation arm is biased towards a folded configuration and has a bend between the origin portion and the terminal portion. The origin portion extends away from the lens support structure and the anchor of the terminal portion is positioned over or under at least one of a portion of the lens support structure and a portion of the central opening. Related tools, systems, and methods are provided.

30 Claims, 37 Drawing Sheets

Related U.S. Application Data continuation of application No. 16/988,519, filed on Aug. 7, 2020, now Pat. No. 11,759,309.

(60) Provisional application No. 63/053,450, filed on Jul. 17, 2020, provisional application No. 63/017,423, filed on Apr. 29, 2020.

(52) U.S. Cl.
CPC ............... *A61F 2002/1681* (2013.01); *A61F 2002/1689* (2013.01); *A61F 2002/169* (2015.04); *A61F 2002/16902* (2015.04); *A61F 2002/169053* (2015.04); *A61F 2230/0006* (2013.01)

(56) References Cited

U.S. PATENT DOCUMENTS

| | | |
|---|---|---|
| 3,922,728 A | 12/1975 | Krasnov |
| 3,925,825 A | 12/1975 | Richards et al. |
| 3,986,214 A | 10/1976 | Krasnov |
| 4,014,049 A | 3/1977 | Richards et al. |
| 4,073,014 A | 2/1978 | Poler |
| 4,110,848 A | 9/1978 | Jensen |
| 4,118,808 A | 10/1978 | Poler |
| 4,168,547 A | 9/1979 | Konstantinov et al. |
| 4,190,049 A | 2/1980 | Hager et al. |
| 4,215,440 A | 8/1980 | Worst |
| 4,242,762 A | 1/1981 | Tennant |
| 4,254,511 A | 3/1981 | Chase et al. |
| 4,262,370 A | 4/1981 | Hartstein |
| 4,298,996 A | 11/1981 | Barnet |
| 4,437,194 A | 3/1984 | Hahs |
| 4,576,607 A | 3/1986 | Kelman |
| 4,585,457 A | 4/1986 | Kalb |
| 4,617,023 A | 10/1986 | Peyman |
| 4,629,460 A | 12/1986 | Dyer |
| 4,718,905 A | 1/1988 | Freeman |
| 4,737,322 A | 4/1988 | Bruns et al. |
| 4,790,847 A | 12/1988 | Woods |
| 4,878,910 A | 11/1989 | Koziol et al. |
| 4,932,971 A | 6/1990 | Kelman |
| 5,026,396 A | 6/1991 | Darin |
| 5,152,787 A | 10/1992 | Hamblen |
| 5,222,981 A | 6/1993 | Werblin |
| 5,258,025 A | 11/1993 | Fedorov et al. |
| 5,275,624 A | 1/1994 | Hara et al. |
| 5,336,262 A | 8/1994 | Chu |
| 5,466,233 A | 11/1995 | Weiner et al. |
| 5,507,805 A | 4/1996 | Koeniger |
| 5,628,795 A | 5/1997 | Langerman |
| 5,628,798 A | 5/1997 | Eggleston et al. |
| 5,752,960 A | 5/1998 | Nallakrishnan |
| 5,776,191 A | 7/1998 | Mazzocco |
| 5,843,184 A | 12/1998 | Cionni |
| 6,113,633 A | 9/2000 | Portney |
| 6,136,026 A | 10/2000 | Israel |
| 6,152,959 A | 11/2000 | Portney |
| 6,228,115 B1 | 5/2001 | Hoffmann et al. |
| 6,261,321 B1 | 7/2001 | Kellan |
| 6,264,693 B1 | 7/2001 | Ross |
| 6,299,641 B1 | 10/2001 | Woods |
| 6,342,058 B1 | 1/2002 | Portney |
| 6,398,809 B1 | 6/2002 | Hoffmann et al. |
| 6,443,985 B1 | 9/2002 | Woods |
| 6,488,708 B2 | 12/2002 | Sarfarazi |
| 6,551,354 B1 | 4/2003 | Ghazizadeh et al. |
| 6,616,691 B1 | 9/2003 | Tran |
| 6,616,692 B1 | 9/2003 | Glick et al. |
| 6,660,036 B2 | 12/2003 | Cumming |
| 6,685,741 B2 | 2/2004 | Landreville et al. |
| 6,767,363 B1 | 7/2004 | Bandhauer et al. |
| 6,797,004 B1 | 9/2004 | Brady et al. |
| 6,881,225 B2 | 4/2005 | Okada |
| 6,921,415 B2 | 7/2005 | Callahan et al. |
| 6,972,033 B2 | 12/2005 | McNicholas |
| 7,125,422 B2 | 10/2006 | Woods et al. |
| 7,223,288 B2 | 5/2007 | Zhang et al. |
| 7,300,464 B2 | 11/2007 | Tran |
| 7,311,194 B2 | 12/2007 | Jin et al. |
| 7,354,451 B2 | 4/2008 | Koch |
| 7,416,561 B2 | 8/2008 | Worst et al. |
| 7,462,194 B1 | 12/2008 | Blake |
| 7,569,048 B2 | 8/2009 | Brown |
| 7,597,678 B2 | 10/2009 | Brown |
| 7,662,179 B2 | 2/2010 | Sarfarazi |
| 7,763,069 B2 | 7/2010 | Brady et al. |
| 7,794,498 B2 | 9/2010 | Pinchuk |
| 7,806,930 B2 | 10/2010 | Brown |
| 7,875,270 B2 | 1/2011 | Zhang |
| 7,931,686 B2 | 4/2011 | Vaudant et al. |
| 8,012,204 B2 | 9/2011 | Weinschenk, III et al. |
| 8,109,998 B2 | 2/2012 | Cumming |
| 8,128,693 B2 | 3/2012 | Tran et al. |
| 8,162,927 B2 | 4/2012 | Peyman |
| 8,216,305 B2 | 7/2012 | Salvati et al. |
| 8,273,123 B2 | 9/2012 | Ben Nun |
| 8,377,125 B2 | 2/2013 | Kellan |
| 8,551,164 B2 | 10/2013 | Willis et al. |
| 8,585,758 B2 | 11/2013 | Woods |
| 8,764,823 B2 | 7/2014 | Cumming |
| 8,821,166 B2 | 9/2014 | Akura et al. |
| 8,852,275 B2 | 10/2014 | Park |
| 8,888,845 B2 | 11/2014 | Vaquero et al. |
| 8,900,300 B1 | 12/2014 | Wortz |
| 8,920,495 B2 | 12/2014 | Mirlay |
| 8,932,351 B2 | 1/2015 | Dell |
| 8,945,215 B2 | 2/2015 | Basinger |
| 8,956,408 B2 | 2/2015 | Smiley et al. |
| 9,034,035 B2 | 5/2015 | Betser et al. |
| 9,039,762 B2 | 5/2015 | Hong et al. |
| 9,072,600 B2 | 7/2015 | Tran |
| 9,084,673 B2 | 7/2015 | Dell |
| 9,095,424 B2 | 8/2015 | Kahook et al. |
| 9,125,736 B2 | 9/2015 | Kahook et al. |
| 9,198,752 B2 | 12/2015 | Woods |
| 9,289,287 B2 | 3/2016 | Kahook et al. |
| 9,326,845 B2 | 5/2016 | Ichikawa et al. |
| 9,333,072 B2 | 5/2016 | Ichikawa |
| 9,358,103 B1 | 6/2016 | Wortz et al. |
| 9,364,316 B1 | 6/2016 | Kahook et al. |
| 9,364,318 B2 | 6/2016 | Beer |
| 9,387,069 B2 | 7/2016 | Kahook et al. |
| 9,398,949 B2 | 7/2016 | Werblin |
| 9,421,088 B1 | 8/2016 | Kahook et al. |
| 9,439,754 B2 | 9/2016 | Wortz |
| 9,445,891 B2 * | 9/2016 | Ichikawa ............... A61F 2/16 |
| 9,445,892 B2 | 9/2016 | Brown |
| 9,468,523 B2 | 10/2016 | Dell |
| 9,498,325 B2 | 11/2016 | Salvati et al. |
| 9,504,558 B2 | 11/2016 | Wortz et al. |
| 9,517,127 B2 | 12/2016 | Wortz et al. |
| 9,629,711 B2 | 4/2017 | Cumming |
| 9,681,945 B2 | 6/2017 | Shahinpoor et al. |
| 9,681,946 B2 | 6/2017 | Kahook et al. |
| 9,713,526 B2 | 7/2017 | Rombach |
| 9,744,027 B2 | 8/2017 | Jansen |
| 9,877,825 B2 | 1/2018 | Kahook et al. |
| 9,925,037 B2 | 3/2018 | Wortz et al. |
| 9,925,040 B2 | 3/2018 | Kahook et al. |
| 10,010,405 B2 | 7/2018 | Hayes |
| 10,080,648 B2 | 9/2018 | Kahook et al. |
| 10,085,886 B2 | 10/2018 | Schuele et al. |
| 10,201,415 B2 | 2/2019 | Aharoni et al. |
| 10,271,944 B2 | 4/2019 | Ichikawa et al. |
| 10,271,945 B2 | 4/2019 | Wortz et al. |
| 10,286,107 B2 | 5/2019 | Kahook et al. |
| 10,299,910 B2 | 5/2019 | Cady |
| 10,383,721 B2 | 8/2019 | Marcos Celestino et al. |
| 10,433,950 B2 | 10/2019 | Shadduck |
| 10,449,036 B2 | 10/2019 | Christie et al. |
| 10,470,873 B2 | 11/2019 | Ichikawa et al. |
| 10,524,900 B2 | 1/2020 | Beer |
| 10,548,713 B2 | 2/2020 | Aharoni |

(56) References Cited

U.S. PATENT DOCUMENTS

| | | |
|---|---|---|
| 10,575,943 B2 | 3/2020 | Ingram |
| 10,603,162 B2 | 3/2020 | Wortz et al. |
| 2002/0087210 A1 | 7/2002 | Stenger et al. |
| 2002/0103535 A1 | 8/2002 | Portney |
| 2002/0161433 A1 | 10/2002 | Baikoff et al. |
| 2003/0055499 A1 | 3/2003 | Nguyen et al. |
| 2003/0158560 A1 | 8/2003 | Portney |
| 2003/0158599 A1 | 8/2003 | Brady et al. |
| 2003/0220652 A1 | 11/2003 | Israel |
| 2004/0042073 A1 | 3/2004 | Pynson |
| 2004/0148022 A1 | 7/2004 | Eggleston |
| 2004/0236422 A1 | 11/2004 | Zhang et al. |
| 2004/0249455 A1 | 12/2004 | Tran |
| 2005/0021138 A1 | 1/2005 | Woods |
| 2005/0021140 A1 | 1/2005 | Liao |
| 2005/0085907 A1 | 4/2005 | Hanna |
| 2005/0177229 A1 | 8/2005 | Boxer Wachler |
| 2006/0047339 A1 | 3/2006 | Brown |
| 2006/0047340 A1 | 3/2006 | Brown |
| 2006/0235515 A1 | 10/2006 | Chassain |
| 2007/0027541 A1 | 2/2007 | Aharoni et al. |
| 2007/0032868 A1 | 2/2007 | Woods |
| 2007/0123982 A1 | 5/2007 | Yablonski et al. |
| 2007/0162115 A1 | 7/2007 | Hermeking |
| 2007/0260308 A1 | 11/2007 | Tran |
| 2008/0086208 A1 | 4/2008 | Nordan |
| 2008/0154364 A1 | 6/2008 | Richardson et al. |
| 2009/0171458 A1 | 7/2009 | Kellan et al. |
| 2009/0198247 A1 | 8/2009 | Ben Nun |
| 2009/0204209 A1 | 8/2009 | Tran |
| 2010/0030331 A1 | 2/2010 | Zhang et al. |
| 2010/0094415 A1 | 4/2010 | Bumbalough |
| 2010/0121444 A1 | 5/2010 | Ben Nun |
| 2010/0131059 A1 | 5/2010 | Callahan et al. |
| 2010/0152848 A1 | 6/2010 | Williamson et al. |
| 2010/0262234 A1 | 10/2010 | Tran et al. |
| 2011/0071628 A1 | 3/2011 | Gross et al. |
| 2011/0313521 A1 | 12/2011 | Angelopoulos |
| 2011/0313522 A1 | 12/2011 | Hayes |
| 2011/0313523 A1 | 12/2011 | Hayes |
| 2012/0290086 A1 | 11/2012 | Malyugin et al. |
| 2012/0303119 A1 | 11/2012 | Callahan et al. |
| 2012/0330415 A1 | 12/2012 | Callahan et al. |
| 2013/0116781 A1 | 5/2013 | Ben Nun |
| 2013/0190868 A1 | 7/2013 | Kahook et al. |
| 2014/0094908 A1 | 4/2014 | Zaldivar et al. |
| 2014/0121768 A1 | 5/2014 | Simpson |
| 2014/0371851 A1 | 12/2014 | Aharoni |
| 2014/0371852 A1* | 12/2014 | Aharoni ............... A61F 2/14 623/6.43 |
| 2015/0025627 A1 | 1/2015 | Christie et al. |
| 2015/0127102 A1 | 5/2015 | Wortz |
| 2015/0265398 A1 | 9/2015 | Hartkens et al. |
| 2015/0305857 A1 | 10/2015 | Ichikawa |
| 2015/0366656 A1 | 12/2015 | Wortz et al. |
| 2015/0366659 A1 | 12/2015 | Wortz et al. |
| 2016/0000558 A1 | 1/2016 | Honigsbaum |
| 2016/0128828 A1 | 5/2016 | Dalvi |
| 2016/0157995 A1 | 6/2016 | Beer |
| 2016/0256260 A1 | 9/2016 | Wortz et al. |
| 2016/0256262 A1 | 9/2016 | Wortz et al. |
| 2016/0256267 A1 | 9/2016 | Wortz et al. |
| 2016/0256315 A1 | 9/2016 | Wortz et al. |
| 2016/0331520 A1 | 11/2016 | Beer |
| 2016/0338825 A1 | 11/2016 | Wortz et al. |
| 2016/0361156 A1 | 12/2016 | Brown |
| 2017/0020662 A1 | 1/2017 | Shadduck |
| 2017/0049560 A1 | 2/2017 | Cherne |
| 2017/0258575 A1 | 9/2017 | Wortz et al. |
| 2017/0319332 A1 | 11/2017 | Kahook et al. |
| 2017/0348095 A1 | 12/2017 | Wortz et al. |
| 2018/0014928 A1 | 1/2018 | Kahook et al. |
| 2018/0110613 A1 | 4/2018 | Wortz et al. |
| 2018/0263757 A1 | 9/2018 | Wanders |
| 2018/0271642 A1 | 9/2018 | Wortz et al. |
| 2018/0338825 A1 | 11/2018 | Aharoni |
| 2019/0015197 A1 | 1/2019 | Wortz et al. |
| 2019/0076236 A1 | 3/2019 | Scharioth et al. |
| 2019/0076239 A1 | 3/2019 | Wortz et al. |
| 2019/0083235 A1 | 3/2019 | Wortz |
| 2019/0091009 A1 | 3/2019 | Collins et al. |
| 2019/0133754 A1 | 5/2019 | Dalvi |
| 2019/0151079 A1 | 5/2019 | Zaldivar |
| 2019/0223998 A1 | 7/2019 | de Juan, Jr. et al. |
| 2019/0254809 A1 | 8/2019 | Dworschak et al. |
| 2019/0269500 A1 | 9/2019 | de Juan, Jr. et al. |
| 2019/0343621 A1 | 11/2019 | Wortz et al. |
| 2019/0380828 A1 | 12/2019 | Wortz |
| 2020/0000575 A1 | 1/2020 | Kojima |
| 2020/0022840 A1 | 1/2020 | Kahook et al. |
| 2020/0323626 A1 | 10/2020 | Akinay et al. |
| 2021/0315687 A1* | 10/2021 | Brodie ............... A61F 2/16 |
| 2022/0000605 A1 | 1/2022 | Clarke et al. |

FOREIGN PATENT DOCUMENTS

| | | |
|---|---|---|
| CN | 101031257 A | 9/2007 |
| CN | 102090942 A | 6/2011 |
| CN | 102090946 A | 6/2011 |
| CN | 204698755 U | 10/2015 |
| DE | 20 2016 105 208 U1 | 11/2016 |
| DE | 10 2019 115 408 B3 | 9/2020 |
| EP | 0 106 488 A1 | 4/1984 |
| EP | 0 346 245 A1 | 12/1989 |
| EP | 0 089 335 B2 | 3/1993 |
| EP | 0 931 521 A1 | 7/1999 |
| EP | 1 138 282 A1 | 10/2001 |
| EP | 1 341 485 B1 | 11/2006 |
| EP | 3 061 420 A1 | 8/2016 |
| EP | 3 158 974 A1 | 4/2017 |
| EP | 2 117 465 B1 | 7/2017 |
| EP | 3 171 821 B1 | 3/2020 |
| EP | 3700466 A1 | 9/2020 |
| FR | 3 033 694 A1 | 9/2016 |
| GB | 124500 A | 4/1919 |
| IT | 102014902224032 A1 | 7/2015 |
| JP | 4892156 B2 | 3/2012 |
| JP | 2013123616 A | 6/2013 |
| JP | 5383782 B2 | 1/2014 |
| JP | 2014290772 A | 5/2014 |
| KR | 20030051903 A | 6/2003 |
| KR | 10-2011-0075018 A | 7/2011 |
| KR | 10-1555298 B1 | 9/2015 |
| RU | 86462 U1 | 9/2009 |
| RU | 2367380 C2 | 9/2009 |
| RU | 2440076 C1 | 1/2012 |
| WO | WO-99/56670 A1 | 11/1999 |
| WO | WO-00/30566 A1 | 6/2000 |
| WO | WO-2006/103674 A2 | 10/2006 |
| WO | WO-2007/005893 A2 | 1/2007 |
| WO | WO-2008/077795 A2 | 7/2008 |
| WO | WO-2008/108525 A1 | 9/2008 |
| WO | WO-2011/101310 A1 | 8/2011 |
| WO | WO-2013/112589 A1 | 8/2013 |
| WO | WO-2014/197170 A1 | 12/2014 |
| WO | WO-2015/026226 A1 | 2/2015 |
| WO | WO-2016/071755 A1 | 5/2016 |
| WO | WO-2016/159910 A1 | 10/2016 |
| WO | WO-2016/182520 A1 | 11/2016 |
| WO | WO-2017/212352 A1 | 12/2017 |
| WO | WO-2019/050925 A1 | 3/2019 |
| WO | WO-2019/094768 A1 | 5/2019 |
| WO | WO-2019/097099 A1 | 5/2019 |
| WO | WO-2019/106011 A1 | 6/2019 |
| WO | WO-2019/235912 A1 | 12/2019 |
| WO | WO-2020/086312 A1 | 4/2020 |
| WO | WO-2020/086631 A1 | 4/2020 |
| WO | WO-2020/086312 A8 | 7/2020 |

OTHER PUBLICATIONS

Carlevale, C., et al. (Nov. 15, 2018), "New IOL dedicated for scleral fixation," Ocular Surgery News. Web. Nov. 2, 2020. 4 pages.

(56) References Cited

OTHER PUBLICATIONS https://www.healio.com/news/ophthalmology/20181113/new-iol-dedicated-for-scleral-fixation?M_BT=3592487855654.

* cited by examiner

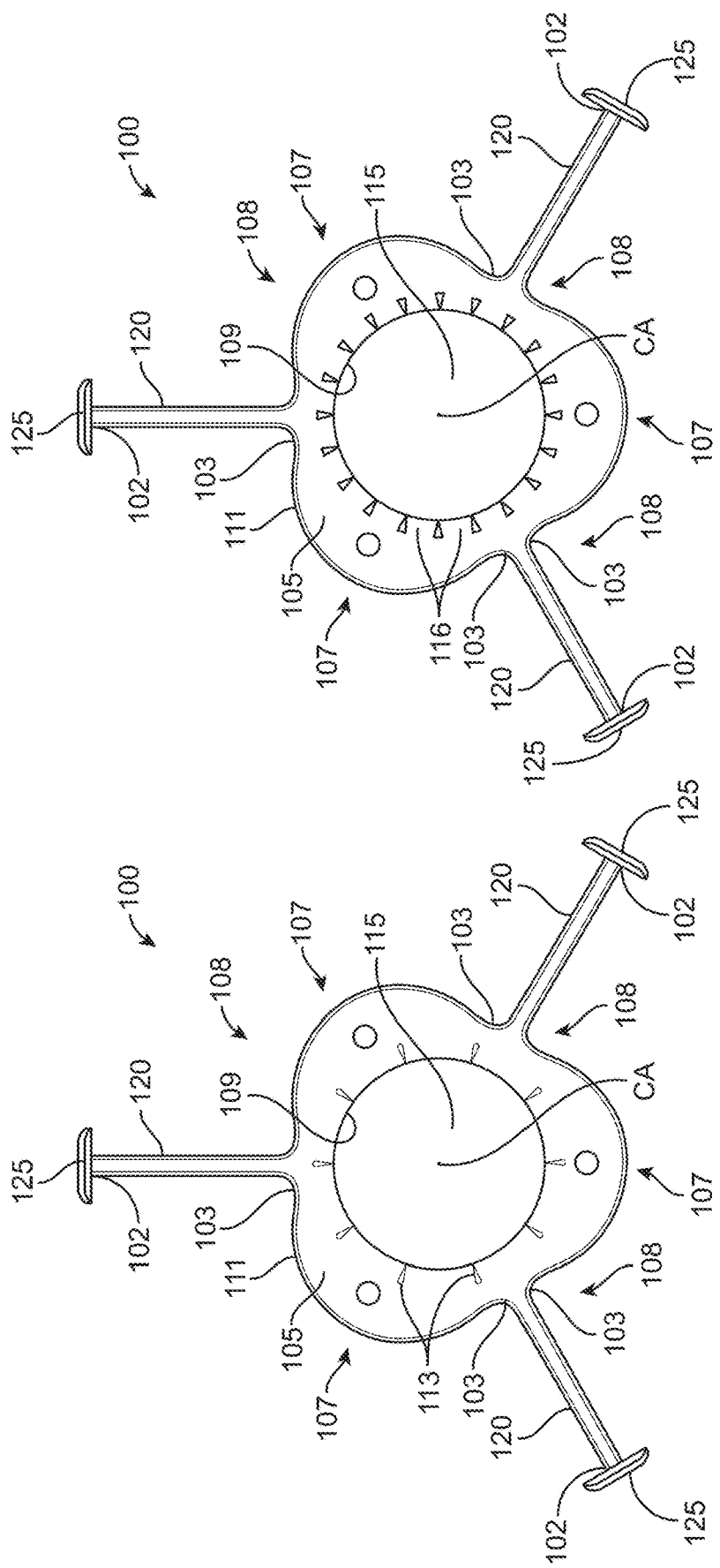

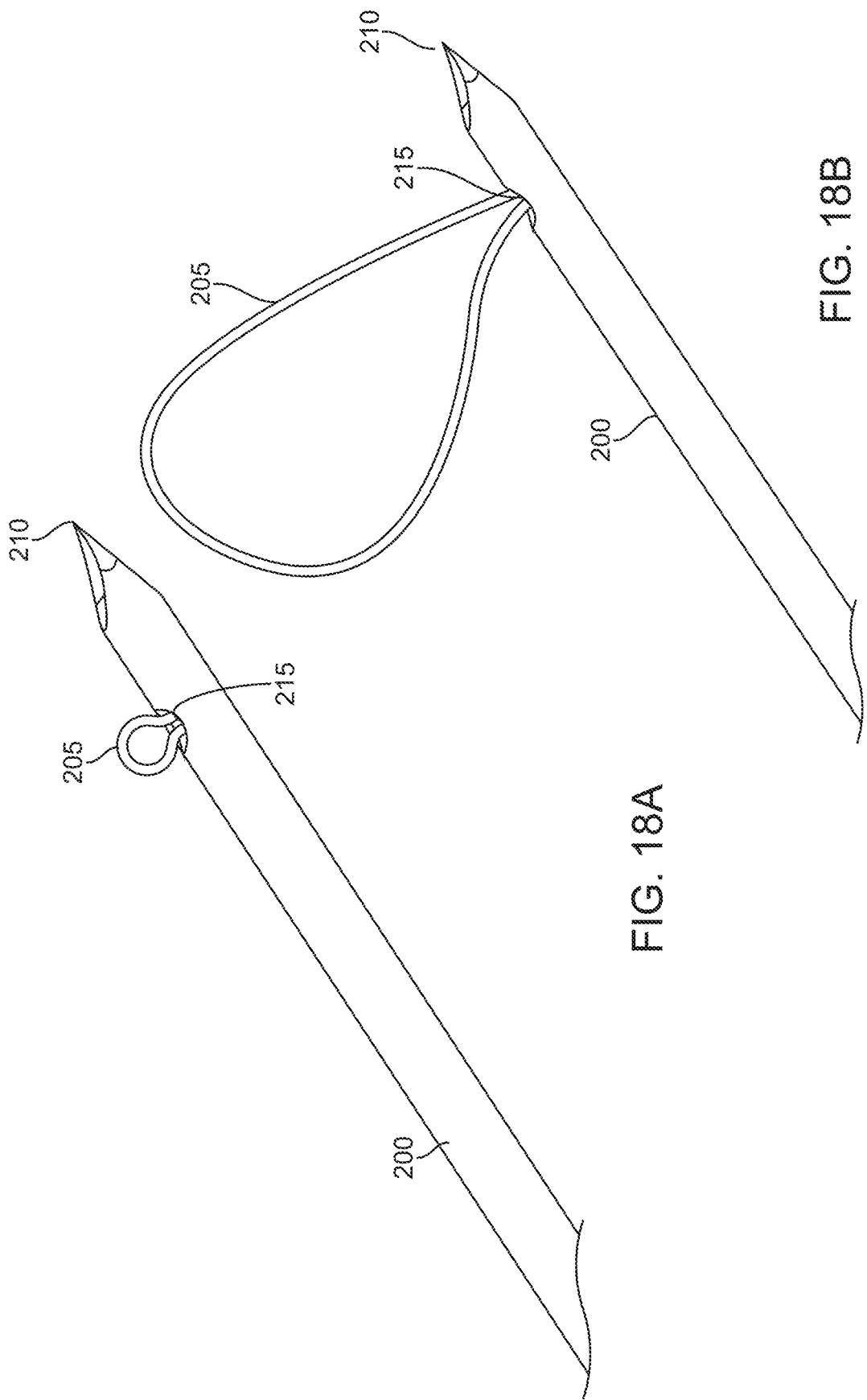

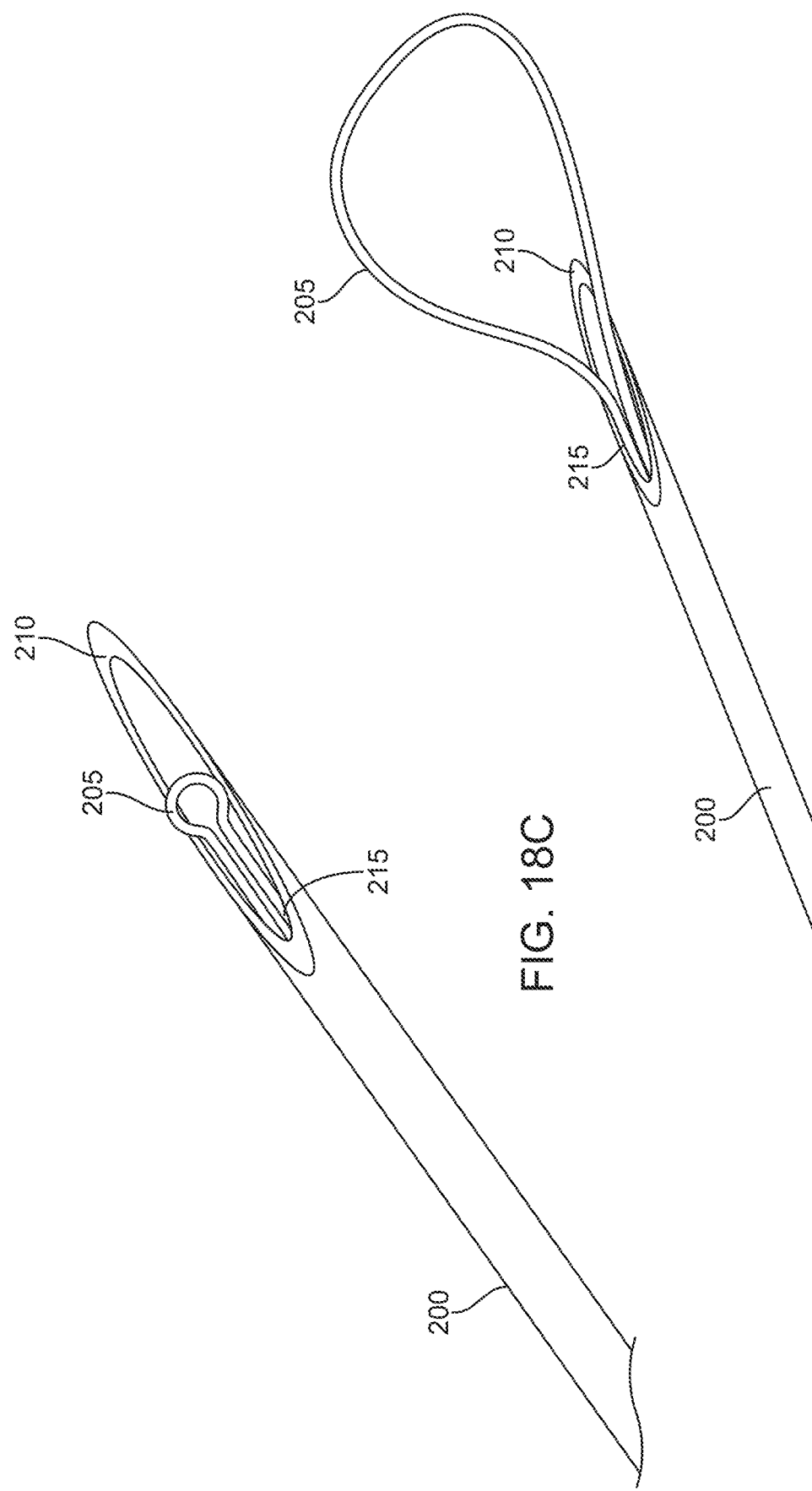

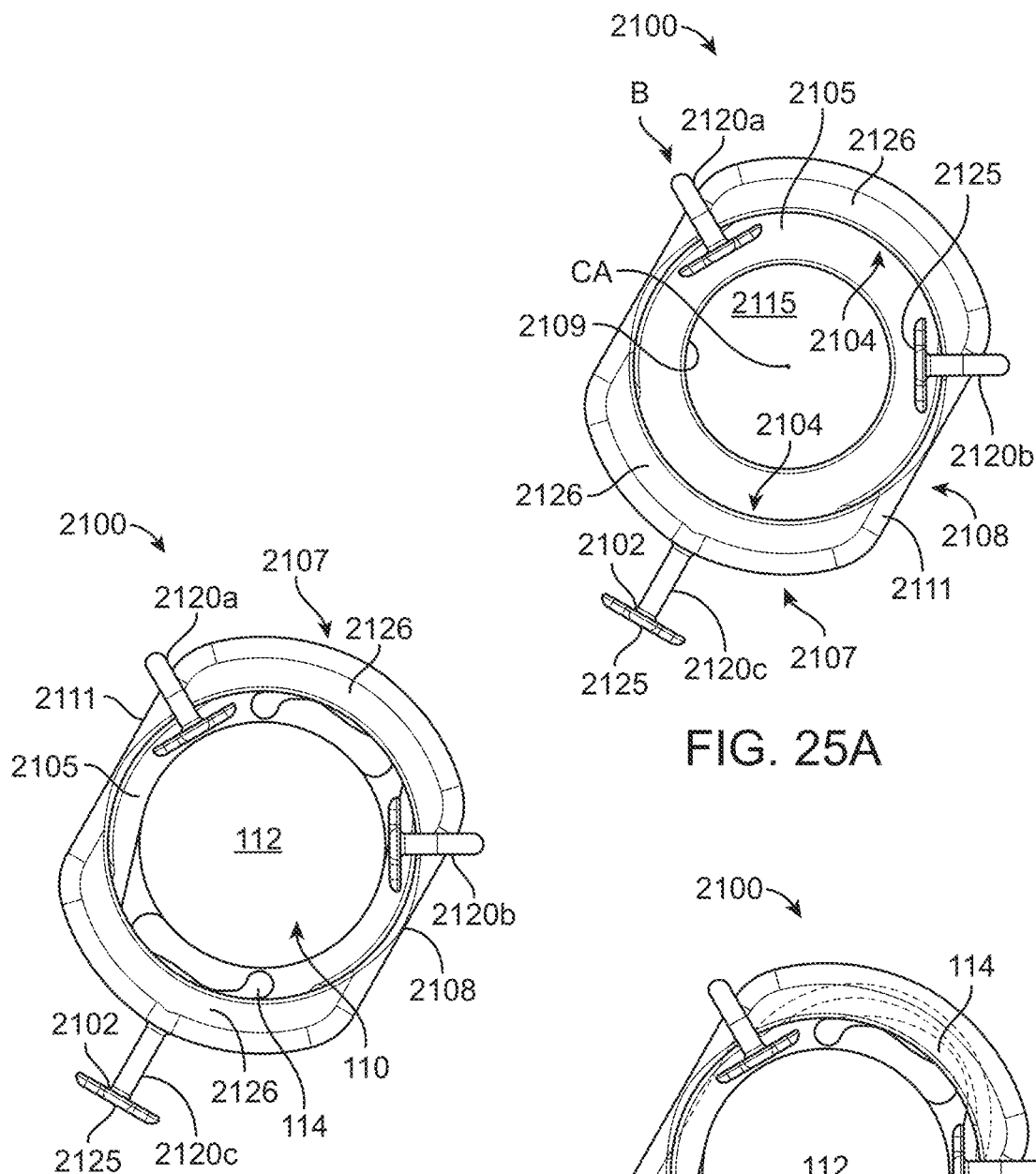
FIG. 25A
FIG. 25B
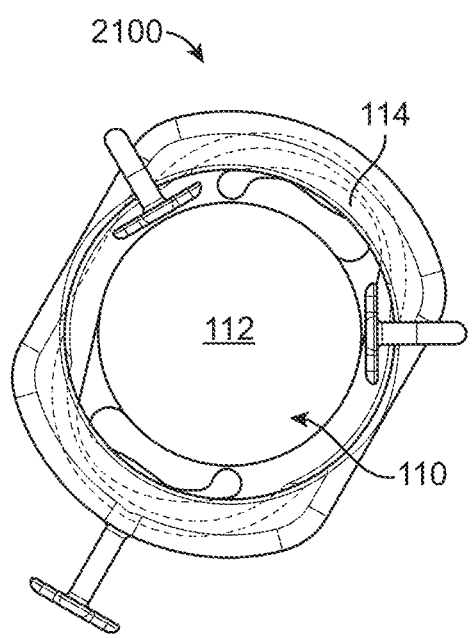
FIG. 25C

DEVICES TO SUPPORT AND POSITION AN INTRAOCULAR LENS WITHIN THE EYE AND METHODS OF USE

CROSS-REFERENCE TO RELATED APPLICATIONS

This application is a continuation of co-pending U.S. application Ser. No. 16/989,567, filed Aug. 10, 2020, which is a continuation of U.S. application Ser. No. 16/988,519, filed Aug. 7, 2020, entitled "Devices to Support and Position an Intraocular Lens within the Eye and Methods of Use," which claims the benefit of priority under 35 U.S.C. § 119(e) to U.S. Provisional Patent Application Ser. Nos. 63/017,423, filed Apr. 29, 2020, and 63/053,450, filed Jul. 17, 2020. The disclosures of the provisional applications are incorporated by reference in their entireties.

BACKGROUND

The present disclosure relates generally to the field of ophthalmics, more particularly to ophthalmic devices for supporting and positioning intraocular lenses in the eye.

Implantation of an intraocular lens (IOL) requires support within the eye to hold it in the correct position. Normally, this is achieved through the native capsular bag suspended by the zonules (fine thread like structures). However, these support structures can be compromised either due to intrinsic factors such as pseudoexfoliation, Marfan, or Weill-Marchesani syndromes, or extrinsic factors such as trauma. Additionally, lens support can be compromised iatrogenically either during the time of surgery (either anterior or posterior segment surgery) or as a late complication of previous surgery, for example by capsular phimosis.

The management of secondary IOL placement in the absence of sufficient capsular or zonular support continues to evolve. Currently the only FDA approved solution is placement of an anterior chamber IOL (ACIOL). The ACIOL is a larger lens with the ability to sit anterior to the iris, however over time these lenses can cause Uveitis-Glaucoma-Hyphema (UGH) syndrome as well as endothelial cell loss and corneal decompensation, and as a result are contraindicated in many patients. Modified capsule tension rings (Cionni or Ahmed) can be used off-label to provide sutured scleral support to a partially weakened capsule. However, in cases of substantial capsule or zonular compromise the lens must be secured without use of these native supporting structures. Other off-label techniques can be employed, such as iris suturing IOL, but this is technically difficult and can lead to iris pigment loss causing glaucoma. Lastly, scleral suturing IOLs with islets is technically complex, risks rotation, and the durability of the sutures is unknown; there are reported cases of breakage and lens subluxation. Additionally, all of these techniques force the surgeon to use an alternative lens type, instead of their preferred lens for the patient. Lastly, the decision of timing is critical, as frequently lens calculations are inadequate during the initial vitrectomy/lensectomy yet there is the desire to not subject the patient to additional posterior segment surgery, so non-ideal lenses are frequently implanted.

SUMMARY

In an aspect, described is an implantable device for supporting an intraocular lens in an eye including a support structure having an outer perimeter surface, an anterior-facing surface, a posterior-facing surface, and a single, central aperture extending through a full thickness of the support structure between the anterior-facing surface and the posterior-facing surface, the single aperture having a continuous inner circumference. The device includes a plurality of fixation arms coupled to the support structure and configured to be placed under tension to locate and stabilize the device within the eye. Each of the plurality of fixation arms have a terminal end coupled to a trans-scleral anchor for sutureless scleral fixation.

The trans-scleral anchors can be configured to be atraumatically externalized. The trans-scleral anchors can be positionable external to the sclera and internal to the conjunctiva. At least one of the plurality of fixation arms can be substantially non-planar. The plurality of fixation arms can include three fixation arms extending outward from the outer perimeter surface of the support structure. The at least a first fixation arm of the three fixation arms can be biased towards a center of the device. At least the first fixation arm and a second fixation arm of the three fixation arms can each be biased towards the center of the device. A third fixation arm of the three fixation arms can have increased cross-sectional area compared to a cross-sectional area of the first and second fixation arms. The increased cross-sectional area of the third fixation arm can increase its rigidity compared to a rigidity of either the first fixation arm or the second fixation arm. The three fixation arms can be uniformly distributed around the outer perimeter surface of the support structure.

The anterior-facing surface can form a stable platform upon which an intraocular lens is placed during use. The continuous inner circumference can form a uniform, substantially circular shape and the outer perimeter surface can form a substantially non-circular shape. When in use, the support structure can provide centration of the device without 360 degree contact with the ciliary body along the substantially non-circular shaped outer perimeter surface. When in use, the substantially non-circular shaped outer perimeter surface of the support structure can avoid contact with the ciliary body or can contact the ciliary body along less than 120 degrees. When in use, the substantially non-circular shaped outer perimeter surface of the support structure can contact the ciliary processes at three distinct points. The outer perimeter surface of the support structure can include a plurality of lobes projecting outward from a plurality of substantially flat or concave sides. The plurality of lobes can include three convex lobes providing the support structure with a substantially rounded triangle shape. The three convex lobes can provide anti-rotation function in a Z-plane. When in use, the three convex lobes can provide non-penetrating contact with the ciliary body.

The support structure can include one or more slits formed in an inner wall defining the central aperture. The support structure can have a thickness from the anterior-facing surface to the posterior-facing surface that tapers towards the central aperture. At least one of the plurality of fixation arms can include a plurality of anchors along its length including the trans-scleral anchor at the terminal end. When in use, the trans-scleral anchor can be configured to be positioned external to the sclera. The trans-scleral anchor can have a geometry configured to be passed through the sclera in a first direction during insertion and configured to resist pulling through the sclera in a second, opposite direction. When in a resting state, at least one of the plurality of fixation arms can incorporate a bend between its origin with the support structure and its terminal end coupled to the trans-scleral anchor forming a bent fixation arm. The bend can be between 90 degrees and 270 degrees from the origin in a radial and centripetal direction. The bend can be 180 degrees from the origin with the support structure. When in a resting state, the terminal end of the bent fixation arm can lie in a plane different than a plane of the support structure, and the trans-scleral anchor can be positioned over at least a portion of the support structure. The bent fixation arm can incorporate an elastic material or deformable hinge to facilitate unbending of the bent fixation arm so that the terminal end approaches the plane of the support structure. Two fixation arms can be flexible and have inward bias and a third fixation arm can be less flexible than the two fixation arms. The trans-scleral anchor of each of the plurality of fixation arms can be configured to be positioned external to the sclera. The trans-scleral anchor can include a central portion and one or more peripheral graspable portions. The central portion can be arranged to lie over a wound through which the anchor is externalized upon implantation. The central portion can have increased thickness, height, and/or width compared to the graspable portions. One of the plurality of fixation arms can be mechanically reinforced. The mechanical reinforcement can bias the device anteriorly upon implantation.

In an interrelated aspect, provided is a method of implanting an anterior capsule device having artificial zonular fixation providing a stable platform for placement of an intraocular lens within an artificially constructed sulcus.

In an interrelated aspect, provided is an implantable device for supporting an intraocular lens in an eye having a support structure that lies substantially in a first plane. The support structure has an outer perimeter surface, an anterior-facing surface, a posterior-facing surface, and a single, central aperture extending through a full thickness of the support structure between the anterior-facing surface and the posterior-facing surface. The single aperture has a continuous inner circumference. The device has three fixation arms coupled to the support structure that are configured to locate and stabilize the device within the eye. Each of the three fixation arms has a terminal end coupled to a trans-scleral anchor for sutureless scleral fixation. When in a resting state, at least a first of the three fixation arms incorporates a bend between its origin with the support structure and its terminal end forming a first bent arm. The terminal end of the first bent arm lies in a second plane that is different than the first plane.

The trans-scleral anchor of the first bent arm can be positioned over at least a portion of the support structure. The trans-scleral anchor of the bent arm can be positioned over at least a portion of the central aperture. At least a second of the three fixation arms can incorporate a bend between its origin with the support structure and its terminal end forming a second bent arm. The terminal end of the second bent arm can lie in a second plane that is different than the first plane. The trans-scleral anchor of the second bent arm can be positioned over at least a portion of the support structure. The trans-scleral anchor of the second bent arm can be positioned over at least a portion of the central aperture. A third of the three fixation arms can be straight between its origin with the support structure and its terminal end forming a straight fixation arm. The straight fixation arm can be less flexible than the first and second bent arms. The first and second bent arms can be biased toward a central axis of the device.

In an interrelated aspect, provided is an implantable device for supporting an intraocular lens in an eye having a support structure that lies substantially in a first plane. The support structure includes an outer perimeter surface, an anterior-facing surface, a posterior-facing surface, and a single, central aperture extending through a full thickness of the support structure between the anterior-facing surface and the posterior-facing surface. The single aperture has an inner perimeter surface having a circumference. The device includes three fixation arms coupled to the support structure and configured to be placed under tension to locate and stabilize the device within the eye. Each of the three fixation arms has a terminal end coupled to a trans-scleral anchor for sutureless scleral fixation. The inner perimeter surface forms a uniform, substantially circular shape and the outer perimeter surface forms a substantially non-circular shape.

The non-circular shape of the outer perimeter surface can include a plurality of lobes projecting outward from a plurality of sides. The plurality of sides can be substantially flat or concave. Each of the three fixation arms can extend outward from a respective one of the plurality of sides. The support structure can have a width between the outer perimeter surface and the inner perimeter surface that varies around the circumference. Each of the three fixation arms can have a length that is longer than a distance the plurality of lobes project outward. The anterior-facing surface and the posterior-facing surface of the support structure can taper towards a central axis of the device. The inner perimeter surface and the outer perimeter surface can be convex such that the inner perimeter surface projects towards a central axis of the device and the outer perimeter surface projects away from the central axis of the device. A thickness of the support structure from the anterior-facing surface to the posterior-facing surface can be about 0.15 mm to about 1.5 mm. The support structure can be substantially flat. The support structure can incorporate a recess in the anterior-facing surface. The support structure can incorporate one or more posts projecting upward from the anterior-facing surface.

In an interrelated aspect, provided is a device for implantation into a posterior chamber of an eye lacking an intact capsular bag. The device includes a support structure having a central opening. The support structure is adapted to provide support for an artificial intraocular lens. After implantation into the eye, the device and the artificial intraocular lens are adapted to permit passage of light through both the opening and the artificial intraocular lens. The device includes at least three fixation arms extending substantially orthogonally from the support structure. Prior to implantation, one of the at least three fixation arms extends in an unfolded configuration from the support structure, and at least two of the at least three fixation arms extend in a folded configuration from the support structure. One of the at least three fixation arms is biased towards the unfolded configuration and at least two of the at least three fixation arms are biased toward the folded configuration prior to implantation. Upon implantation, each of the at least two of the at least three fixation arms are unfolded. Each of the at least three fixation arms includes an atraumatic distal anchor portion for sutureless, trans-scleral fixation of the device within the posterior chamber.

In an interrelated aspect, provided is a device for implantation into a posterior chamber of an eye lacking an intact capsular bag including a support structure having a central aperture extending through a full thickness of the support structure. The device includes a plurality of fixation arms, each of the plurality of fixation arms having an origin portion at the support structure and a terminal end portion coupled to an atraumatic anchor for sutureless, trans-scleral fixation. Prior to trans-scleral fixation of the anchors, the plurality of fixation arms can include a curved fixation arm that is curved between its origin portion and its terminal end enabling visualization of at least a portion of the curved fixation arm through the pupil of the eye.

After trans-scleral fixation of the anchors, each of the plurality of fixation arms can be tensioned between the origin portion and the terminal end to align the support structure relative to a Z-plane of the eye. The support structure can be adapted to provide support for an intraocular lens and the central aperture can be adapted to permit passage of light through both the central aperture and the intraocular lens supported by the support structure. The curved fixation arm can curve anteriorly and its atraumatic anchor can be positioned over at least a portion of the support structure. The curved fixation arm can curve posteriorly and its atraumatic anchor can be positioned under at least a portion of the support structure.

In an interrelated aspect, provided is a method of implanting a device into a posterior chamber of an eye lacking an intact capsular bag. The method includes inserting the device into the posterior chamber. The device includes a lens support structure having a central opening and at least three fixation arms. Each of the at least three fixation arms has an origin portion coupled to the lens support structure and a terminal portion comprising an anchor. Prior to insertion into the posterior chamber, at least one of the at least three fixation arms is biased towards a linear configuration and at least a second of the at least three fixation arms is biased towards a folded configuration. The folded configuration includes the origin portion extending away from the lens support structure, a central portion comprising a bend, fold or curve, and the anchor of the terminal portion positioned over or under at least one of a portion of the lens support structure and a portion of the central opening. The method includes grasping the anchor of the at least one of the at least three fixation arms and externalizing the anchor through and over a first portion of sclera. The method includes grasping the anchor of the second fixation arm, unfolding the folded configuration of the second fixation arm and externalizing the anchor of the second fixation arm through and over a second portion of sclera. The method includes grasping the anchor of a third of the at least three fixation arms, tensioning the third fixation arm and externalizing the anchor of the third fixation arm through and over a third portion of sclera to locate and stabilize the device within the posterior chamber of the eye.

In an interrelated aspect, provided is a device for supporting an artificial intraocular lens in an eye. The device includes a lens support structure having a central opening. When the device is implanted in the eye, light may pass through the central opening towards a retina. The device includes at least three fixation arms, each of the at least three fixation arms has an origin portion coupled to and extending outward from the lens support structure and a terminal portion having an anchor for trans-scleral fixation of the device within the eye. Prior to implantation, at least one fixation arm of the at least three fixation arms is biased towards a folded configuration incorporating a bend between the origin portion and the terminal portion that positions the anchor of the terminal portion overlapping at least a portion of the lens support structure.

The anchor of the at least one fixation arm in the folded configuration, when positioned in the eye and before scleral fixation, can be positioned over the at least a portion of the lens support structure and anterior to the lens support structure relative to the retina. The anchor positioned over the at least a portion of the lens support structure can be over and anterior to the central opening of the lens support structure relative to the retina. At least a first portion of the anchor can be over and anterior to the central opening and at least a second portion of the anchor can be over and anterior to the lens support structure relative to the retina. The anchor of the at least one fixation arm in the folded configuration, when positioned in the eye and before scleral fixation, can be positioned under the at least a portion of the lens support structure and posterior to the lens support structure relative to the retina. The anchor positioned under the at least a portion of the lens support structure can be under and posterior to the central opening of the lens support structure relative to the retina. At least a first portion of the anchor can be under and posterior to the central opening and at least a second portion of the anchor can be under and posterior to the lens support structure relative to the retina. The folded configuration can include the terminal portion folded over or under the origin portion of the at least one fixation arm. The terminal portion of the at least one fixation arm in the folded configuration can overlap the origin portion. The anchor of the terminal portion of the at least one fixation arm in the folded configuration can be visible through a pupil of the eye upon placement of the device into a posterior chamber of the eye but prior to trans-scleral fixation of the anchor. The anchor of the at least one fixation arm in the folded configuration can be positioned within a distance from a central axis of the device, the central axis extending anterior-to-posterior through the central opening. The distance can be no greater than about 4.0 mm. The at least one fixation arm in the folded configuration can curve such that the anchor of the terminal portion of the at least one fixation arm projects back towards the central opening of the device. The anchor can be adapted for sutureless, trans-scleral fixation. The lens support structure can be generally ring-shaped.

The lens support structure can further have an outer perimeter and an inner perimeter. The central opening can be bounded by the inner perimeter. The outer perimeter of the lens support structure can be substantially non-circular and the inner perimeter can be substantially circular. The lens support structure can include an outer perimeter. The outer perimeter can include a plurality of lobes projecting radially away from the central opening. A first numerical count of the plurality of lobes can be equal to a second numerical count of the at least three fixation arms. Each of the lobes can be spaced between adjacent fixation arms. Each of the lobes can be symmetrically spaced around the outer perimeter of the lens support structure between adjacent fixation arms. Each of the at least three fixation arms can be symmetrically spaced around the outer perimeter of the lens support structure between adjacent lobes. The plurality of lobes can consist of three lobes. The at least three fixation arms can consist of three fixation arms. The plurality of lobes can include at least three convex lobes providing the lens support structure with a substantially rounded triangular shape. When implanted, the at least three convex lobes can provide non-penetrating contact with ciliary tissue in the eye. At least two fixation arms of the at least three fixation arms can be biased towards the folded configuration prior to implantation. All fixation arms of the at least three fixation arms can be biased towards the folded configuration prior to implantation. At least a second fixation arm of the at least three fixation arms can be biased towards an unfolded configuration prior to implantation. The at least a second fixation arm can have a larger cross-sectional area compared to a cross-sectional area of the at least one fixation arm of the at least three fixation arms to provide an increased rigidity of the at least a second fixation arm relative to a rigidity of the at least one fixation arm of the at least three fixation arms. The lens support structure can form a substantially planar surface. The lens support structure can include a geometry adapted to mate with a perimeter of an intraocular lens or with one or more haptics of the intraocular lens. The geometry can be a concavity, recess, channel, or groove forming at least a portion of an inner perimeter of the lens support structure. The at least one fixation arm of the at least three fixation arms can include a deformable material to facilitate unbending of the fixation arm from the folded configuration to an unfolded configuration in order to facilitate the trans-scleral fixation. After trans-scleral fixation of the anchor, the at least one fixation arm can be tensioned between the origin portion and the terminal end into the unfolded configuration and to align the lens support structure relative to a Z-plane of the eye.

The device can include three fixation arms. Two of the three fixation arms can be flexible and be biased towards the folded configuration. A third fixation arm can be less flexible than the two of the three flexible fixation arms and can be biased towards an unfolded configuration. All three fixation arms can be configured to be placed under tension. The folded configuration of each of the two of the three fixation arms can bias the terminal portion toward a central axis of the device. The lens support structure can be biased towards a substantially flat or planar configuration while the at least one fixation arm of the at least three fixation arms is biased towards the folded configuration.

In an interrelated aspect, provided is a device for supporting an artificial intraocular lens in an eye. The device includes a lens support structure having an inner perimeter surface defining, at least in part, a central opening. When the device is implanted in the eye, light may pass through the central opening towards the retina. The device includes at least three fixation arms. Each of the at least three fixation arms has an origin portion coupled to the lens support structure and a terminal portion having an anchor for trans-scleral fixation of the device within the eye. Prior to implantation, at least one fixation arm of the at least three fixation arms is biased towards a folded configuration. The folded configuration includes the origin portion extending away from the lens support structure and the anchor of the terminal portion positioned over or under at least one of a portion of the lens support structure and a portion of the central opening, and a bend between the origin portion and the terminal portion.

The anchor of the at least one fixation arm in the folded configuration, when positioned in the eye and before scleral fixation, can be positioned over and anterior to the portion of the lens support structure relative to the retina. The anchor of the at least one fixation arm in the folded configuration, when positioned in the eye and before scleral fixation, can be positioned over and anterior to the portion of the central opening relative to the retina. At least a first portion of the anchor can be over and anterior to the portion of the central opening and at least a second portion of the anchor can be over and anterior to the portion of the lens support structure relative to the retina. The anchor of the at least one fixation arm in the folded configuration, when positioned in the eye and before scleral fixation, can be positioned under and posterior to the portion of the lens support structure relative to the retina. The anchor of the at least one fixation arm in the folded configuration, when positioned in the eye and before scleral fixation, can be positioned under and posterior to the portion of the central opening relative to the retina. At least a first portion of the anchor can be under and posterior to the portion of the central opening and at least a second portion of the anchor can be under and posterior to the portion of the lens support structure relative to the retina. The folded configuration can include the terminal portion folded over or under the origin portion of the at least one fixation arm. The terminal portion of the at least one fixation arm in the folded configuration can overlap the origin portion. The anchor of the terminal portion of the at least one fixation arm in the folded configuration can be visible through a pupil of the eye upon placement of the device into a posterior chamber of the eye but prior to trans-scleral fixation of the anchor. The anchor of the at least one fixation arm in the folded configuration can be positioned within a distance from a central axis of the device, the central axis extending anterior-to-posterior through the central opening. The distance can be no greater than about 4.0 mm. The at least one fixation arm in the folded configuration can curve such that the anchor of the terminal portion of the at least one fixation arm projects back towards the central opening of the device. The anchor can be adapted for sutureless, trans-scleral fixation.

The lens support structure can be generally ring-shaped. The lens support structure can further include an outer perimeter and an inner perimeter. The outer perimeter can be substantially non-circular and the inner perimeter can be substantially circular. The lens support structure can further include an outer perimeter that includes a plurality of lobes projecting radially away from the central opening. A first numerical count of the plurality of lobes can equal a second numerical count of the at least three fixation arms. Each of the lobes can be spaced between adjacent fixation arms. Each of the lobes can be symmetrically spaced around the outer perimeter of the lens support structure between adjacent fixation arms. Each of the at least three fixation arms can be symmetrically spaced around the outer perimeter of the lens support structure between adjacent lobes. The plurality of lobes can consist of three lobes, and the at least three fixation arms can consist of three fixation arms. The plurality of lobes can include at least three convex lobes providing the lens support structure with a substantially rounded triangular shape. When implanted, the at least three convex lobes can provide non-penetrating contact with ciliary tissue in the eye.

At least two fixation arms of the at least three fixation arms can be biased towards the folded configuration prior to implantation. All fixation arms of the at least three fixation arms can be biased towards the folded configuration prior to implantation. At least a second fixation arm of the at least three fixation arms can be biased towards an unfolded configuration prior to implantation. The at least a second fixation arm can have a larger cross-sectional area compared to a cross-sectional area of the at least one fixation arm of the at least three fixation arms to provide an increased rigidity of the at least a second fixation arm relative to a rigidity of the at least one fixation arm of the at least three fixation arms.

The lens support structure can provide a substantially planar surface. The lens support structure can include a geometry adapted to mate with a perimeter of an intraocular lens or with one or more haptics of the intraocular lens. The geometry can include a concavity, recess, channel, or groove forming at least a portion of an inner perimeter of the lens support structure.

The at least one fixation arm of the at least three fixation arms can include a deformable material to facilitate unbending of the fixation arm from the folded configuration to an unfolded configuration in order to facilitate the trans-scleral fixation. After trans-scleral fixation of the anchor, the at least one fixation arm can be tensioned between the origin portion and the terminal end into the unfolded configuration and to align the lens support structure relative to a Z-plane of the eye. The device can include three fixation arms. Two of the three fixation arms can be flexible and can be biased towards the folded configuration. A third fixation arm can be less flexible than the two of the three flexible fixation arms and can be biased towards an unfolded configuration. All three fixation arms can be configured to be placed under tension. The folded configuration of each of the two of the three fixation arms can bias the terminal portion toward a central axis of the device. The lens support structure can be biased towards a substantially flat or planar configuration while the at least one fixation arm of the at least three fixation arms can be biased towards the folded configuration.

In some variations, one or more of the following can optionally be included in any feasible combination in the above methods, apparatus, devices, and systems. More details are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIG. 5 shows a top down view of the device of FIG. 1 with dotted lines indicating how the device can be slit in order to facilitate optic capture;

FIG. 6. shows a top down view of the device of FIG. 1 with flaps integrated into the lens support structure in order to facilitate optic capture;

FIGS. 18A-18B show additional implementations of a snare device used to manipulate and externalize the footplates;

FIGS. 18C-18D show additional implementations of a snare device used to manipulate and externalize the footplates;

FIGS. 25A-25C show another implementation of a device having awnings configured to accommodate an IOL;

Figure 1:
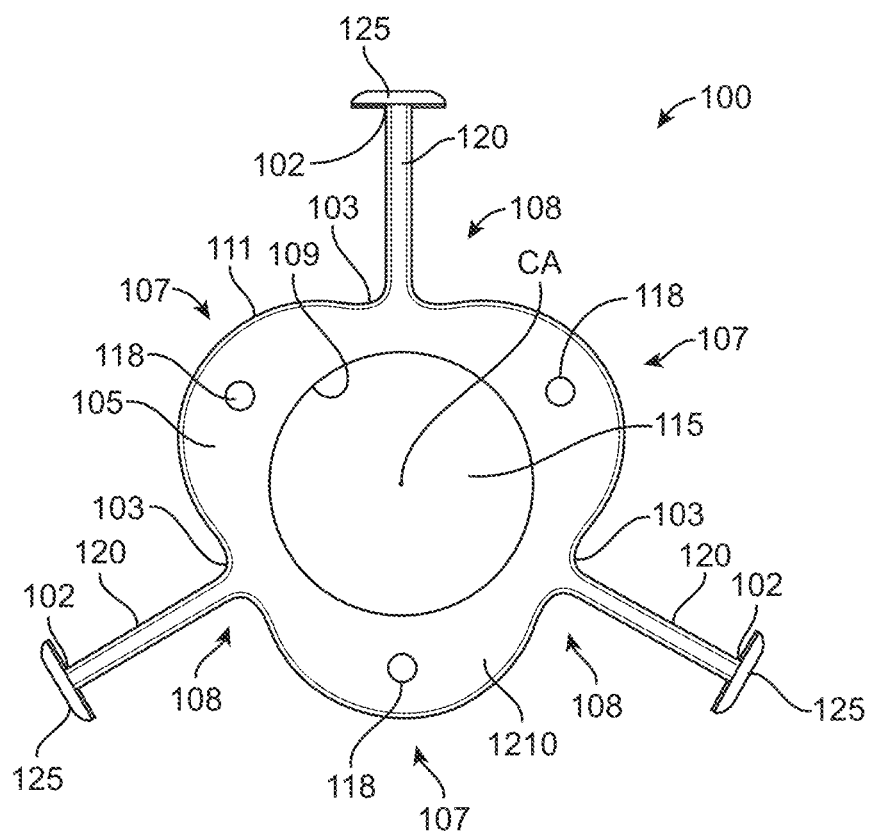
FIG. 1 shows a top down view of an implementation of a device.

It should be appreciated that the drawings herein are for illustration only and are not meant to be to scale.

DETAILED DESCRIPTION

The present disclosure relates generally to the field of ophthalmics, more particularly to ophthalmic devices, including artificial support structures that can be used to support an intraocular lens (IOL) or other ophthalmic implant when zonular and capsular support has been compromised.

The most common treatment for aphakia caused by removal of a cataractous lens is placement of an IOL within the native lenticular capsular bag. The capsular bag, which has an anterior component and a posterior component thus creating an inner chamber, is supported by zonules, thus providing a stable structure for IOL support. In some cases, the posterior aspect of the capsular bag is incompetent or ruptured during cataract surgery, necessitating a more reliable platform for positioning an IOL. If the anterior aspect of capsular bag and its associated zonules are intact, an IOL may be placed between the anterior capsule and the iris, a position referred to as the "sulcus." In another subset of cataract surgery cases, the anterior capsule is incompetent, or the zonules are incompetent, making sulcus placement unsafe or impossible. The devices described herein can be implanted into a posterior chamber of an eye that lacks an intact capsular bag. The devices described herein can create an artificial anterior capsule with artificial zonular fixation. The devices described herein can provide a stable platform structure fixated to the eye and thereby recapitulate the native anterior capsular and zonular apparatus allowing for placement of an IOL in the artificially constructed sulcus.

The devices described herein can solve problems of other support/positioning techniques known in the art. Anterior chamber intraocular lenses placed in front of the iris can cause corneal decompensation, glaucoma and bleeding over time due to their instability in the eye. Lenses sutured to the iris is technically difficult to implant and risks bleeding and glaucoma, due to chafing of the iris. Lenses may also be sutured to the sclera, which is also technically difficult. In some cases, suture erosion/breakage requires additional surgery and risk potentially blinding infection.

The devices described herein can be implanted in a sutureless manner, which eliminates the risk of suture breakage. A sutureless trans-scleral fixation method allows for easier placement and secure attachment without concern for loosening or breaking of sutures. The devices stably hold IOLs providing a reliable refractive result based on known position without concern. The devices also allow for posterior segment placement that greatly reduces risk of damage to iris, angle or cornea. Implantation posterior to iris and cornea eliminates or reduces risk of corneal injury, iris bleeding and glaucoma. The devices described herein reduce the risk of complications compared to current technologies such as ACIOL, Iris-sutured lens, or Scleral-sutured lens. The devices described herein are designed to accommodate and provide support to a wide variety of intraocular lenses. Thus, the lens of choice can be implanted at the time of surgery or at a later date. The devices described herein replicate a natural lens capsule and are particularly suitable for implantation into a posterior chamber of an eye lacking an intact capsular bag. For example, the devices described herein can create an artificial anterior capsule with artificial zonular fixation providing a scaffold or stable platform structure and an artificially constructed sulcus where the anterior component of the capsular bag and/or zonules of the natural lens are incompetent. The fixation arms can be externalized as needed for scleral support/fixation.

FIGS. 1-4 show an implementation of a device 100. The device 100 can include a lens support structure 105 upon, against, or within which an IOL 110 can be supported, a central opening or aperture 115, and one or more fixation arms 120. The central aperture 115 prevents the device 100 from interfering with the patient's vision and is adapted to permit passage of light through the aperture 115 as well as the IOL 110 positioned on the device 100. The size of the central aperture 115 allows light to pass through the device without any optical disturbance. The light may pass through the device towards the retina and is affected only by the optics of the IOL. The one or more fixation arms 120 can locate and stabilize the device 100 within the eye. The lens support structure 105 can include an outer perimeter 111 and an inner perimeter 109 and the central aperture 115 can be bound by the inner perimeter 109. The lens support structure 105 can be generally ring-shaped although the outer perimeter 111 of the lens support structure 105 need not be circular as will be discussed in more detail below. The outer perimeter 111 of the lens support structure can be substantially non-circular where the inner perimeter 109 is substantially circular.

Figure 2:
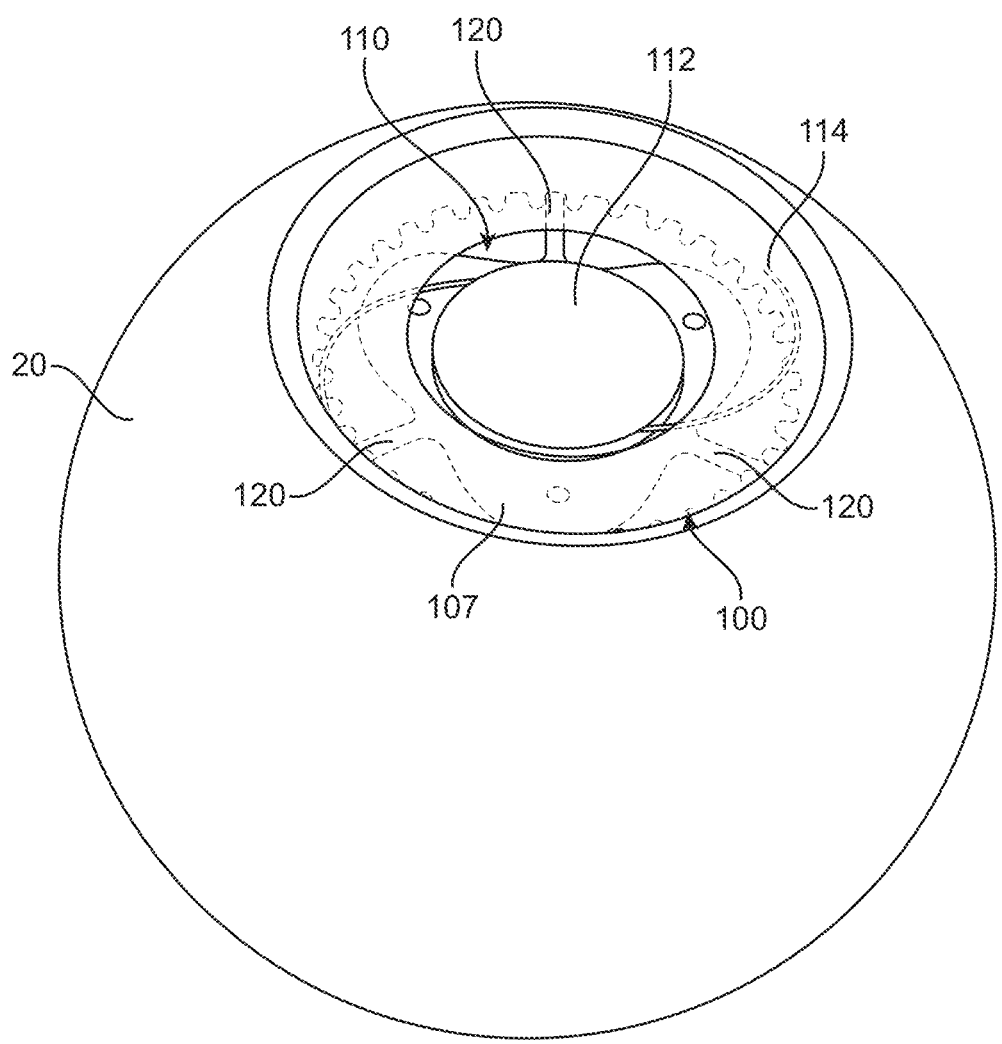
FIG. 2 shows the device of FIG. 1 deployed in the eye supporting an IOL.
Figure 3:
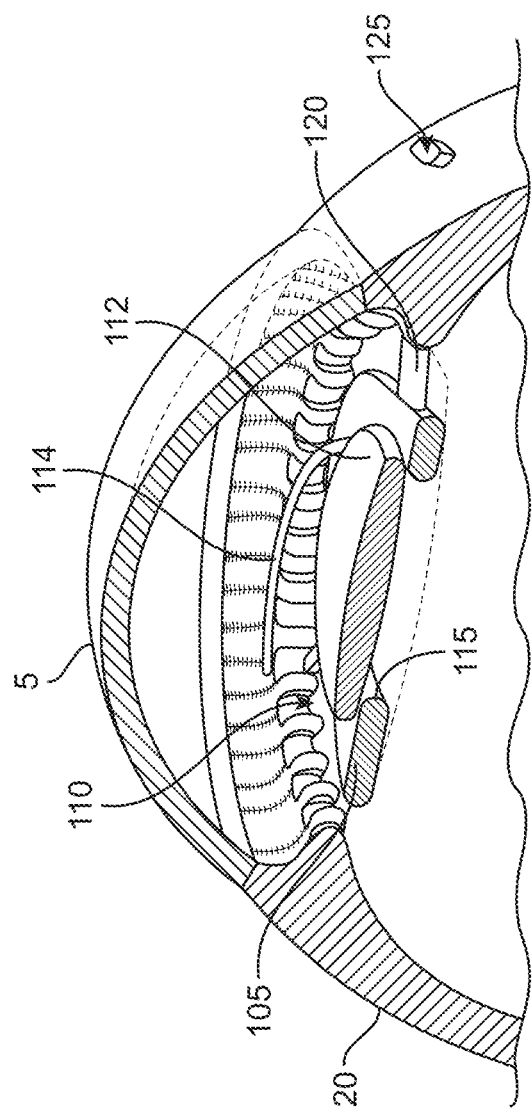
FIG. 3 shows a cross-sectional view of the device of FIG. 1 deployed to support an IOL.
Figure 4:
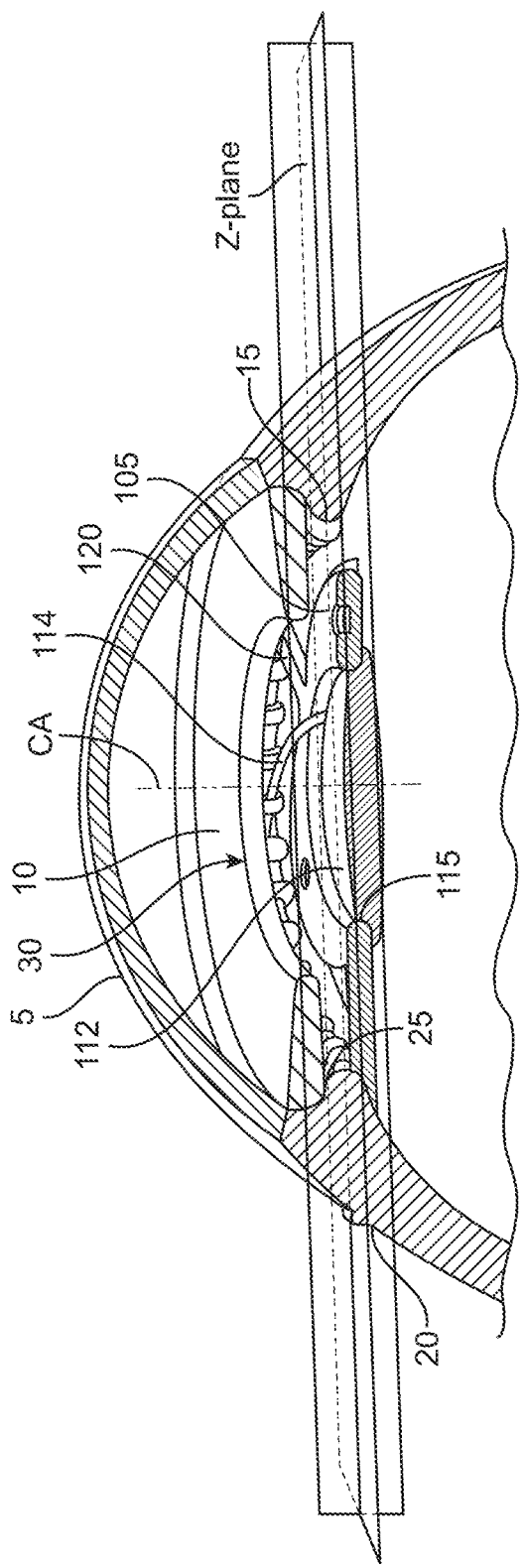
FIG. 4 shows a cross-sectional view of the device of FIG. 1 implanted in an eye supporting an IOL.

FIG. 1 shows a top down view of the device 100 showing the lens support structure 105, the central aperture 115, and the fixation arms 120. FIG. 2 shows a model of the eye with a ¾ view of the device 100 deployed to support an IOL 110 (the iris is illustrated as transparent). The lens support structure 105 can serve as a support for the IOL 110 during optimal implantation and as a guard against the IOL 110 falling into the posterior chamber during implantation. The lens support structure 105 can take the place of a native lenticular capsular bag, particularly where the anterior aspect and associated zonules are incompetent making sulcus placement of an IOL unsafe or impossible. Placement of the lens support structure 105 in a patient without a competent capsular bag can create an anterior capsule device. The fixation arms 120 can provide artificial zonular fixation stabilizing the lens support structure as a stable platform for placement of an intraocular lens within the artificially constructed sulcus. FIG. 3 shows a model of the eye and a cross-sectional view of the device 100 deployed to support an IOL 110. FIG. 4 shows a model of the eye in cross-sectional view of how the lens may be deployed to support an IOL using the optic capture technique. FIG. 4 shows the cornea 5, the iris 10, the ciliary body 15, the sclera 20, the ciliary sulcus 25, and the pupil 30 defined centrally through the iris 10.

In some implementations, the support structure 105 can be substantially flat or planar. The support structure 105 can have an anterior-facing surface 1210 directed towards a front of the eye when the structure 105 is in use and a posterior-facing surface 1215 towards a back of the eye when the structure 105 is in use (see FIG. 17E). The planar support structure 105 can act as a platform against which the IOL can be positioned. The planar anterior and posterior surfaces need not include any projections, channels, or capturing components to hold the IOL relative to it. For example, the support structure 105 can create an artificial anterior segment of the capsular bag for the IOL to be positioned against, but need not hold the IOL within an interior surface. Thus, the IOL can remain fully external to the support structure 105 during use and no projections, overhangs, or other surfaces positioned relative to the IOL aside from the substantially planar surfaces of the support structure 105. Thus, each of the anterior-facing and posterior-facing surfaces can be substantially smooth planar surfaces that are free of any projections or overhangs above the surfaces. Each of the anterior-facing and posterior-facing surfaces can also be free of any indentations, grooves, divots, or openings other than the central aperture 115 extending through it. The substantially flat support structure 105 can taper towards the central aperture 115. The tapered edge or inner wall 109 defining the aperture 115 has an anterior-to-posterior thickness that is less than an anterior-to-posterior thickness of the support structure away from the aperture 115.

Figure 19A:
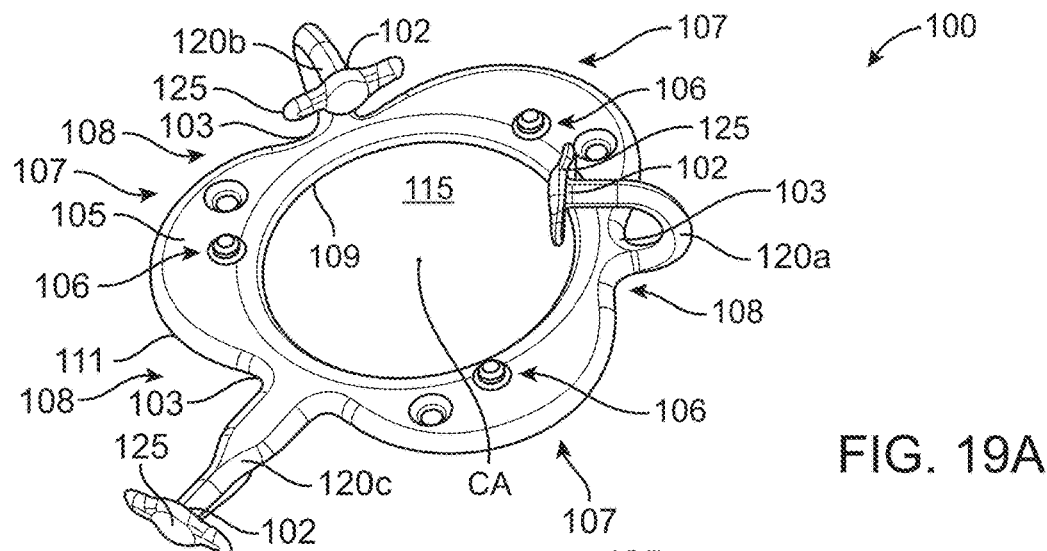
FIG. 19A shows another implementation of a device prior to implantation and having projections extending upward from an anterior-facing surface of the support structure and fixation arms biased inwardly toward a center of the device.
Figure 19B:
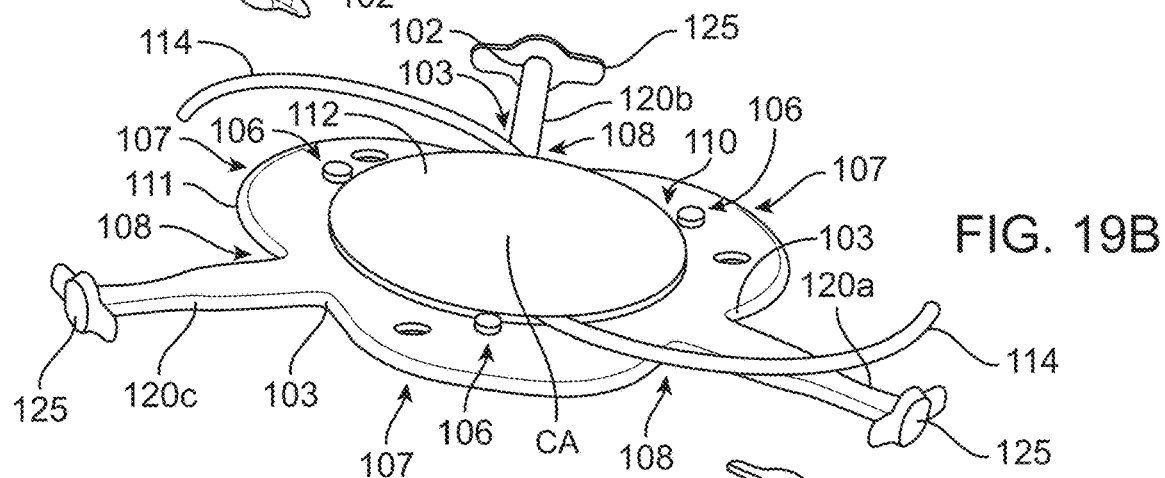
FIGS. 19B-19C shows the device of FIG. 19A after implantation and having an IOL positioned over the central aperture and each of the fixation arms tensioned.
Figure 19C:
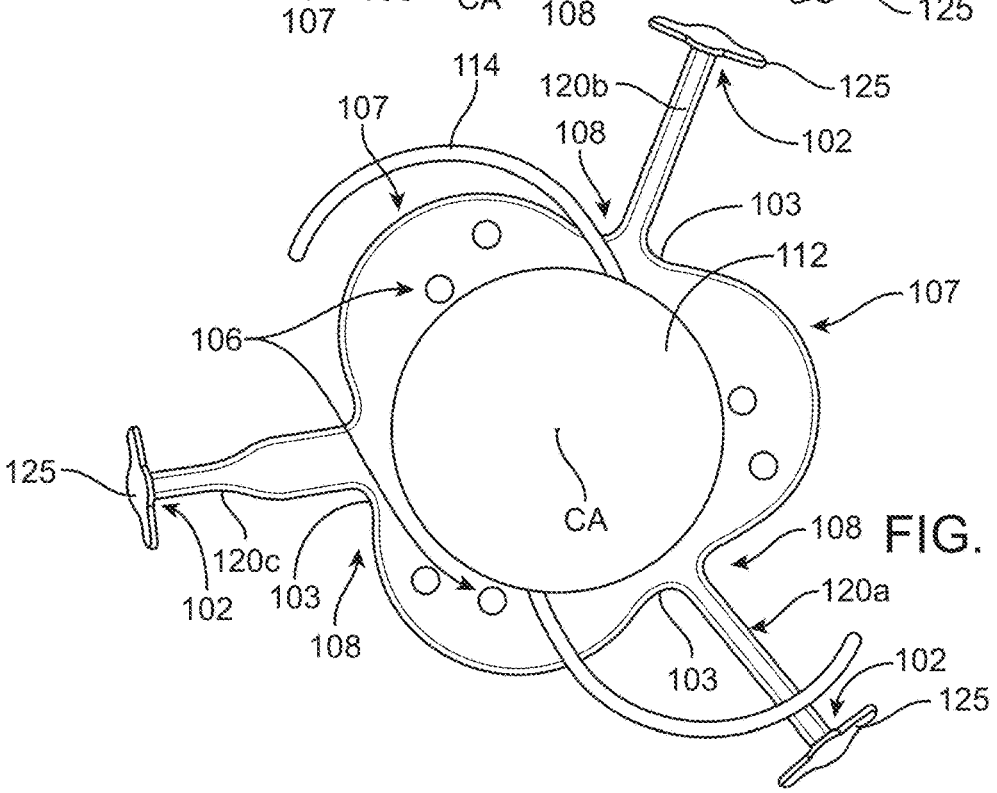

In other implementations, the support structure 105 can incorporate one or more projections extending away from at least one of the anterior-facing surface and the posterior-facing surface. FIGS. 19A-19C illustrate an implementation of the support structure 105 having a plurality of posts 106 projecting upward away from the anterior-facing surface near the central aperture 115. The plurality of posts 106 can be positioned around the central aperture 115 such that they surround the optic of the IOL upon positioning the IOL over the aperture 115 (see FIGS. 19B-19C). The posts 106 can abut against or lie adjacent the perimeter of the optic such that the IOL is received and centered by the posts 106 to limit translational and/or rotational movement of the IOL relative to the support structure 105. The posts 106 can also be positioned on the anterior-facing surface (or posterior-facing surface) such that they engage with a region of the IOL haptics extending outward from the optic. The posts 106 can be arranged such that they accommodate universally most IOL designs.

In still other implementations, the support structure 105 can optionally or additionally include a recess in at least one of the anterior-facing or posterior-facing surfaces that is sized and shaped to receive the IOL (see FIGS. 20A-20C described in more detail below). The recess can be a central inward facing groove to accommodate an IOL and/or the IOL haptics, for example, as described in PCT Publication No. WO 2020/086312, published Apr. 30, 2020, which is incorporated by reference herein.

Figure 20A:
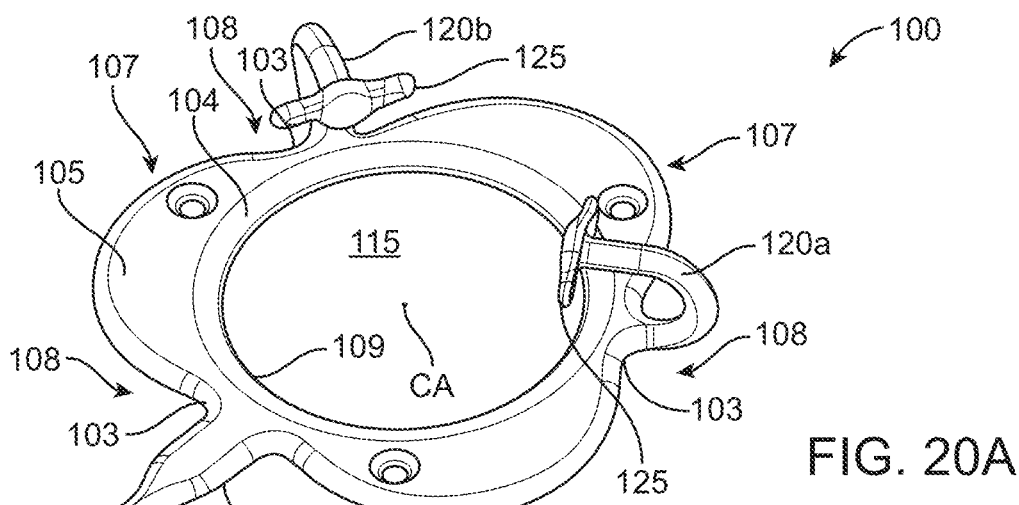
FIG. 20A shows another implementation of a device prior to implantation and having a recess within the anterior-facing surface of the support structure and fixation arms biased inwardly toward a center of the device.
Figure 20B:
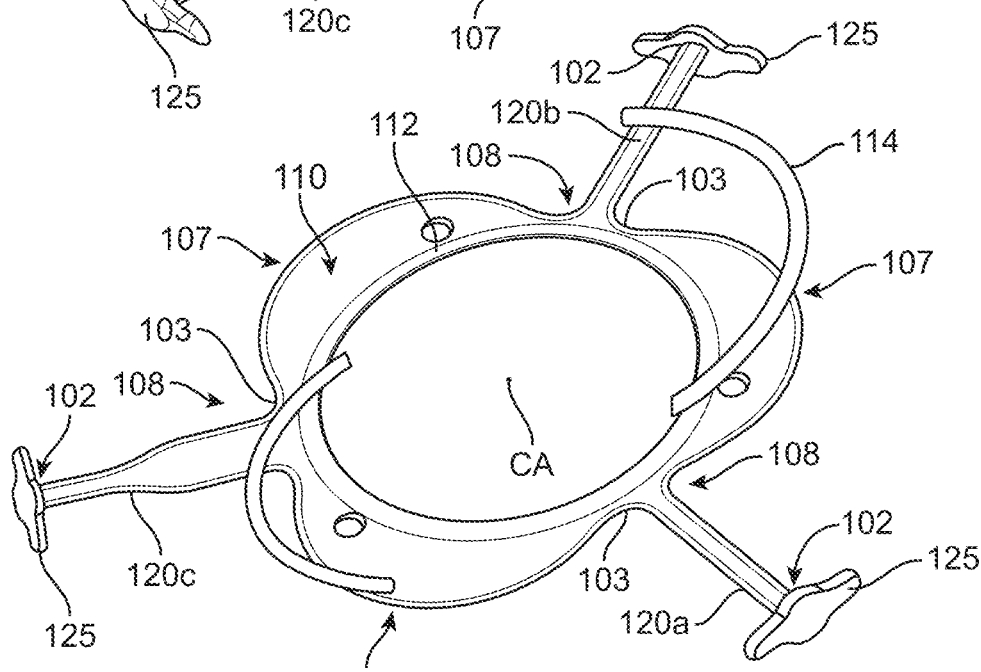
FIG. 20B shows the device of FIG. 20A after implantation and having an IOL positioned over the central aperture and each of the fixation arms tensioned.
Figure 20C:
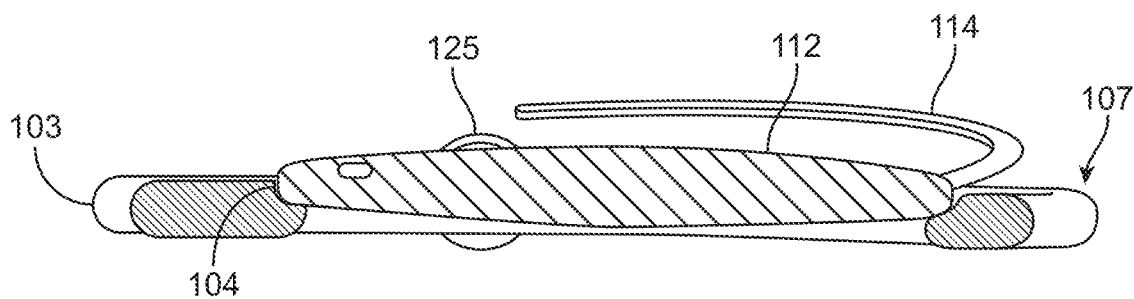
FIG. 20C is a cross-sectional view of the device of FIG. 20B showing the perimeter of the IOL optic positioned against the recess surrounding the central aperture.

FIGS. 20A-20C illustrate another implementation of the device 100 having a support structure 105 that includes a recess 104 within an anterior-facing surface. The recess 104 can form a lip surrounding the central aperture 115 that is sized to engage with and support a perimeter of the optic of the IOL against the lip (see FIG. 20C). The recess 104 in the central 6.0-7.0 mm part of the support structure 105 can limit the translational movement of the optic. The recess 104 can additionally incorporate a concave, dished out section to increase the interfacial surface area of the IOL with the support structure 105. The recess 104 can incorporate one or more features that additionally prevent rotational motion around the visual axis or the central axis CA of the device. FIGS. 24A-25F, 25A-25C, and 26A-26E illustrate additional implementations of a device incorporating a recess within which an IOL may be received and are described in more detail below.

Whether the support structure 105 is recessed or not and/or incorporates one or more projections from its surface or not, the anterior-to-posterior thickness of the support structure 105 is minimized to avoid impacting the iris 10.

The support structure 105 can include one or more surface features in or on the anterior-facing surface 1210 and/or the posterior-facing surface 1215. FIG. 1 shows the support structure 105 can include a surface feature 118 on the anterior-facing surface 1210 that can be used for positioning the device 100 during implantation. The surfaces features 118 can be engaged by forceps or other implantation tools to aid in manipulating the device 100 during implantation.

The central aperture 115 can extend through the full thickness of the support structure 105 from the anterior-facing surface 1210 through to the posterior-facing surface 1215 such that the support structure 105 additionally includes an inner wall 109 having an inner perimeter surface defining the central aperture 115 and an outer wall 111 having an outer perimeter surface defining the overall shape of the support structure 105 (see FIG. FIG. 1 and also 17E). This can provide a substantially annular shape to the lens support structure 105. However, the annular lens support structure 105 need not be circularly on both its inner and outer perimeter surfaces. The inner perimeter surface can have a circumference and form a uniform, substantially circular shape whereas the outer perimeter surface can form a substantially non-circular shape. As will be discussed in more detail below, the non-circular shape of the outer perimeter surface comprises a plurality of lobes 107 projecting outward from a plurality of sides 108. The plurality of lobes 107 can project radially away from the central aperture 115. The plurality of sides 108 can be substantially flat or concave as described elsewhere herein. In some implementations, the device includes at least three fixation arms 120 coupled to the lens support structure 105 that are configured to be placed under tension to locate and stabilize the device within the eye. Each of the three fixation arms 120 can extend outward from a respective one of the plurality of sides 108. The lens support structure 105, thus, can have a width between the outer perimeter surface and the inner perimeter surface that varies around the circumference. The central aperture 115 is designed to allow for vision through the device. In some implementations, the support structure 105 is substantially flat and the IOL sits on the anterior-facing surface (or posterior-facing surface) of the support structure 105, but is not held or contained by the central aperture 115. In other implementations, the support structure 105 is generally planar, but includes a recess 104 surrounding the central aperture 115 such that the IOL sitting on the anterior-facing surface of the support structure 105 engages a lip formed by the recess 104 (see FIG. 20C). The support structure (and thus, the central aperture 115) can have a thickness anterior-to-posterior that is minimized. The thickness of the support structure 105 between the anterior-facing surface 1210 and the posterior-facing surface 1215 can be between about 0.15 mm and 1.5 mm, or between about 0.5 mm and 1.0 mm. The thickness of the support structure 105 can be thinner than 0.15 mm and still provide sufficient support for an IOL, for example, due to the fixation arms 120 being under tension. The inner perimeter surface or inner wall 109 defining the central aperture 115 can be smooth and free of any concavity, groove, channel, or other surface feature. In some implementations, the inner perimeter surface or inner wall 109 is convex and projects towards a central axis CA of the device and the outer perimeter surface or outer wall 111 is also convex and projects away from the central axis CA of the device. The convex inner and outer perimeter surfaces formed by the inner and outer walls 109, 111 can create a cross-sectional shape to the support structure 105 when taken across a center of the central aperture 115 that forms a pair of rounded rods. In some implementations, the anterior-facing surface 1210 and the posterior-facing surface 1215 each taper towards the central aperture 115 such that the inner perimeter surface of the inner wall 109 is shaped as a single narrow ridge or point 1230 projecting towards the central axis CA of the device (see FIG. 17E).

The central aperture 115 can also be the only aperture extending through the support 105 such that the support 105 has only a single aperture extending through its full thickness. The inner diameter of the aperture 115 is designed to be generally universal for a wide range of IOL types. The aperture 115 is sized so the support 105 avoids overlapping substantially with the optic of the IOL. Conventional IOLs typically have optics with an outer diameter of 6 mm although this size can vary depending on the IOL. A device having a central aperture 115 inner diameter that is less than 5.0 mm down to about 4.0 mm can be used with some IOLs. A device having a central aperture 115 inner diameter that is between 5.0 mm to about 6.0 mm can be used with most IOLs such that the device is nearly universal for use with any conventional haptic-stabilized IOL. The minimum inner diameter of the aperture 115 can be greater than about 4.0 mm, greater than about 4.5 mm, greater than about 5.0 mm, greater than about 5.5 mm, greater than about 6.0 mm, greater than about 6.5 mm, up to about 7.0 mm, up to about 8.0 mm, up to about 9.0 mm, up to about 10 mm and any range in between.

Figure 21A:
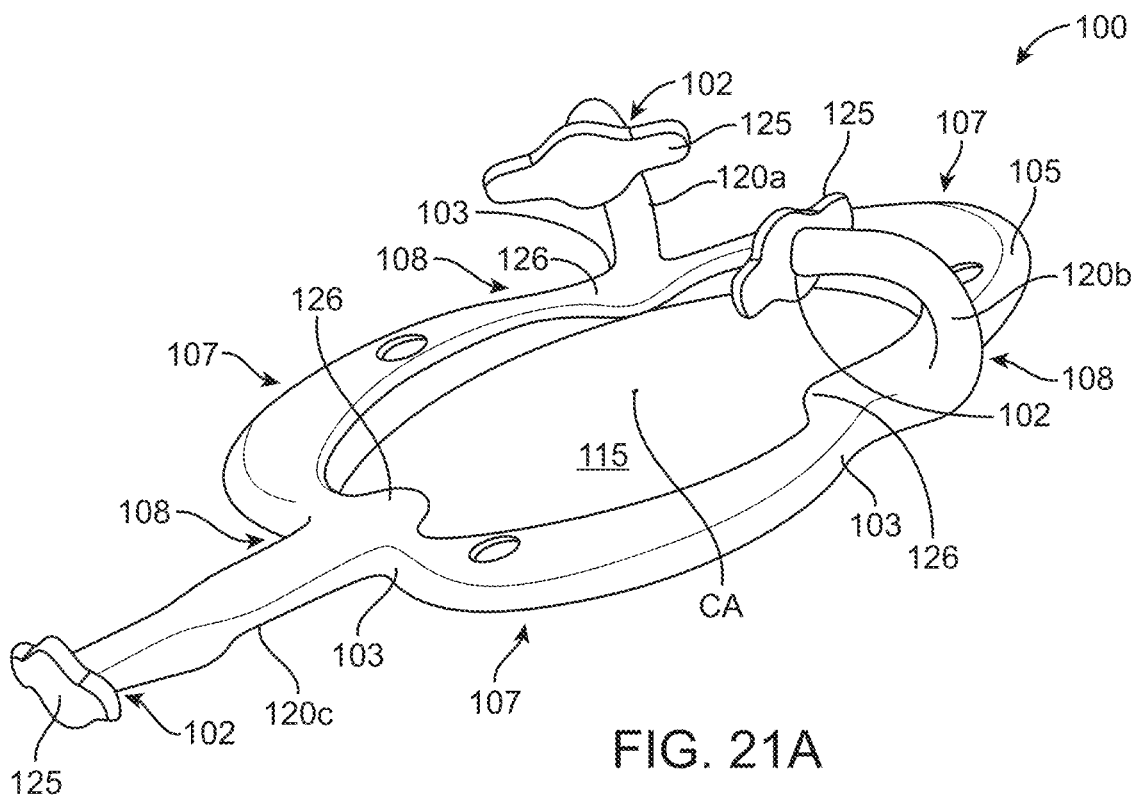
FIGS. 21A-21B show another implementation of a device incorporating an enlarged central aperture and a plurality of leaflets.
Figure 21B:
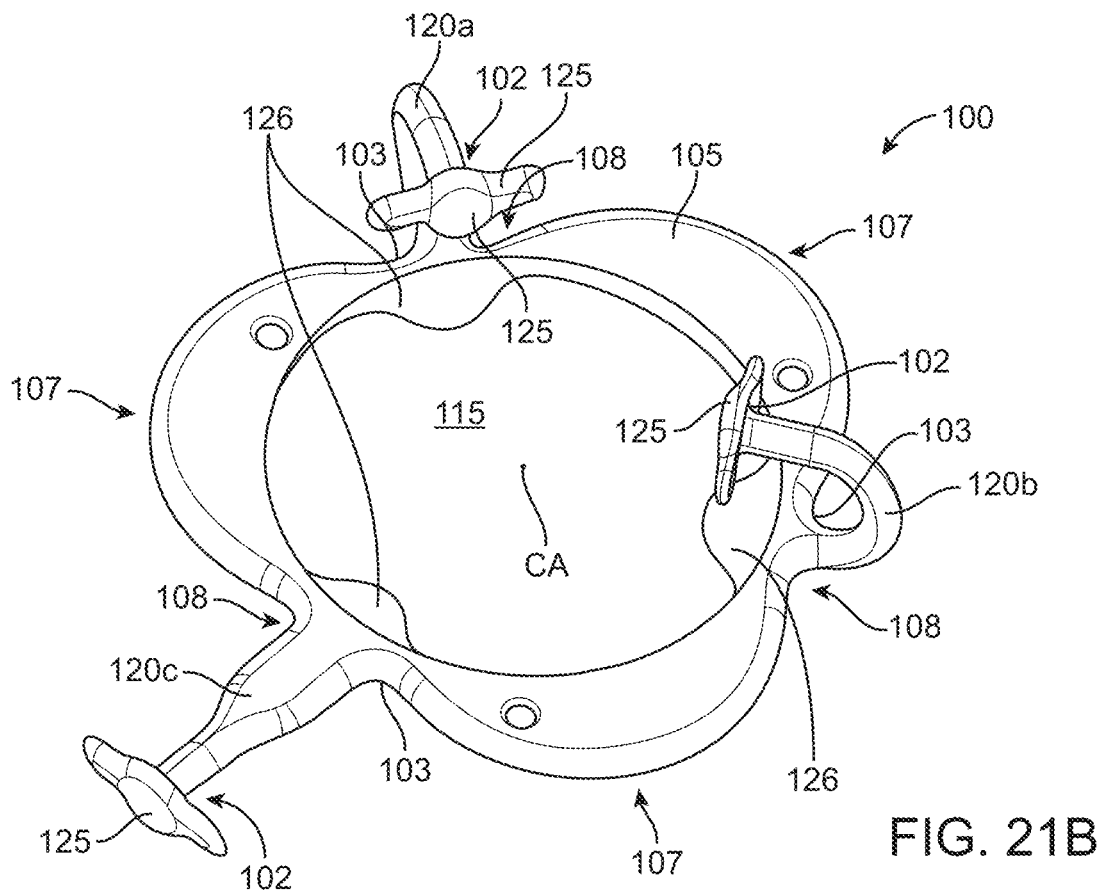

The inner diameter of the aperture 115 can be greater than an outer diameter of the IOL optic. FIGS. 21A-21B illustrate implementations of the device 100 having a central aperture 115 with an inner diameter that is larger than most IOL optics. The device 100 can include a plurality of leaflets 126 configured to support the optic of the IOL. The leaflets 126 can project inwardly such that they extend within the opening of the central aperture 115. The leaflets 126 can support the optic on their anterior-facing surface or can be deflected so that the optic passes to and is support by the posterior-facing surface of the leaflet 126. The haptic of the IOL can remain on the anterior-facing surface of the support 105 and the optic of the IOL can be positioned on the posterior-facing surface of the leaflet 126 thereby maintain a Z-position of the IOL. The leaflets 126 can be full thickness or partial thickness. Meaning, the leaflets 126 can be as thick as the support structure 105 or can be thinner than the support structure 105. The leaflets 126 can stem from the anterior-facing surface of the support 105 (see FIG. 21A). The leaflets 126 can also stem from the posterior-facing surface of the support 105 (see FIG. 21B). If stemming from the posterior-facing surface, the optic of the IOL can be positioned within the recess formed by the central aperture 115 and the anterior-facing surface of the leaflets 126. The device 100 can include one, two, three, or more leaflets 126. In an implementation, the device 100 includes three leaflets 126 and three fixation arms 120. Each of the three leaflets 126 can be arranged symmetrically around the support 105 such that each leaflet 126 is substantially aligned with the origin of a respective one of the fixation arms 120. FIGS. 21A-21B show each of the bent fixation arms 120a, 120b curve around from their origin at the support structure 105 to be positioned substantially over its respect leaflet 126. The leaflets 126 can define a narrower inner diameter than the inner diameter of the central aperture 115. The narrower inner diameter of the leaflets 126 can be from about 4.0 mm to 6.0 mm, or from about 5.0 mm to 5.5 mm, or about 5.0 mm. Each leaflet 126 can have a thickness that is from about 0.10 mm to 0.50 mm, or about 0.15 mm to about 0.35 mm, or about 0.25 mm.

One or more of the fixation arms 120 can be substantially straight between their origin with the support structure 105 and their terminal ends. The straight fixation arm or leading fixation arm 120 can extend along a single longitudinal axis L between the origin 103 and terminal end 102 without any bends or curves away from the single longitudinal axis L (see FIG. 17A-17B). The straight fixation arm(s) 120 can extend orthogonal to the outer perimeter surface of the support structure 105 outer wall 111. The longitudinal axis L of the straight fixation arm(s) 120 can be positioned orthogonal to the outer perimeter surface of the outer wall 111. The plane of the anterior-facing surface 1210 of the support structure 105 and the longitudinal axis L of the straight fixation arm(s) 120 can be parallel to one another as can the plane of the posterior-facing surface 1210 of the support structure and the longitudinal axis L.

The one or more fixation arms 120 can be trans-scleral fixation arms that are designed to be atraumatically externalized and held in place by its geometry and mechanical properties alone, i.e. not requiring sutures or glue. The externalized portion or anchor 125 (also referred to herein as an anchoring footplate or footplate) at a peripheral end (also referred to herein as a terminal end or a terminal portion) of the fixation arm 120 can sit sub-conjunctively to anchor the arm 120 in position. The anchor 125 of the fixation arm 120 can have a sturdy, but low profile geometry so as to remain stable and not re-enter the eye and minimally erode the conjunctiva. Additionally, the fixation arms 120 of the device 100 may be manufactured in a way so as to facilitate easy visualization and manipulation of the device prior to surgery. At least one of the fixation arms 120 may be manufactured to have a geometry that is substantially non-planar at rest and then be manipulated into a planar configuration during the implantation procedure and, for example, when placed under tension.

The device 100 can include one, two, three, or more fixation arms 120. In a preferred implementation, the device 100 includes three fixation arms 120 that are arranged symmetrically or equidistant around the perimeter of the support structure 105. The fixation arms 120 can center the lens support structure 105 and provide sufficient support for long-term stability. In some implementations, that may be accomplished by a single fixation arm 120. In other implementations, the one or more fixation arms includes three fixation arms 120 symmetrically arranged around a perimeter of the lens support structure. The fixation arm 120 can be constructed from a semi-rigid material or may have a geometry that provides sufficient structural rigidity.

The device 100 can also include just two fixation arms 120. These fixation arms 120 may be under equal and opposite tension when implanted and anchored trans-sclerally. Alternatively, the fixation arms 120 may be asymmetric such that one fixation arm 120 is under tension and the other fixation arm 120 has a rigidity and length that it functions as a rigid spacing element. A fixation element that is rigid or capable of applying a spring force can rely on penetration of the adjacent tissue or being wedged into place. A tensioned fixation element can rely on a slight stretch or expansion of the material once placed. One or both of the fixation arms 120 may be produced with an inward biased configuration in which the fixation arm is biased towards an anterior projecting curve or a folded configuration as described elsewhere herein. The fixation arms 120 may have a paddle like geometry that resists rotation when engaged with ocular tissue.

The device 100 can also include three or more fixation arms 120. Three fixation arms 120 can provide the device 100 with a defined fixation plane that is substantially parallel to the Z-plane (vertical plane) of the eye. The fixation arms 120 can be designed and deployed in a manner that puts each fixation arm 120 in equal and opposite tension. Alternatively, one or more fixation arms 120 may be designed to have a rigidity and length allowing to behave as a rigid spacing element. Zero, one, two, or all three or more of the fixation arms 120 can be manufactured with an inward biased design or biased towards a center of the device or the central axis CA of the device (see FIGS. 10-13, 17B-17E, 19A, 20A, 21A-21B, 22A-22B, 23A-23B, 24A-24F, 25A-25C, and 26A-26E). The inwardly biased fixation arms 120 can extend from the support structure and have a folded configuration prior to implantation. At least one, but fewer than all, of the fixation arms may be biased or curved as described herein. At least two, but fewer than all may be biased or curved as described herein. In some implementations, all of the fixation arms 120 may be biased or curve. The device can include three fixation arms, wherein two of the three fixation arms are flexible and biased towards a folded configuration, and a third fixation arm is less flexible than the other two and is biased towards an unfolded configuration. The folded configuration of each of the fixation arms can bias the terminal end portion of the fixation arms towards a central axis CA of the device. The lens support structure can be biased towards a substantially flat or planar configuration while the fixation arm(s) is biased towards the folded configuration that is not substantially flat or planar.

Once implanted and fixed trans-sclerally, the inwardly biased arms can be unbent or unfolded away from their folded, inwardly biased configuration. In a preferred implementation, two fixation arms 120 have an inward bias geometry and the third fixation arm 120 has increased cross-sectional area—increasing its rigidity. The inwardly biased fixation arms 120 can incorporate a bend between an origin of the arm with the lens support structure 105 and their terminal end. The two bent fixation arms 120 can be biased towards the central axis CA of the device towards a folded configuration.

In an implementation, the device 100 can include at least three fixation arms 120. Prior to implantation, one of the at least three fixation arms can extend in an unfolded configuration from the support structure and at least two of the at least three fixation arms extend in a folded configuration from the support structure. And, prior to implantation, one of the at least three fixation arms can be biased towards the unfolded configuration and at least two of the at least three fixation arms can be biased toward the folded configuration. After implantation, each of the arms biased toward the folded configuration can be unfolded.

Each of the fixation arms 120 can include an origin portion 103 at the support structure 105 and a terminal end portion 102 coupled to an atraumatic anchor 125 for sutureless, trans-scleral fixation. Prior to trans-scleral fixation of the anchors 125, one of the plurality of fixation arms 120 (up to all of the fixation arms 120) can include a curved fixation arm 120 that is curved between its origin portion 103 and its terminal end 102 forming a bend B (see FIG. 22A-22B) enabling visualization of at least a portion of the curved fixation arm 120 through the pupil 30 of the eye (see FIG. 13). After trans-scleral fixation of the anchors 125, each of the plurality of fixation arms 120 can be tensioned between the origin portion and the terminal end to align the support structure relative to the Z-plane of the eye. The support structure 105 is adapted to provide support for an intraocular lens. The central aperture 115 extending through the full thickness of the support structure 105 is adapted to permit passage of light through both the central aperture 115 and the IOL supported by the support structure 105. The curved fixation arm 120 can curve anteriorly such that a portion of the arm 120 such as the terminal end 102 and/or its atraumatic anchor 125 is positioned over at least a portion of the support structure 105 (e.g., the upper surface of the support structure 105 and/or over a region of the central aperture 115). Alternatively, the curved fixation arm(s) 120 can curve posteriorly such that a portion of the arm 120 such as the terminal end 102 and/or its atraumatic anchor 125 is positioned under at least a portion of the support structure 105 (e.g., the lower surface of the support structure 105 and/or under a region of the central aperture 115).

FIGS. 19A and also 20A illustrate implementations of the device prior to implantation. FIGS. 19B-19C and also FIGS. 20B-20C illustrate the device after implantation. Two of the three fixation arms 120 curve inward such that they are biased towards a folded configuration at rest. The arms 120 extend outward substantially orthogonally from the support structure 105, such as from their origin 103 at the support structure 105 and make a turn (anteriorly or posteriorly) forming a curve between the origin 103 and the terminal ends 102 of the arms 120. The curve of the arm 120 can result in the terminal end 102 of the arm 120 being positioned nearer to its own origin portion 103. In some implementations, the arm 120 curves in an anterior direction such that the terminal end 102 of the arm 120 is positioned anterior to the arm's origin portion 103 or over at least a portion of the anterior-facing surface of the support structure 105 near the arm's origin portion 103. In other implementations, the arms 120 can curve in a posterior direction such that the terminal end 102 of the arm 120 is positioned posterior to the arm's origin portion 103 or under at least a portion of the posterior-facing surface of the support structure 105 near the arm's origin portion 103. In an implementation, the anchors 125 of the curved fixation arms 120 can curve away from a first plane of the support structure (e.g., Z-plane of the eye) into a second plane that is parallel to the first plane. The second plane can be anterior or posterior to the first plane depending on whether the arms 120 curve anteriorly or posteriorly. The curve can be in a direction that is substantially transverse (e.g., X-plane) to the plane of the lens support structure 105 (e.g., Z-plane). The dilated pupil (depending on whether adult or pediatric patient) can have a diameter up to about 8 mm. The curve positions the anchors 125 of the curved fixation arms 120 to be positioned within a diameter of a circle in that second plane that is visible within the diameter of a dilated pupil so as to not impede visualization by the opaque iris, for example, between about 3 mm up to about 7.5 mm, more preferably about 7 mm. The anchor 125 of each of the curved fixation arms 120 can be positioned a distance from the center of the device, for example, about 1.5 mm, 2.0 mm, 2.5 mm, 3.0 mm, up to an no greater than about 3.5 mm, or no greater than about 4.0 mm from the center of the device. The curved arms 120 provide for positioning the terminal end portions 102 and/or the anchors 125 within this diameter or this distance from the center of the device allowing for ease of visualization. The third of the three fixation arms 120 is biased into a straight or unfolded configuration at rest. The third arm 120 extends outward orthogonally from its origin 103 at the support structure 105 and makes no turn or bend. Rather, the entire third arm 120 is entirely straight and extends substantially along a single axis. The two fixation arms that, at rest, were biased towards a folded configuration are now in an unfolded configuration, for example, by tensioning the arms 120 via the trans-scleral anchors being externalized.

The fixation arms 120 may be uniformly distributed around the device 100 to provide uniform tension. Alternatively, the fixation arms 120 may be oriented in a non-uniform distribution, for example, with three fixation arms 120 that are 90 degrees from one another. In this circumstance two of the fixation arms 120 would be 180 degrees from each other, providing opposing tension; while the third fixation arm 120 serves primarily to prevent the device 100 from rotating.

The lens support structure 105 can provide several functions. The lens support structure 105 can have a surface (anterior-facing surface 1210 or posterior-facing surface 1215) forming a stable platform against which an IOL 110 can be placed during use. The lens support structure 105 can take the place of a capsular bag, particularly one where the posterior and/or anterior aspects of the bag are ruptured or otherwise incompetent. Its geometric and mechanical function not only supports the IOL 110 when in use, it can also serve to assist in the centration of an IOL 110 in the case of an asymmetric eye or asymmetric surgical procedure. The lens support structure 105 can be coupled to the one or more fixation arms 120. Where the lens support structure 105 provides artificial anterior capsule support for the IOL, the fixation arms 120 provide artificial zonular apparatus. Thus, the device provides a stable platform structure fixated to the eye recapitulating the native anterior capsule and zonular apparatus that would normally allow for placement of an IOL. The lens support structure 105 geometry and mechanical properties can be designed to allow the fixation arms 120 to function as intended and also withstand any torsional or tensile forces that may be imparted by the fixation arms 120.

The fixation arms 120 and lens support structure 105 are designed such that a properly fixated device 100 will position the central aperture 115 in a manner that will not interfere with the patient's vision. The surgeon can place an IOL 110 on through the lens support structure 105 thereby providing the patient with their needed refractive correction.

The ciliary body has a substantially circular or elliptical shape, with the vertical axis being 0.5 mm longer than the horizontal axis on average. The lens support structure 105 can interface with a patient's ciliary body to provide centration of the device 100 within the eye. A substantially round or elliptical lens support structure 105 can provide centration with the similarly round or elliptical ciliary body. However, matching of the shapes and 360 degree contact between the lens support structure 105 and the ciliary body can lead to inflammation or damage, which could negatively impact aqueous production. In a preferred implementation, the lens support structure 105 has a continuous inner circumference forming a uniform, substantially circular shaped inner wall 109 defining the central aperture 115 and an outer perimeter surface forming a substantially non-circular shaped outer wall 111 providing the lens support structure 105 with a substantially non-circular geometry (see FIG. 1). The non-circular outer geometry of the lens support structure 105 can provide centration of the device 100 without 360 degree contact with the ciliary body along the substantially non-circular shaped outer perimeter surface. The shape of the lens support structure 105 can provide sufficient contact between the lens support structure 105 and the ciliary body to aid in centration and support of an IOL 110 without causing inflammation and damage. In some implementations, the shape of the lens support structure 105 allows for contact with the ciliary body that is about 120 degrees or less, preferably between 1 and 45 degrees, or between 1 and 20 degrees. Limiting the contact to 120 degrees or less significantly reduces the risk of inflammation or impairment of aqueous production. A substantially non-circular or elliptical lens support structure 105 allows allow for gentle contact between the device 100 and the ciliary body that provides centration without requiring an exact match with the patient's specific dimensions. The radius of curvature of the lens support structure 105 can be less than that of the ciliary processes. Thus, the lens support structure 105 can contact the ciliary processes at 3 distinct points rather than across a calculable range. For example, when in use, the substantially non-circular shaped outer perimeter surface of the lens support structure 105 can contact the ciliary processes at these three distinct points. In other implementations, the lobes 107 of the device 100 are positioned near, but avoid contacting eye tissues (e.g., the ciliary body) once each fixation arm 120 is implanted and placed under tension. This arrangement allows for the lobes 107 to help in centration of the device and to avoid over-tensioning one arm 120 relative to another arm 120. If a fixation arm 120 is pulled too far during externalization of its anchor 125, the neighboring lobes 107 on either side of that fixation arm 120 may abut against the ciliary body during implantation urging the support structure 105 away from the ciliary body and promoting the device 100 into a more central alignment. Once implanted, the lobes 107 of the device can be positioned near eye tissue (e.g., the ciliary body) with or without touching the eye tissue. The tensioned fixation arms 120 can pull on the support structure 105 substantially equally around its perimeter. The tension applied around the support structure 105 can substantially align a central axis CA of the device 100 extending through the central aperture 115 with the visual axis of the eye and allow for the planar surface of the support structure 105 to be stabilized substantially parallel to the Z-plane (vertical plane) of the eye. The central axis CA of the device 100 need not be perfectly aligned (coincident) with the visual axis of the eye.

The non-circular outer wall 111 of the lens support structure 105 can include a plurality of lobes 107 projecting outward (i.e., in a convex manner) from a plurality of sides 108 that are substantially flat or concave. This can form an outer wall 111 of the lens support structure 105 having an alternating pattern of convex lobes and concave or flat sides. In a preferred implementation, the lens support structure 105 can include three convex lobes 107 or rounded corners projecting between three flat or slightly concave sides 108 providing the lens support structure 105 with a triangular shape or rounded triangle shape (see FIG. 1). The lobes 107 can act as bumpers against the ciliary body 15 and/or within the ciliary sulcus 25 to provide anti-rotation function in the Z-plane and/or prevent displacement within the Z-plane to maintain proper alignment between the central aperture 115 and the eye's visual axis (see FIG. 4). The plurality of fixation arms 120 can be positioned on the sides 108 and the plurality of lobes 107 project outward between the plurality of fixation arms 120. The fixation arms 120 each can have a length that is longer than a distance the lobes 107 project outward. As mentioned above, the lens support structure 105 can have a circular inner wall 109 defining the central aperture 115. The plurality of lobes 107 projecting outward from the central aperture 115 provides a varying thickness in the plane of the central aperture 115 between the inner wall 108 and outer wall 111. The thickness of the lens support structure 105 between the inner wall 108 and the outer wall 111 at the location of the substantially flat sides 108 is less than a thickness of the lens support structure between the inner wall 108 and the outer wall 111 at the location of the lobes 107. The number of lobes 107 forming the rounded corners of the lens support structure 105 can vary providing the lens support structure with any of a variety of non-circular shapes including rounded triangle, rounded rectangle, rounded pentagon, rounded hexagon, trefoil, quatrefoil, cinquefoil, etc. The projections or corners of these non-circular geometries can be rounded to provide gentle, non-penetrating contact with ciliary tissue such as the ciliary body. Alternatively, the device 100 can be designed to utilize the pars plana or scleral wall for centration assistance. In this implementation, the device 100 can be positioned posterior to the ciliary processes.

The plurality of lobes 107 can include at least three convex lobes providing the lens support structure 105 with a substantially rounded triangular shape. A first numerical count of the plurality of lobes 107 can equal a second numerical count of at least three fixation arms 120 where each of the lobes 107 is spaced between adjacent fixation arms 120. The lobes 107 can be symmetrically spaced around the outer perimeter of the lens support structure between adjacent fixation arms. Each of the at least three fixation arms 120 can be symmetrically spaced around the outer perimeter of the lens support structure 105 between the adjacent lobes 107.

Each fixation arm 120 can have a spring force that is a function of elongation of the material when under a load. In contrast, an open loop haptic or coil spring may have a spring force provided due to bending of a material that has a substantially fixed length. The fixation arms 120 once anchored in the eye can be under tensile stress and material elongation. For example, each fixation arm 120 can provide for extension over a radius of between about 7.5 mm to 8.0 mm to accommodate diameters between about 15 mm to about 16 mm. The device has an operable range of tension for function. As an example, the device can be under a first amount of tension once implanted (X tension). The first amount of tension is the amount of tension in the minimum acceptable diameter. In other words, the device is under a minimum amount of tension in order to function, but is capable of being placed under greater tension to accommodate larger diameters. In the example of fixation arms 120 capable of accommodating both 15 mm and 16 mm extension, each force transfer arm can operate while under the first tension X and while under at least a second tension. The second tension can be the sum of the first tension X plus a distance of tension (e.g., 0.5 mm of tension). The fixation arms can withstand the differential tension available in each extension ratio. To further illustrate the example, if each fixation arm 120 in this implementation is about 4 mm long, then the second tension (X tension+0.5 mm of tension) can undergo a 12.5% increase in elongation to function at the 15 mm diameter and also function up to the 16 mm diameter. If the fixation arms 120 in this example are 2 mm long, then the second tension (X tension+0.5 mm of tension) can undergo a 25% increase in elongation to function at the 15 mm diameter and also function up to the 16 mm diameter. If the fixation arms in this implementation that are about 6 mm long, then the second tension (X tension+0.5 mm of tension) can undergo a 6.25% increase in elongation to function at the 15 mm diameter and also function up to the 16 mm diameter. The decreased spring force of the fixation arms 120 can enhance the safety and function of the device because the tension of the anchor on the ocular tissue is less dependent on variables that are difficult for the surgeon to assess—the eye's inherent dimensions and the specific location of the incisions. Additionally, the length of the fixation arm (e.g., between about 2 mm to 6 mm) as well as the inward curve (anteriorly or posteriorly) of at least one or more fixation arm 120 improves access and visualization for the surgeon to find and fix the arm during the operation.

With only one, two, or three fixation arms 120 engaged, it can be possible for an IOL 110 to pass between the device 100 and the ciliary processes. A lens support structure 105 designed to contact or nearly contact the ciliary body can also reduce the risk of losing an IOL 110 into the posterior chamber during surgery.

The lens support structure 105 can be constructed such that a surgeon can use the "optic capture" technique for implantation of an IOL 110 to be supported by the device 100. In this technique, the optic 112 of the IOL 110 is passed partially or completely through the central aperture 115 of the device 100 while the haptics 114 of the IOL 110 remain substantially anterior to the device 100 (see FIG. 3). This technique provides secure fixation of the IOL 110 so that it cannot drift in the X, Y or Z axis following surgery and reduces bulk in the space anterior to the lens. The technique additionally allows for safe use of "square edge" IOL designs by mitigating IOL contact with the posterior surface of the iris 10. Surgeons have added flexibility in modifying IOL power by offering a choice in effective lens position. The technique also allows for the use astigmatism-correcting IOLs by limiting IOL rotation. In some circumstances, there may be limited space between the anterior surface of the lens support structure 105 and the posterior surface of the iris 10. In order to reduce the risk of iris damage or pupillary block, it would be advantageous to fix the IOL 110 on or posterior to the plane of the lens support structure 105. Additionally, securing the optic while enhancing the predictability of its refractive position makes pre-operative lens choice calculations more accurate.

In order to facilitate the use of the optic capture technique, the lens support structure 105 can allows the surgeon to pass an IOL 110 through the aperture 115 of the device 100. The aperture 115 can have a diameter that is similar to that of common IOL optic diameters, for instance at least 5.5 mm or 6.0 mm. In this circumstance, the surgeon can pass the IOL 110 through the aperture 115 with force parallel to the optical axis or by slightly tilting the IOL 110 to ease the IOL 110 through the aperture 115. The aperture 115 can have an inner diameter that is greater than 5 mm, for example, 5.5 mm, 6.0 mm, 6.5 mm, 7.0 mm, 7.5 mm, 8.0 mm, 8.5 mm, 9.0 mm, 9.5 mm, and 10.0 mm up to about 15 mm and anywhere in between.

Alternatively, the device 100 can incorporate features that allow the diameter of the aperture 115 to temporarily enlarge to allow the IOL 110 to pass through the aperture 115. The support 105 can have an outer perimeter wall and an inner perimeter wall that are discontinuous such that the support structure 105 forms a split-ring having a gap between terminal ends of the ring. In this implementation, the inner diameter of the aperture 115 can change depending on whether the terminal ends of the ring or compressed toward one another or spread apart. In another implementations, the outer perimeter wall can be a full ring shape or continuous in circumference and the inner perimeter wall defining the aperture 115 can be discontinuous or continuous. The single aperture can have a continuous inner circumference without any gaps, grooves, or channels. Alternatively, the single aperture can have a discontinuous inner circumference. FIG. 5 shows an implementation of the device 100 having one or more slits 113 formed in the inner wall 109 defining the aperture 115. The device 100 can include more than a single slit 113, for example, 2 to 40 slits 113 in the inner wall 109 circumferentially located around the aperture 115. The slits 113 can preferably have a length sufficient to extend from the inner diameter of the aperture 115 radially outward 0.25 mm-2.0 mm thereby increasing flexibility of the support structure 105. The IOL 110 can be passed through the pliable lens support structure 105. Alternatively, the device 100 can incorporate one or more deflectable flaps 116 molded into the lens support structure 105 (see FIG. 6). The device 100 can include more than a single deflectable flap 116, for example, 2 to 40 flaps 116 that would deflect and allow the IOL 110 to pass through the aperture 115 when under sufficient force imparted by the surgeon. Alternatively, the inner wall 109 can have a brush-like structure that deflects and allows the IOL 110 to pass when under sufficient force imparted by the surgeon. In still further implementations, the cross-sectional thickness profile of the lens support structure 105 may be tapered towards the aperture 115. The outer perimeter of the lens support structure 105 near the outer wall 111 would have a greater thickness (e.g., thickness measured anteriorly-to-posteriorly when the device is positioned in the eye) than the thickness of the inner perimeter of the lens support structure 105 near the inner wall 109. Thus, the center-most portion of the lens support structure 105 (i.e., the inner wall 109) would have greater flexibility due to the reduced thickness allowing an IOL 110 to pass through the aperture 115 and deflect the inner wall 109 when placed under sufficient force. Despite the greater flexibility near the inner wall 109 whether due to slits 113, flaps 116, or a reduced thickness, the lens support structure 105 has sufficient strength to support an IOL 110 resting on the anterior surface of the lens support 105 or an IOL that is partially or completely posterior to the lens support 105.

Figure 7A:
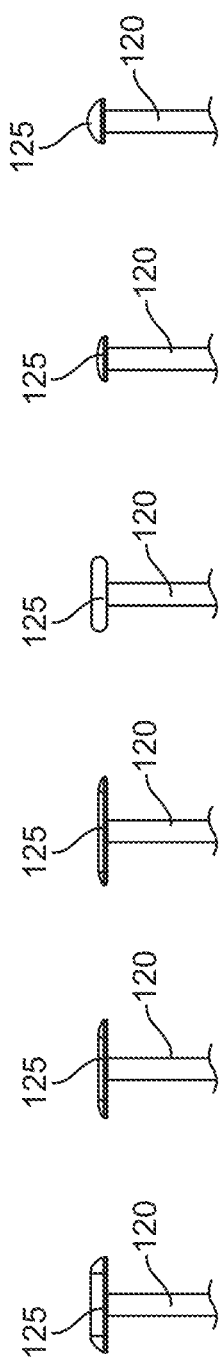
FIGS. 7A-7B show various implementations of designs for anchoring footplates.
Figure 7B:
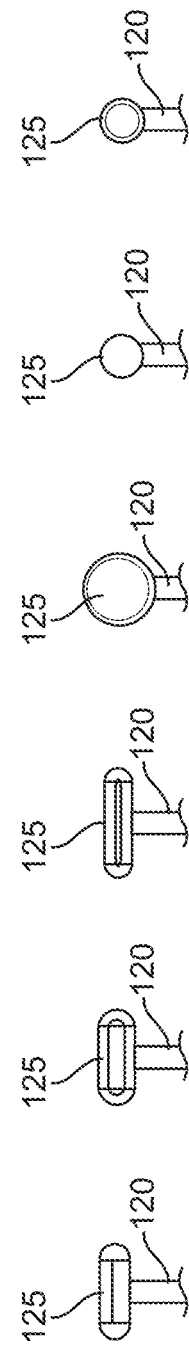

FIGS. 7A and 7B illustrate various fixation arms 120 with terminal footplates or anchors 125. The anchors 125 can be coupled to or positioned at an outer terminus of the fixation arms 120. These geometries are designed to be easily externalized by the surgeon and to stabilize tension on the device throughout its useful life. The anchors 125 can have a generally low profile and can have a geometry (e.g., rounded) designed to limit conjunctival erosion and eyelid irritation. The terminal end of the fixation arm 120 can have an anchor 125 configured to be positioned external to the sclera 20 to secure the lens support structure 105 and prevent centripetal slippage. The geometry of the anchor 125 allows for the surgeon to pass the anchor 125 through a puncture or incision in the sclera 20 using forceps, trocars or other surgical tool. A snare device for anchor extraction is described in more detail below. The anchor 125 can have a geometry that resembles a nail head, a T-bar, a multi-pronged shaped, or any other geometry that can preferentially be passed through the sclera 20 in a first direction and resist pulling out the direction of insertion to maintain its external position when the arm 120 is placed under the tension anticipated through the lifetime of the device. The anchor 125 is designed to have a profile and geometry that does not cause irritation to the eyelid or conjunctiva throughout the useful life of the device 100. As such, preferred geometries will have minimal thickness profiles with smooth, rounded and/or tapering edges. The anchor 125 can have a substantially constant thickness or can have a thickness that various over its length, as discussed in more detail below.

Figure 8A:
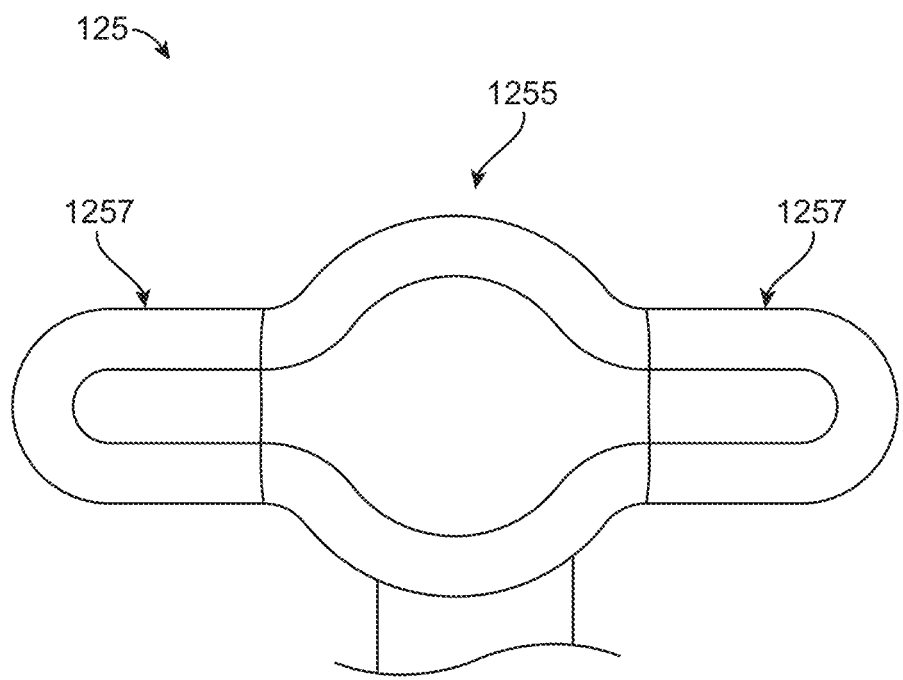
FIGS. 8A-8C show another implementation of an anchoring footplate coupled to a terminal end of a fixation arm.
Figure 8B:
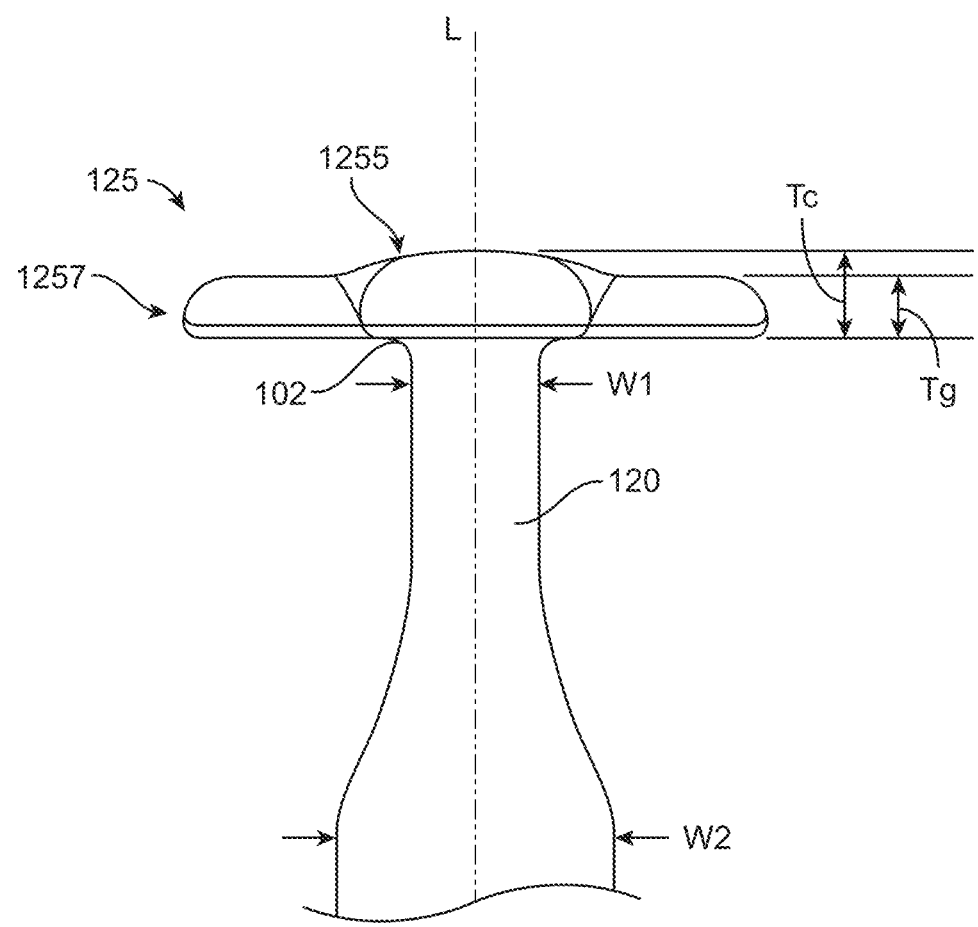
Figure 8C:
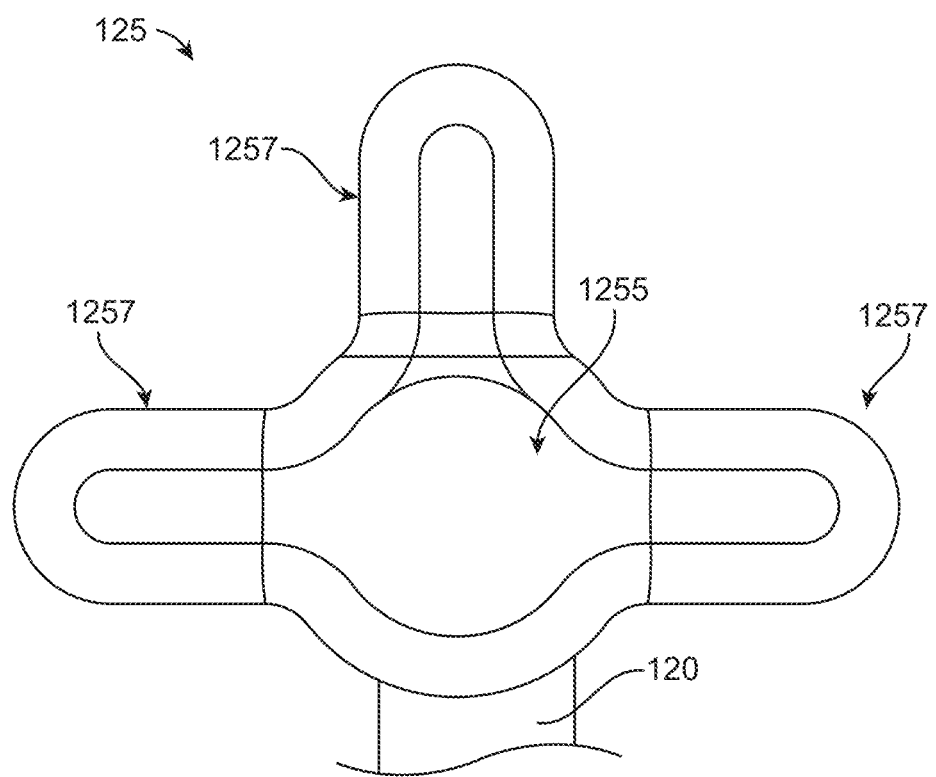

The anchors 125 described herein are configured to be both easily externalized and resistant to re-internalization following externalization. The anchors can be designed such that they are graspable using an ophthalmic tool (e.g., 23, 25, or 27 gauge). A geometry that is ideal for grasping with an ophthalmic tool may not necessarily be ideal for firm fixation. FIGS. 8A-8C illustrate additional geometries of the anchors 125 that have variations in thickness, width, and/or height. The anchors 125 can include a central portion 1255 and one or more graspable portions 1257 at a periphery of the central portion. The central portion 1255 can be arranged to lie over the wound (sclerotomy) through which the anchor 125 was inserted and the graspable portions 1257 arranged immediately adjacent the wound. The central portion 1255 can have increased thickness, height, and/or width compared to the graspable portions 1257 at the periphery. The increased thickness, height, and/or width of the central portion 1255 can add bulk to the area over the wound and thereby reduce the likelihood that tension on the fixation arm pulls the anchor 125 back through the wound. The central portion 1255 of the anchor 125 may have a thickness Tc along a longitudinal axis L of the arm 120 that is greater than a thickness Tg of the graspable portion 1257. For example, the thickness Tc can be between about 1.2 to 5.0 times as thick as a thickness Tg of the graspable portion 1257. In other implementations, the central portion 1255 may have a width or height that is between about 1.2 to 5.0 times as wide or as high as the graspable portions 1257. The geometry of the bulkier area is designed to resist deformation when under the tensile forces associated with normal use of the device. The bulkier central portion 1255 can collapse inward to fold over onto the terminal end of the arm 120 to which it is attached during externalization. Once the arms 120 are placed under tension, the bulkier central portion 1255 is incapable of being folded over away from the terminal end of the arm 120 onto itself, which prevents the externalized anchor 125 from being pulled back through the wound. Thus, the central portion 1255 can be pulled through the wound in the first direction (outward from the eye) despite its greater bulk, but is prevented from being pulled through the wound in the second opposite direction (inward towards the eye) because of its greater bulk.

The graspable portions 1257 can include any of a variety of shapes, including ovoid, rectangular, star-like pattern, or other shape or geometry that improves grasping of the graspable portions 1257 compared to, for example, the central portion 1255. The graspable portion 1257 may have a thinned and narrow tab that extends from the central portion 1255. Each anchor 125 may include 1, 2, 3, 4, 5, 6, or more graspable portions 1257 to allow the user to grasp the anchor regardless of the conformation of the device.

Figure 9:
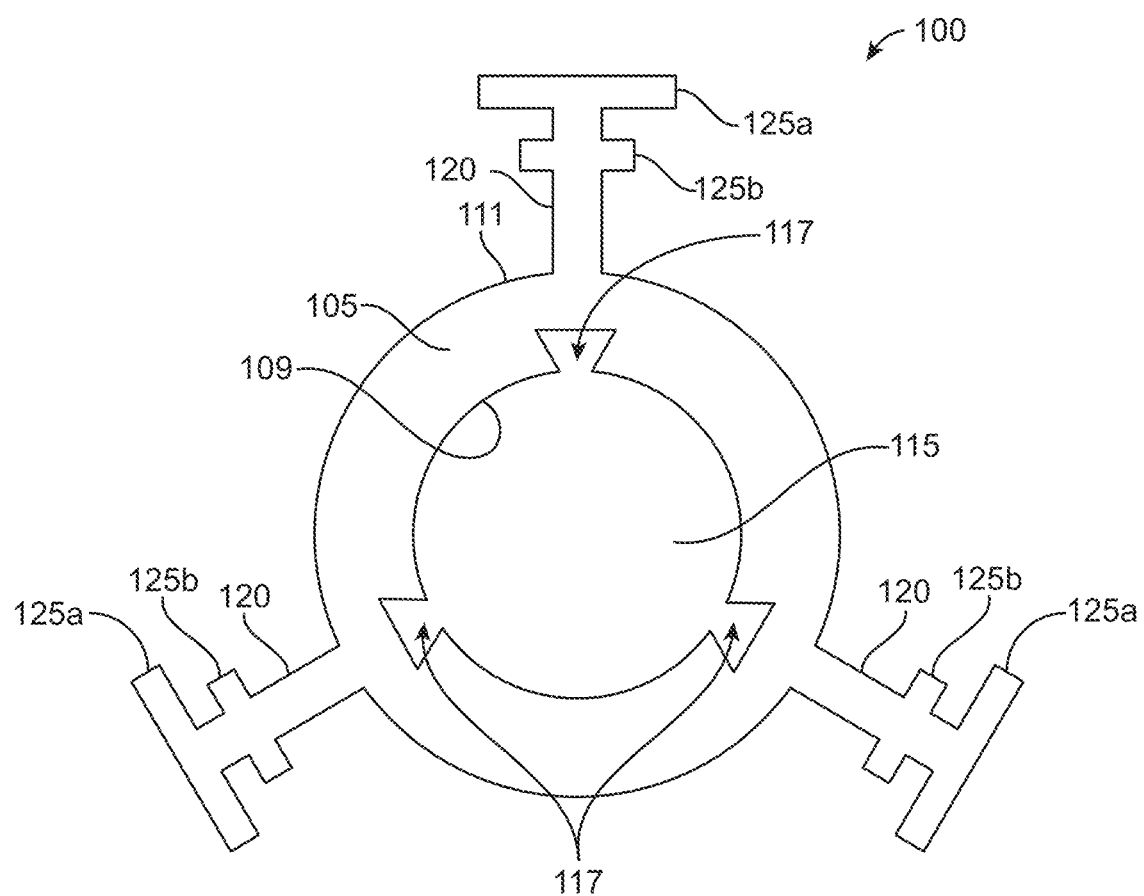
FIG. 9 shows a top down view of an implementation of the device having multiple anchors on each fixation arm.

In some implementations, each fixation arm 120 can have more than a single anchor 125. FIG. 9 illustrates an implementation of a device 100 having three fixation arms 120, each having a first anchor 125a on a terminal end and a second anchor 125b positioned internal to the first anchor 125a. The second anchor 125b can further secure the lens support structure 105 by preventing centrifugal slippage. Alternatively, the second anchor 125b can be externalized through the sclera 20 such that the second anchor 125b also holds the device 100 in place. In this circumstance, the surgeon has the option to trim any material of the fixation arm 120 positioned peripheral to the second anchor 125b (e.g., the first anchor 125a). This multiple anchor system allows for the surgeon to size the device 100 to the patient's eye intraoperatively. Each fixation arm 120 can include a plurality of anchors 125 that can be positioned along a length of the fixation arm 120. The plurality of anchors 125 can include 2, 3, 4, 5, or more anchors 125 evenly spaced along its length. As the fixation arm 120 is externalized through the sclera, the length of the fixation arm 120 can be "customized" depending on the number of anchors 125 that are also externalized. The surgeon may externalize as many anchors 125 as necessary to center the device 100. The excess material of the fixation arm 120 and anchors 125 peripheral to the external anchor 125 nearest the sclera 20 can be removed such as by trimming. FIG. 9 illustrates the two anchors 125a, 125b have different outer dimension with the inner anchor 125b being narrower than the outer-most anchor 125a. It should be appreciated that the plurality of anchors 125 can also have the same dimension and need not vary in their size. The anchors 125 can also have a geometry that improves their passage through the sclera in a first direction, but impairs their passage through the sclera in a second, opposite direction. For example, FIG. 9 illustrates square edges of the anchors 125. However, the anchors 125 can have a square edge on an inner-facing surface and a smooth tapered edge on an outer-facing surface that aids in their passage through the sclera in an outward direction.

Fixation arms 120 extending to the eye wall can be difficult to manipulate as they can be blocked from view by the peripheral iris 10, limbus and sclera 20. As discussed above, one or more of the fixation arms 120 can be inwardly biased toward a folded configuration. Each of the fixation arms 120 may extend initially from the support structure 105 outward in an orthogonal direction and then curve or fold anteriorly (or posteriorly) such that the terminal ends of the fixation arms 120 are positioned over at least a portion of the fixation arm 120, the support structure 105, or the central aperture 115 extending through the support structure 105. At least a portion of the bent fixation arms (i.e., the terminal ends and/or the anchors 125) can be more easily visualized through a dilated pupil and visualization is not impeded by the opaque iris 10 (see FIG. 13). This inward (centripetal) bias also allows the bent fixation arms 120 to be safely grasped and manipulated during device implantation. Each of the fixation arms 120 of the device 100 can have inward bias toward a folded configuration or just a selection of the fixation arms 120 can have inward bias (e.g., one, two, up to less than all fixation arms 120).

The device 100 can be produced without inward bias and the inward bias set using a manual manipulation of the device. The manipulation may be performed by the manufacturer or by the surgeon. The goal of the manipulation is to temporarily position at least a portion of the fixation arms 120 such that they can be easily visualized through the dilated pupil during implantation. The manipulation may involve suturing two, or more, fixation arms 120 together. The suture can be removed once the surgeon is ready to manipulate the fixation arms 120 individually within the eye. The device 100 structure can incorporate one or more features that allow for a fixation arm 120 to be temporarily engaged with the lens support structure 105 in a way that assists with visualization of the fixation arm 120. For example, FIG. 9 shows the inner wall 109 defining the central aperture 115 can include one or more notches 117 that can be used to temporarily hold the fixation arms 120 in an inward biased position. The shape of each notch 117 is complementary to a shape of the fixation arm 120 so that it can receive at least a portion of the fixation arm(s) 120 within the notch 117. The manufacturer or surgeon can fold, twist, or otherwise manipulate the fixation arm 120 into the notch 117. Following insertion into the eye, the surgeon can disengage the fixation arm 120 from the notch 117 and proceed to externalize the fixation arm 120 through the sclera. The notch 117 is shown in FIG. 9 on the inner diameter or inner wall 109. However, the notch 117 can be on another surface of the device 100 including a peripheral surface (e.g., outer wall 111), anterior surface, or posterior surface of the lens support structure 105.

The fixation arm 120 can also be molded to incorporate a bend or curve between its origin with the lens support structure 105 and the terminal anchor 125 (see FIGS. 10-12, FIGS. 17B-17E, FIG. 19A, 20A, 21A-B, 22A-22B, 23A-23B, 24A-24F, 25A-25C, 26A-26E, and FIG. 27). The bent fixation arm(s) 120 can be biased towards a folded configuration. For example, one or more of the fixation arms 120 can bend between 90 degrees and 270 degrees from its origin with the lens support structure 105 in a radial and centripetal direction. The terminal end of the bent fixation arms 120 thus, lie in a different plane from a plane of the lens support structure 105. When in a resting state prior to being positioned in the eye, the terminal end of at least a first fixation arm 120 of the plurality of fixation arms 120 can incorporate a bend between its origin with the lens support structure and its terminal end forming a bent arm. The bent arm can extend at least a first distance from its origin orthogonal to the lens support structure 105. The bent arm can then curve upward (anteriorly) away from the plane of the lens support structure 105 at least another distance. The bent arm 120 can then curve back towards its origin or towards the central axis CA of the device. This can result in the terminal end of the bent arm 120 lying in a different plane than the plane of the lens support structure 105. The curve or bend in the arm 120 can be projecting outward away from the central axis CA and away from both the arm's origin 103 and terminal end 102. The trans-scleral anchor 125 and/or a terminal portion of the fixation arm 120 can be positioned over or anterior to at least a portion of the lens support structure 105 or positioned over at least a portion of the central aperture 115. Alternatively, the bent arm(s) 120 can curve downward (posteriorly) away from the plane of the lens support structure 105 at least a distance and the trans-scleral anchor 125 or a terminal portion of the fixation arm 120 can be positioned under or posterior to at least a portion of the lens support structure 105 and/or under or posterior to at least a portion of the central aperture 115. The folded configuration (whether the arms 120 curve anteriorly or posteriorly) allows for at least a portion of the bent fixation arms 120 such as the terminal ends of the bent fixation arms 120 and/or their anchors 125 to be visualized through the pupil and not impeded by the opaque iris. Only one arm 120 of the fixation arms 120, two arms 120 of the fixation arms 120, or all of the fixation arms 120 can incorporate a curve.

Once the device is positioned and anchored in the eye, the fixation arms 120 are placed under tension such that the bent arm is unfurled away from this folded configuration and is no longer bent. The terminal end of the arm 120 is urged away from this resting state in which the arm 120 is in a folded configuration to urge the bent fixation arm into a straight or unfolded configuration.

The bend of the folded configuration can be a gradual, smooth bend having a radius of curvature or can bend so as to form one or more distinct angles along a length of the arm 120. The bend can be tight enough to avoid projecting too far anterior while still capable of being unfurled or placed into an unfolded configuration with relative ease without imparting undue stress on the lens support structure 105. The inward biased geometry can have a curve that is between about 0.10 mm to about 2.5 mm radius of curvature on the inner curve (anterior-facing side) and between about 0.6 mm to about 3.0 mm radius of curvature on the outer curve (posterior-facing side). In an implementation, the terminal end of the inwardly biased fixation arm can be spaced from the lens support structure 105 forming a gap G (see FIG. 17B). The gap G can be between about 0.2 mm up to about 2.5 mm. In an implementation, the biased fixation arm 120 curves a full radius of 180 degrees and has an inward biased geometry that is about 0.63 mm radius of curvature on the inner curve and about 1.13 mm on the outer curve such that the lens support structure 105 and the biased fixation arm are spaced by about 1.25 mm. The start point of the curve (near the origin 103 with the lens support structure 105) and the end point of the curve (near the terminus 102 at the trans-scleral anchor 125) can have a plurality of radiuses such that the curve changes over the length of the fixation arm 120. The curve of the biased fixation arms 120 can have an average curvature between about 0.15 mm to about 2 mm on the inner curve.

Figure 10:
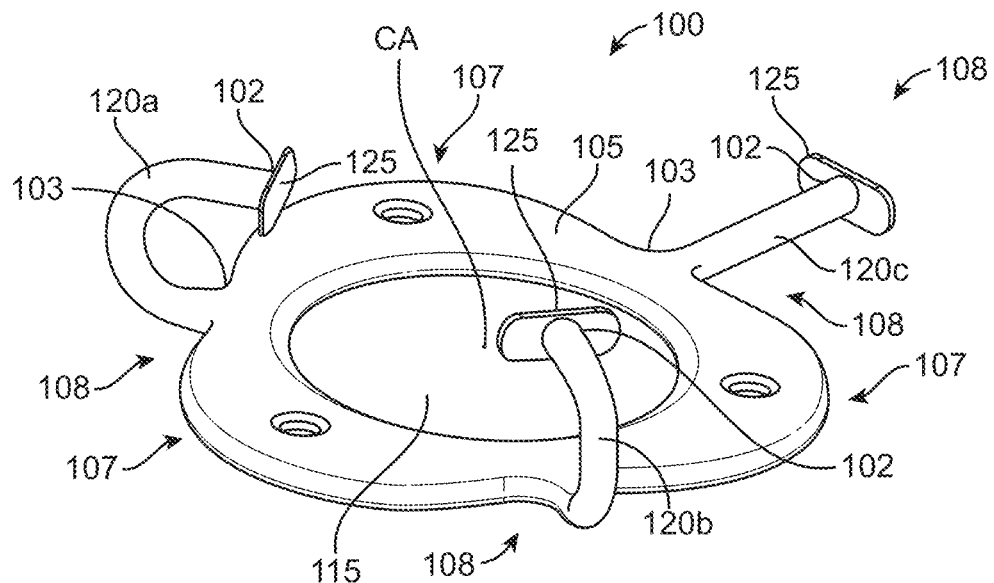
FIGS. 10 and 11 show perspective and top down views, respectively, of an implementation of a device for supporting an IOL in which two of the fixation arms are curved and inwardly biased toward a center of the device and one fixation arm is straight.
Figure 11:
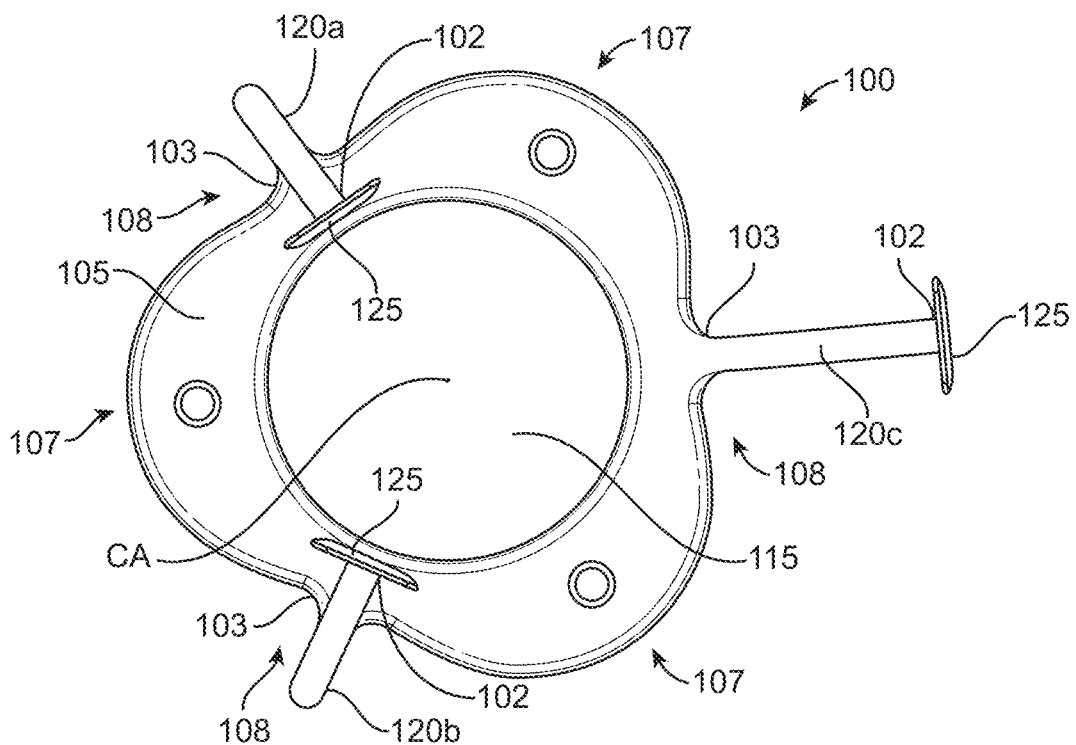
Figure 13:
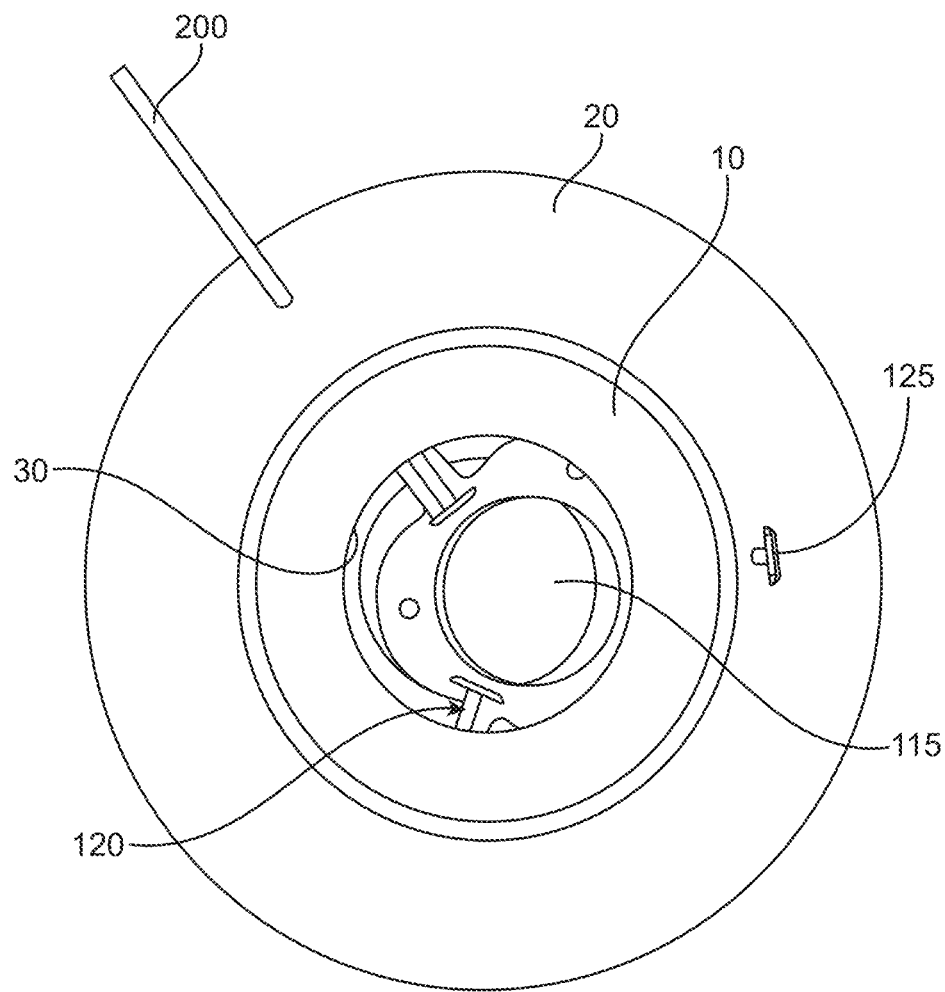
FIG. 13. shows a top down view of an eye having the device of FIG. 12 implanted.

The bent fixation arms 120, after implantation and prior to fixation with the scleral wall, can be visible through the pupil when in an unstressed (resting) state (see FIG. 13). This visibility allows the surgeon to easily engage the anchor 125. When the surgeon engages the fixation arms 120 by grabbing the body of the fixation arm 120 or anchor 125, the surgeon can unfurl the fixation arm 120 away from the resting, folded configuration in a way to bring it substantially on plane with the lens support structure 105. These fixation arms 120 can have a flexibility such that the stresses stored in the material in the deployed state will not impart torsional or tensile forces upon the lens support structure 105 in a way that compromises device function. The fixation arm(s) 120 can be molded to have a 90-270 degree turn from its lens support origin in a tangential and centripetal direction (see FIGS. 23A-23B). The fixation arm(s) 120 can incorporate elastic materials or deformable hinges to facilitate this manipulation without substantially altering the geometry of the lens support structure 105. The fixation arm 120 can have a length such that when the fixation arm 120 bends 180 degrees back towards its origin with the lens support structure 105, the terminal end 102 of the fixation arm 120 can be positioned over at least a portion of the lens support structure 105 as shown in FIGS. 10-11. Each of the fixation arms 120 of the device 100 can have a bend or just a selection of the fixation arms 120 can have a bend (e.g., one, two, up to less than all fixation arms 120). FIGS. 10-11 show two of the fixation arms 120 have a bend and one fixation arm is substantially co-planar with a plane of the lens support structure 105.

One or more of the fixation arms 120 of the devices described herein can be manufactured to have a non-planar geometry at rest and may be biased towards the folded configuration that allows for easy viewing of at least a portion of the fixation arm 120 through a pupil once the device 100 is implanted, but prior to externalization of the anchor 125. The fixation arm 120 having this configuration can be more easily grasped and manipulated by a user so that it can be urged into an unfolded configuration for sutureless fixation. A fixation arm 120 manufactured to have a bias in a resting state or that is curved or bent in a resting state includes a fixation arm 120 having that shape when the device 100 is outside the eye and ready for implantation. In some implementations, the fixation arm 120 can take on the curved, folded, or bent shape after implantation in the eye (e.g., the posterior chamber), but before fixation of the anchors. For example, one or more fixation arms 120 can be formed of a material that has a first shape outside the eye, takes on a curved shape upon implantation in the eye that is different from the shape of the arm 120 prior to implantation in the eye, and that can be unfolded into a substantially straight shape upon externalization of the anchor 125.

A fixation arm 120 that has the bias towards a folded or curved shape (e.g., having a bend along its length between its origin portion 103 and its terminal end 102) can be visualized through the pupil, grasped, and manually unfolded and/or stretched in order to fix the anchor 125 of the arm 120 trans-sclerally. The configuration and/or radius of curvature of the curve, bend, or fold as well as the directional orientation of the curve, bend, or fold can vary so long as at least a portion of the fixation arm 120 (e.g., the anchor 125 and/or the terminal end portion coupled to the anchor 125) is visible to a user through the diameter of the pupil of the patient, preferably a dilated pupil of the patient. In some implementations, this means at least a portion of the fixation arm 120 is positioned over at least a portion of the lens support structure 105 and radially inward of its outer wall 111. The distance the portion of the arm 120 extends radially inward of the outer wall 111 can vary. The portion can extend to be over a location adjacent to the outer wall 111 that is not over the outer wall 111 in the orientation a central axis CA extending anterior-to-posterior through the central opening 115. In this implementation, the distance between the central axis CA of the device to the portion extending over is greater than the distance between the central axis CA of the device and the outer wall 111. The portion can extend to be over the outer wall 111. In this implementation, the distance between the central axis CA of the device to the portion is the same as the distance between the central axis CA of the device and the outer wall 111. The portion can extend to be over a location radially inward to the outer wall 111. In this implementation, the distance between the central axis CA of the device to the portion is less than the distance between the central axis CA of the device and the outer wall 111. The portion can extend to be over the central opening 115. In this implementation, the distance between the central axis CA of the device to the portion is less than the distance between the central axis CA of the device and the inner wall 109 defining the central opening 115.

A portion of the fixation arm (e.g., the terminal end and/or the anchor 125) can be positioned over a portion of the lens support structure 105 and at the same time also over a portion of the central opening 115. For example, the anchor 125 can have a dimension such that at least a portion of the anchor 125 is positioned over at least a portion of the lens support structure 105 and another portion of the anchor 125 is positioned over at least a portion of the central opening 115.

The fixation arms 120 biased towards a curved configuration can curve towards an inner or a central portion of the device, including, but not limited to, the actual center of the device or the central axis CA. The center of the device 100 is the center of the circle formed by the central aperture 115 (in the instance where the central aperture 115 is circular). The central axis CA of the device extends through the center of that circle in an anterior-to-posterior direction (i.e., a top-to-bottom direction). If the central aperture 115 is substantially non-circular, the center of the device is a symmetrical center of the central aperture 115 along the central axis CA extending anterior-to-posterior direction. A fixation arm that is biased into a folded or curved configuration such that its anchor extends towards a center of the device or towards the central axis CA of the device need not require an axis through the anchor of the arm to intersect the actual center or intersect the central axis CA of the device. "Toward the center" or "toward the central axis" with regard to the inwardly biased fixation arms includes an arm having a curve so that the terminal end of the fixation arm extends back toward a portion of the device in a generally inward direction as opposed to the terminal end of the straight fixation arm, which extends in a generally outward direction away from the lens support structure. The curved fixation arm can be biased toward any central portion of the device and need not point directly at the actual center of the device. The curved fixation arms can be angled relative to the actual center.

Figures 22A, 22B:
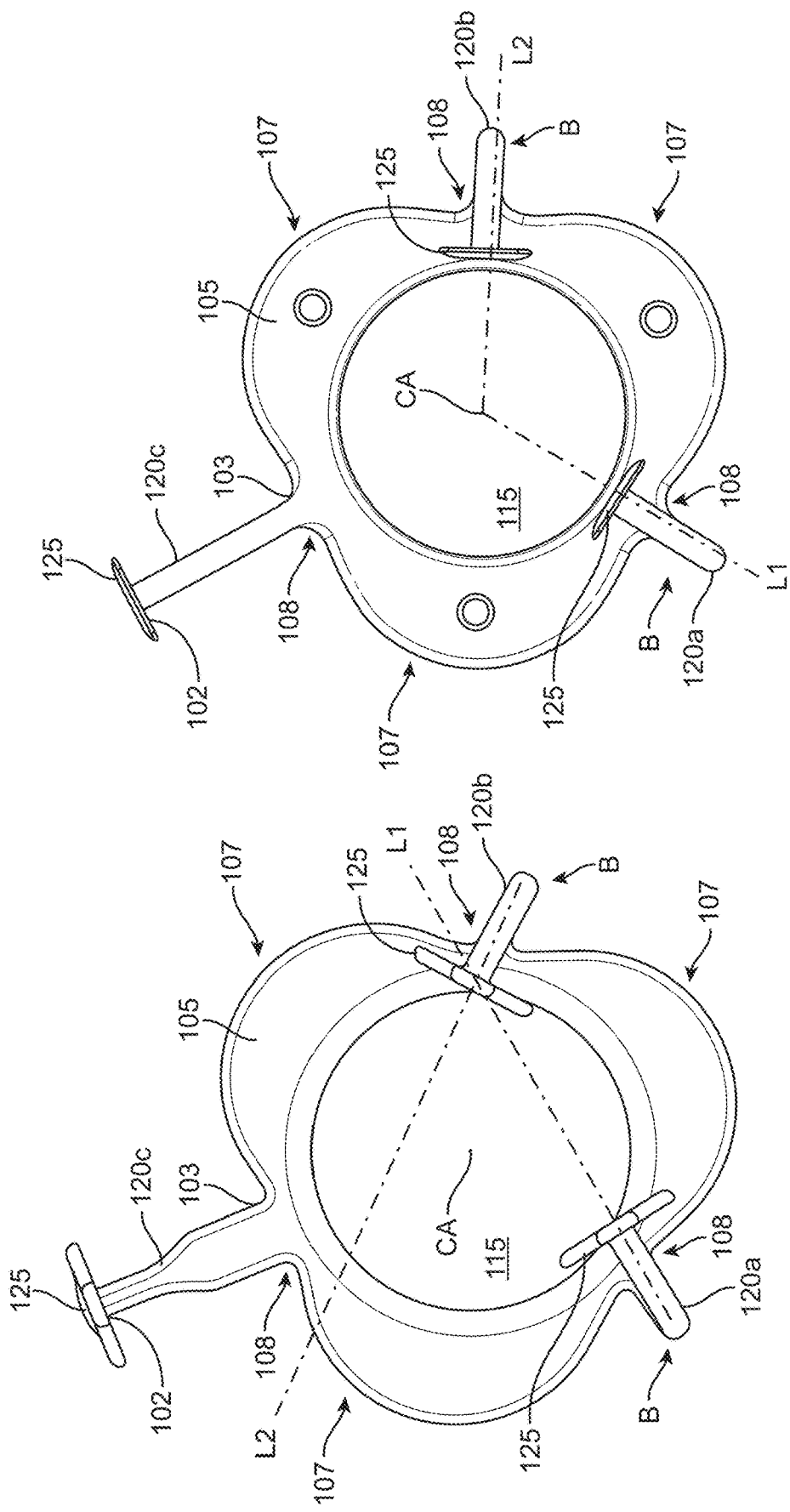
FIG. 22A shows an interrelated implementation of a device having fixation arms biased towards a folded configuration so the arm curves inwardly such that the anchor is positioned anterior to and overlapping with a portion of the lens support structure and a portion of the central opening.
FIG. 22B shows an interrelated implementation of a device having fixation arms biased towards a folded configuration so the arm curves inwardly such that the anchor is positioned anterior to and overlapping a portion of the lens support structure.

FIGS. 22A-22B and FIGS. 23A-23B illustrate implementations of the device in which at least some of the fixation arms extend back towards a center of the device. FIG. 22A shows a device 100 having a lens support structure 105 and three fixation arms 120. Two fixation arms 120a, 120b are biased into a folded configuration in which a bend B is present between the origin 103 and the terminal end 102 of the arms. The third fixation arm 120c is substantially straight and has no bend B between its origin 103 and its terminal end 102 so that it extends substantially orthogonal relative to the lens support structure 105 along a single axis. The anchor 125 of the respective fixation arms 120a, 120b project back towards a center of the device. The anchors 125 of the fixation arms 120a, 120b have at least a first portion that overlaps at least a portion of the lens support structure 105 and/or at least a second portion that overlaps at least a portion of the central opening 115 (see FIG. 22A). An axis can be drawn through the anchor 125 of each arm 120a, 120b illustrating the direction the anchor 125 is projecting away from the bend B between the arm's origin 103 and the arm's terminal end 102 and towards a center of the device. Axis L1 and axis L2 do not intersect the central axis CA. FIG. 22B shows a similar device 100 having two fixation arms 120a, 120b that are biased into a folded configuration. Each has a bend B between the origin 103 and the terminal end 102 of the arms 120a, 120b. The anchor 125 of the respective fixation arms 120a, 120b extend back toward the center of the device. Axis L1 and axis L2 intersect the central axis CA. Thus, the arms can be biased towards a folded configuration in which the anchor projects back toward a center of the device, but need not extend along an axis that intersects the central axis CA or the actual center of the device.

Where the fixation arms are described as being "folded" or "bent" or "curved" or having a configuration that is "folded" or "bent" or "curved", the angle of the fixation arms relative to a longitudinal axis along its length can change gradually and uniformly, or can change more sharply or abruptly such that an angle is formed. The folded configuration can describe the inward bias of the fixation arm at rest or prior to implantation where the fixation arm extends outward from the support structure along a first axis and curves anteriorly or posteriorly relative to a plane of the support structure back towards a central portion of the device. The support structure of the device when implanted is configured to lie substantially parallel to the Z-plane (vertical plane) of the eye. The folded configuration can include a geometry in which the fixation arm curves away from this plane of the support structure (e.g., within a transverse plane) as shown in FIGS. 22A-22B so that at least a portion of the fixation arm is positioned anterior to another portion of the device (e.g., over itself, the lens support structure, and/or the central opening). The folded configuration need not mean the fixation arm portions are over and also in contact with each other. Preferably, the portions of the fixation arm are spaced a distance away from each other, the distance being along the central axis CA of the device. The folded configuration also need not mean a creased or sharply angled folding. The folded configuration can mean a radius of curvature exists between the origin of the fixation arm at the support structure and the terminal end of the fixation arm.

Figure 23A:
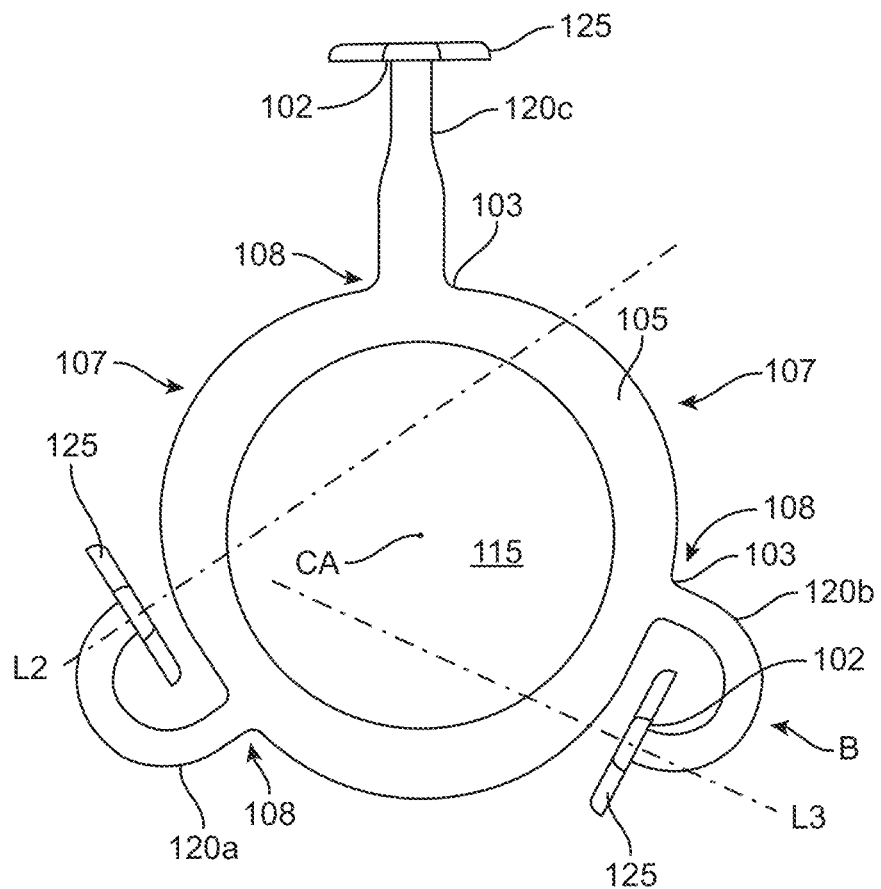
FIGS. 23A-23B show an interrelated implementation of a device having fixation arms biased towards a folded configuration so the arm curved inwardly such that the anchor remains within the plane of the lens support structure.
Figure 23B:
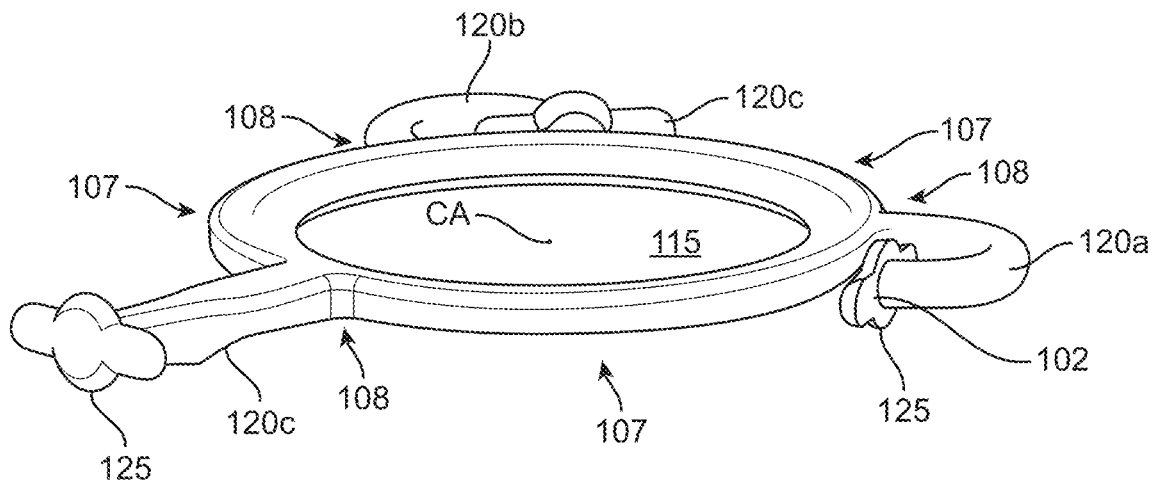

The folded configuration can also include a fixation arm that curves within the plane of the lens support structure rather than away from the plane of the lens support structure. FIGS. 23A-23B illustrate another implementation of a device 100 having a lens support structure 105 and three fixation arms 120. Two fixation arms 120a, 120b are biased into a folded configuration in which a bend B is present between the origin 103 and the terminal end 102 of the arms. The third fixation arm 120c is substantially straight and has no bend B between its origin 103 and its terminal end 102 so that it extends substantially orthogonal relative to the lens support structure 105 along an axis. The anchor 125 of the straight fixation arm 120c is projecting outwardly away from the center of the device along the axis of the arm. The anchors 125 of the respective fixation arms 120a, 120b, in contrast, are projecting inwardly from the bend B of the arm. The anchors 125 remain substantially within the same plane as the plane of the lens support structure (see FIG. 23B). An axis can be drawn through the anchor 125 of each bent arm 120a, 120b illustrating the direction the anchor 125 is projecting away from the bend B between the arm's origin 103 and the arm's terminal end 102 and towards a center of the device. The fixation arms 120a, 120b biased towards the folded configuration have anchors 125 that project towards the center of the device. Axes L1 and L2 could, but need not intersect the central axis CA. Axis L1 and axis L2 shown in FIG. 23A extend towards the center, but do not intersect the central axis CA.

A portion of the arm 120 that is positioned over at least a portion of the support structure 105 can include that portion being over as well as positioned radially inward of an outer wall 110 of the support structure 105. The portion of the arm 120 that is positioned over at least a portion of the support structure 105 can include that portion being positioned radially inward of and over the central opening 115. In these instances, "radially inward" need not also mean within the same plane. Preferably, the portion of the arm 120 is positioned over the portion of the support structure within a different plane from the plane of the support structure. The portion of the fixation arm 120 (e.g., anchor 125 and/or terminal end 102) can terminate anterior or posterior to the lens support structure 105 at a diameter that is central to the outer perimeter of the lens support structure 105. The portion can be located over the portion of the lens support structure relative to the central axis CA of the device that extends anterior-to-posterior through the central opening 115. Where the portion of the fixation arm 120 is described as being over the portion of the lens support structure, the portion of the fixation arm 120 may also be over the central opening 115 defined by the lens support structure 105.

Where a portion of the arm 120 is described herein as being "over" another portion of the device 100 (e.g., itself, the lens support structure 105, and/or the central opening 115), the portion of the arm 120 can generally overlap that portion of the device in space and need not require a particular direction relative to the retina. Thus, "over" may be used generically herein to refer to an overlap in the space surrounding the device and can, but need not require the spatial overlap to be in a generally anterior direction relative to the retina. A portion that is described as being "over" another portion can, during use, be positioned posterior to it relative to the retina. The arm 120 that is biased into the folded configuration may only be referred to herein as "over" or "overlapping" another part of the device even though it may also, during use, be positioned "under" or "posterior" to another part of the device relative to the retina. For the sake of simplicity, each alternative may not be reiterated at each instance throughout the disclosure. The arms can be curved to position at least a portion of the arm over an anterior-facing portion of the device such that the portion is generally vaulted above the device along the central axis CA. The arms can be curved to position at least a portion of the arm over a posterior-facing portion of the device such that the portion is generally vaulted below the device along the central axis CA. The arms can be curved to position at least a portion of the arm within the same plane so that it is neither over the anterior-facing portion nor over the posterior-facing portion of the device. Any of a variety of configurations of the fixation arms are considered herein so that at least a portion of the arms are visible through a dilated pupil. The mechanisms can vary by which the bent fixation arms 120 that are biased towards the folded configuration become unfolded to take on a straight configuration. The arms can be unfolded mechanically, electromagnetically, and/or thermally.

In some implementations, the fixation arm 120 may be unfolded mechanically along a single axis of the arm. The fixation arm 120, at rest, need not be biased into a folded configuration that has a bend or that curves. For example, the fixation arm 120 may be biased into a folded configuration in which the arm 120 is compressed longitudinally along a single axis. The arm 120 be extend along the single axis orthogonally outward from the lens support structure between its origin portion 103 and its terminal end portion 102. The length of the arm 120 in the folded configuration can be shorter between origin portion 103 and terminal end portion 102 such that the anchor 125 of the arm 120 is positioned more centrally within a smaller diameter than when in the unfolded configuration. Once the device is implanted in the eye, but before externalization of the anchor 125, the arm 120 may be telescoped outward to extend its length such that it can be externalized. The mechanical unfolding by telescoping can be due to nested components of the arm 120 sliding over each other to provide greater length when unfolded or a shorter length when folded. The mechanical unfolding by telescoping can also be due to a single elastic component configured to fold into itself for a shorter length for visualizing through the pupil and unfold out of itself for a longer length during externalization.

In some implementations, the fixation arm 120 may be unfolded or folded thermally. For example, the fixation arm 120 can be in a first shape at room temperature (folded or straight) and change to a second shape at body temperature or thereabouts (heated to 35° C.). This can also be effected by chemical means (e.g., hydration) or mechanical means (cutting a restrictive feature).

The fixation arm 120 can be produced from elastic or inelastic material. For example, the fixation arm 120 can be formed of an inelastic material and have a 3-dimensional shape that provides for the elasticity. The 3-dimensional shape can vary as described elsewhere herein, including a C-shape, Z-shape, S-shape, or other 3-dimensional shape. The fixation arm 120 provides sufficient support to maintain an IOL 110 or other device while not imparting excessive force on scleral tissue. An optimal design would have a wide operable range of tensions and stability in order to be able to meet both parameters in eyes of varying sizes and with incisions in varying locations. One means of modifying the fixation arm design is to incorporate spring-like structures. These can include traditional compression based haptic designs like J-Loop, C-Loop, Closed Loop, Kellman Haptics, plate haptics, or other haptic designs common to IOLs. Alternatively, the device 100 can incorporate a tension-based haptic such as a simple linear elastic cord. Alternatively, the tension design can be modified with a V-shaped, Z-shaped or S-shaped feature to decrease the tensile resistance of the fixation arm 120.

The fixation arm 120 can have a texture or features that allows it to be pulled through sclera in one direction, but there is resistance in the opposite direction to minimize the chance of slippage the fixation arm 120. The texture or feature can be provided by the material itself or designed into the fixation arm 120. For example, the fixation arm 120 can be barbed and formed from a material integrated into an outer structure. In this way, a barbed internal structure may be able to function as a barb while hiding the sharp edges commonly associated with a barb. An example would be a rigid plastic structure embedded in a soft elastomeric structure.

The fixation arms 120 can be formed of a flexible material that has memory and is not malleable. The flexible material of the fixation arms 120 can include any of a variety of elastomers including polyurethanes, hydrophobic acrylics, hydrophilic acrylics, Nylon, Polyimide, PVDF, natural polyisoprene, cis-1,4-polyisoprene natural rubber (NR), trans-1, 4-polyisoprene gutta-percha, synthetic polyisoprene (IR for isoprene rubber), Polybutadiene (BR for butadiene rubber) Chloroprene rubber (CR), polychloroprene, Neoprene, Baypren etc., Butyl rubber (copolymer of isobutylene and isoprene, IIR), Halogenated butyl rubbers (chloro butyl rubber: CIIR, bromo butyl rubber: BIIR), Styrene-butadiene Rubber (copolymer of styrene and butadiene, SBR), Nitrile rubber (copolymer of butadiene and acrylonitrile, NBR), also called Buna N rubbers Hydrogenated Nitrile Rubbers (HNBR) Therban and Zetpol, EPM (ethylene propylene rubber, a copolymer of ethylene and propylene) and EPDM rubber (ethylene propylene diene rubber, a terpolymer of ethylene, propylene and a diene-component), Epichlorohydrin rubber (ECO), Polyacrylic rubber (ACM, ABR), Silicone rubber (SI, Q, VMQ), Fluorosilicone Rubber (FVMQ), Fluoroelastomers (FKM, and FEPM) Viton, Tecnoflon, Fluorel, Aflas and Dai-El, Perfluoroelastomers (FFKM) Tecnoflon PFR, Kalrez, Chemraz, Perlast, Polyether block amides (PEBA), Chlorosulfonated polyethylene (CSM), (Hypalon), Ethylene-vinyl acetate (EVA), Thermoplastic elastomers (TPE), resilin and elastin, Polysulfide rubber, and Elastolefin.

The arms 120 made of a flexible material that is formed into a shape can be flexed away from the formed shape, but has memory to return to the formed shape. In other words, the flexible fixation arms 120 can be flexed or unfolded away from their folded configuration, but cannot be urged into a different shape that is retained without some kind of anchoring fixation. For example, one or more of the flexible fixation arms 120 can be formed into a bent shape. For example, the arm can include a 180 degree bend from its origin 103 with the support structure 105 to the terminal end 102 near the anchor 125. The arm 120 can maintain this bent shape when the device is at rest and no forces are applied to the arm 120 such that the arm 120 is biased towards a folded configuration. In other words, the arm 120 in its unbiased state is bent. The bent fixation arm 120 can be flexed away from this bent shape to take on a straight shape or an unfolded configuration such that the entire arm 120 extends and is positioned straight relative to the longitudinal axis L. When flexed into a straight shape, the arm 120 is biased to return to the bent shape or the folded configuration. If the flexing force on the fixation arm 120 is released, the arm 120 will return to its resting bent shape. However, when in use, the fixation arm 120 is anchored trans-sclerally and the anchor 125 at the terminal end 102 of the arm 120 positioned outside the sclera. The arm 120 is tensioned to remain in the straight shape.

In other implementations, the fixation arms 120 can be formed of or incorporate a material that is malleable such that the fixation arms 120 can be bent or formed into a particular shape. The malleable fixation arms 120 can be formed of a material such as implant-grade metals or plastics including gold, silver, platinum, stainless steel, Nitinol, nickel, titanium, polypropylene, polyethylene, nylon, PVDF, polyimide, Acetal, and PEEK.

The one or more fixation arms 120 can have a Young's modulus that is less than about 1000 MPa, or less than about 500 MPa, or less than about 250 MPa, or less than about 100

MPa, or less than about 50 MPa, or less than about 25 MPa. The one or more fixation arms 120 can have a Young's modulus that is less than about 20 MPa, for example, between about 0.01-about 1.0 MPa. The fixation arms 120 can be very soft and apply very little force because they are designed to be under tension to anchor the support structure 105 rather than having a spring force to anchor the support structure 105 or a more rigid penetrating force that a barb or other fixation haptic can provide.

In some implementations, the fixation arms 120 can each have a length between the origin 103 and the terminal end 102 that is about 2 mm to about 6 mm. The fixation arms 120 each can have the same length. The length of the fixation arms 120 that extends through the sclera can having a thickness or width that is minimized to reduce the overall size of the wound through which the arms 120 extend. The maximum width of the trans-scleral portion of the fixation arms near the terminal end 120 where the anchor 125 is positioned can be no greater than about 2.0 mm, no greater than about 1.5 mm, no greater than about 1.0 mm, no greater than 0.75 mm, no greater than 0.50 mm.

Figure 12:
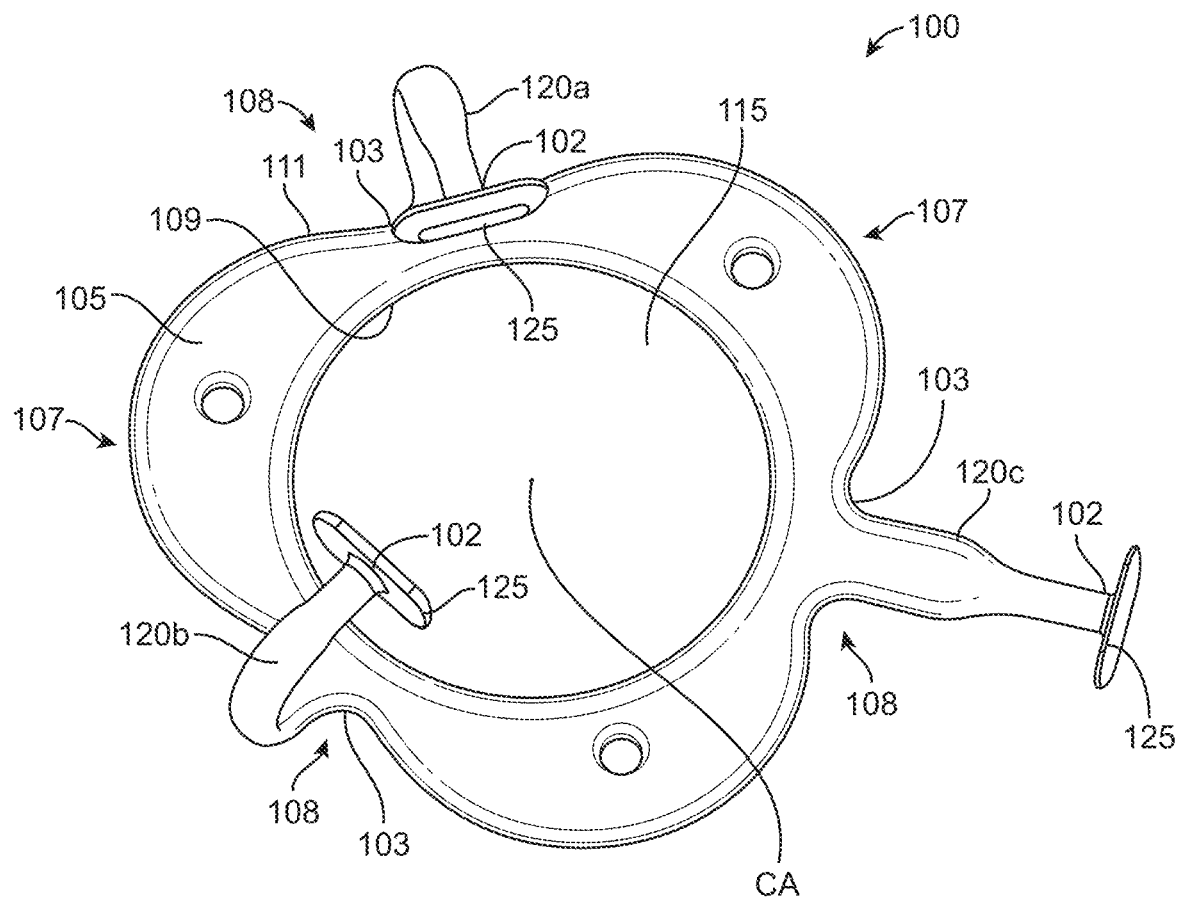
FIG. 12 shows an implementation of a device for supporting an IOL in which two fixation arms are curved and inwardly biased toward a center of the device and one fixation arm is straight and has a geometry that makes it more rigid than the other fixation arms.

FIG. 12 also shows an implementation of a device 100 having two fixation arms 120a, 120b that have inward bias and a third fixation arm 120c that does not have inward bias and is straight. Additionally, the third fixation arm 120c has a geometry that makes it less flexible than the other fixation arms 120a, 120b. The third fixation arm 120c can incorporate a region between the origin 103 and terminal end 102 that is wider than the other two fixation arms 120a, 120b and can have a higher cross-sectional area. FIG. 8B also shows a region of a fixation arm 120 that is wider. A width W1 of the arm 120 near the terminal end 102 can be less than a width W2 of the arm 120 away from the terminal end 102 of the arm 120. The width W2 of the arm 120 away from the terminal end 102 can provide a degree of bulk and stability while the width W1 near the terminal end 102 can minimize the trans-scleral portion of the arm 120.

Figure 17A:
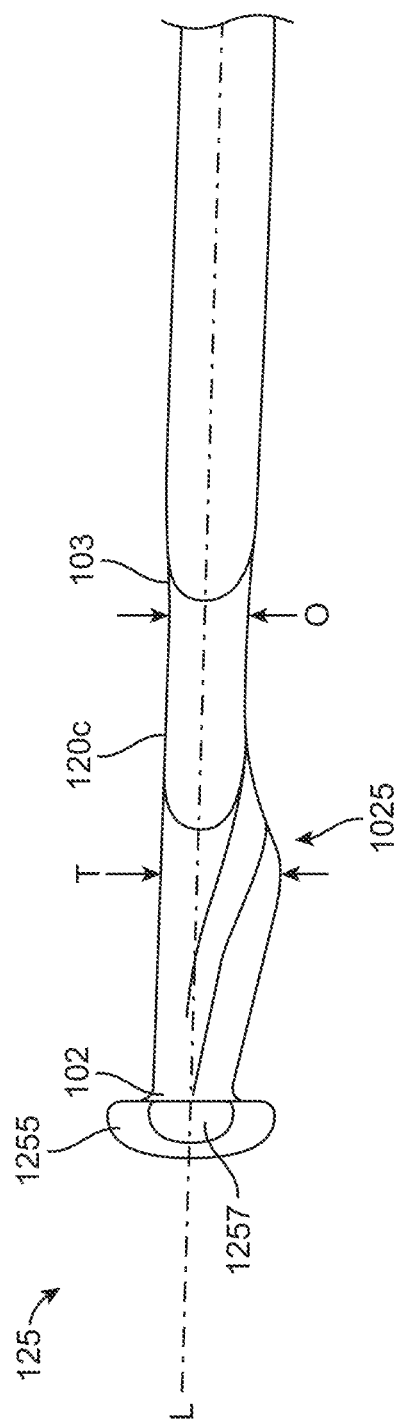
FIGS. 17A-17B shows a straight, leading fixation arm designed to bias the device anteriorly to prevent posterior drift during anchoring footplate externalization.
Figure 17B:
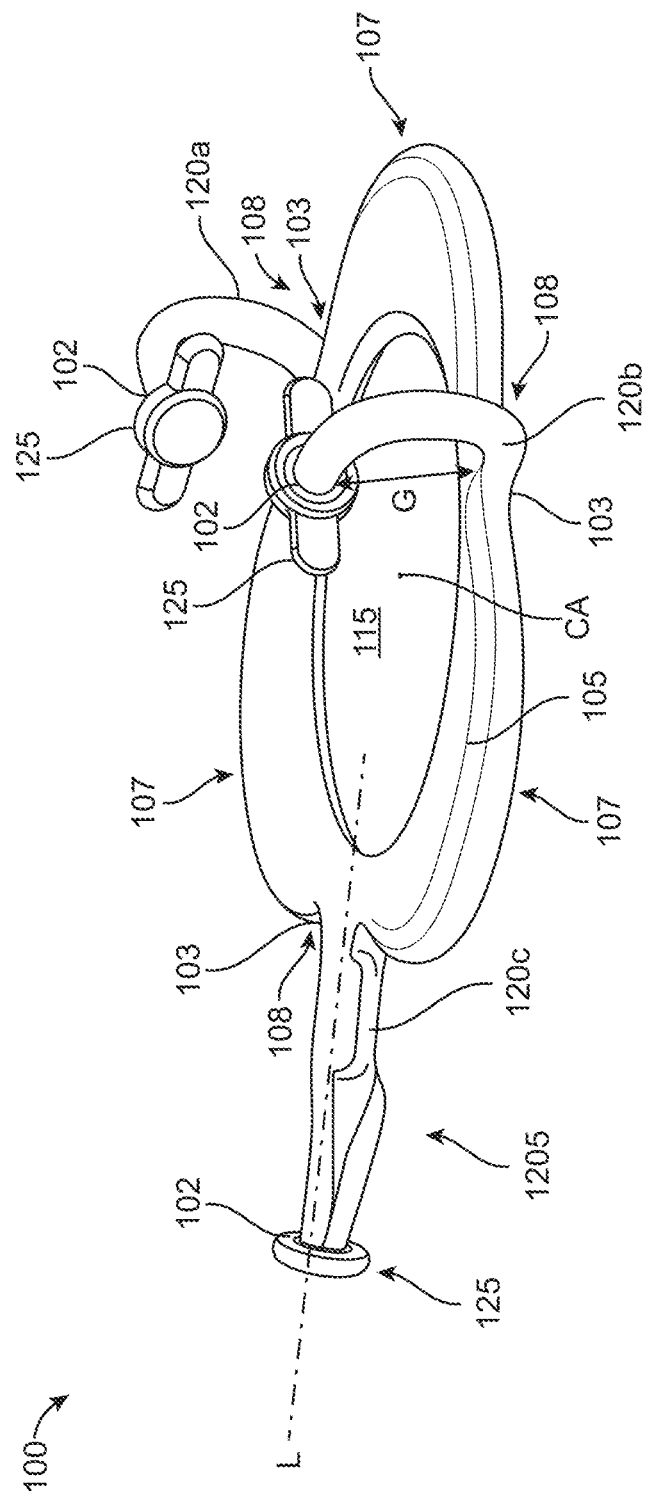

Each fixation arm 120a, 120b, 120c can be positioned one at a time during the surgical procedure. As described elsewhere herein, the leading fixation arm 120c can be a straight configuration and the trailing fixation arms 120a, 120b can be curved (see FIGS. 17A-17D). The weight of the device can cause the first implanted or leading fixation arm 120c to bend following externalization such that the device 100 tilts posteriorly toward the retina. In this scenario, a surgeon can locate the device in a more posterior position. However, this can increase the risk of intraoperative tissue damage due to the manipulation of tools near the retina. In some implementations, the leading fixation arm 120c can be mechanically and/or geometrically reinforced to reduce the likelihood of posterior drift. The leading fixation arm 120c can be produced out of a material that is resistant to such deformation. The material can be any implant grade plastic or metal that can cantilever the device following externalization of the anchor 125 of the leading fixation arm 120c. Suitable materials include, but are not limited to, PMMA, rigid silicones, nylon, hydrophilic and hydrophobic acrylics, PEEK, polyimide, stainless steel, titanium, Nitinol, and others. The more rigid material can be used to form the entire leading fixation arm 120c or just a portion of the leading fixation arm 120c. The leading fixation arm 120c may be formed of a softer material embedded with a more rigid material. In an implementation, the leading fixation arm 120c can include a region 1205 of mechanical reinforcement between its origin 103 at the support structure 105 and its terminal end 102 where it is coupled to an anchor 125 (see FIG. 17A). The region 1205 can achieved by increasing a thickness of the fixation arm 120c or embedding a rigid section of plastic into a softer material. FIG. 17A shows an increased thickness (arrows T) at the mechanical reinforcement region 1205 compared to a thickness (arrows O) of the arm near its origin 103 with the support structure. The region 1205 can be spaced a distance away from the support 105, for example, close to or adjacent the anchor 125. The region 1205 can have an increased thickness (see FIGS. 17A-17D) designed to specifically reduce the likelihood that the device 100 drifts posteriorly, while not impacting the ability externalizing the anchor 125 of the fixation arm 120. For example, the fixation arm 120 can have a tapered thickness designed to limit deflection in the posterior direction. The tapered geometry can be thinnest near the footplate anchor 125 and thicken centrally. The posterior surface of the fixation can serve to bias the device anteriorly relative to the eye. The angle of contact of the posterior surface of the fixation arm 120 and the wound can bias the device 100 in a way that reduces the practical risk of a posterior deflection of the fixation arm 120. Additional bulk can further limit the deflection of the device and the proximity to the retina.

The trans-scleral fixation arm 120 and/or anchor 125 can have a photoreactive or hydroreactive element that assists in the sizing or fixation of the fixation arm. By swelling or shrinking a portion of the fixation arm, the geometry of the fixation arm can be expanded or contracted in order to intra-operatively or post-operatively adjust the length of the fixation arm. Alternatively, by expanding the anchor following the externalization of the fixation arm, the anchor will become more effective in providing secure fixation with reduced risk of slippage.

The cross anchor of the fixation arm is able to slide along the fixation arm 120 with some resistance. By adjusting the fixation arm 120 intraoperatively, the surgeon can size the device 100 specifically for a given patient. Custom sizing reduces the risk of slippage and modulation of the effective lens position. Once the fixation arm 120 is set to the appropriate tension, the excess material can be removed such as by trimming.

The device 100 can be made of a material or contain a geometry that can serve as a drug delivery device, including a refillable drug delivery device. A securely fixated device accessible in the subconjunctival space would provide an opportunity to deliver drugs to the posterior and anterior segments. Examples of therapeutics can include one or more drugs for lowering intraocular pressure (glaucoma medications), steroids, biologic medications such as anti-vascular endothelial growth factor (anti-VEGF), gene therapy, antibacterial, anti-viral, chemotherapeutic, and non-steroidal anti-inflammatory medications, among others to treat ocular or systemic diseases.

The device 100 can contain a structure within which an IOL haptic 114 can be fixed. In some circumstances, the IOL haptics 114 can be secured in the sulcus. However, it may be advantageous to provide a location for haptic fixation within the device itself. The structure of the device 100 can be one or more pockets on the inner wall 109 of the lens support structure 105 that are sized and shaped to receive the IOL haptics 114. Alternatively, the anterior or posterior surface of the device 100 can contain a slot or clasp that can receive and fix the IOL haptic 114 in place. The lens support structure 105 can have one or more holes through which the IOL haptic 114 can be passed. Alternatively, the haptic geometry may be designed such that the IOL haptic 114 can be wrapped around one or more of the fixation arms 120. The fixation arms 120 can also have a hole through which the IOL haptic 114 can be passed.

The device 100 may be designed to host any form of intraocular lens 110 with any haptic design and any optical design. The device 100 may be designed to fit a specific IOL design with a geometry specifically designed to mate with the lens support structure 105. The design may be specifically suited to allow for the exchange of lenses. The lens support structure 105 may be manufactured with an integrated lens 110 providing refractive correction. The correction can include but is not limited to monofocal, extended depth of focus, accommodating, light adjustable, multipiece/exchangable or multifocal IOL optics.

The devices described herein can be used together with IOLs having any of a variety conventional designs, including multi-piece as well as one-piece designs. IOL 110 can include a central optic 112 and two haptics 114 (see, e.g., FIGS. 19B-19C, 20B-20C, 24B, 24C, 24F, 25B, 25C, 26B, 26C, and 26E). The haptics 114 can be conventional open loop haptics such as C-loop, J-loop, modified J-loop, or other haptics. The IOL 110 may be positioned above (or below) the central opening 115 of the device so that the central axis CA extending anterior-to-posterior through the central opening 115 extends through the optic 112 of the IOL 110. The haptics 114 of the IOL 110 may project upwards or anteriorly away from (or toward, if positioned below) the lens support structure 105 as described elsewhere herein. One-piece IOLs can have open loop haptics similar to conventional three-piece IOLs do. One-piece IOLs may also incorporate monobloc-plate style haptics. Where the device is shown with one type of IOL (e.g., the multi-piece IOLs shown in FIGS. 19B-19C and 20B-20C or the one-piece IOL shown in FIGS. 24B, 24C, 24F, 25B, 25C, 26B, 26C, and 26E), it should be appreciated that another type of IOL can be mated with the device. The devices described herein can be used with any type of IOL as described elsewhere herein, including multi-piece as well as one-piece designs. Similarly, the haptics of the IOL can be of any of a variety of configurations.

The lens support structure 105 can have a geometry adapted to mate with a perimeter of the IOL or with one or more haptics of the IOL. The geometry can include a concavity, recess, channel, or groove forming at least a portion of an inner perimeter of the lens support structure.

FIGS. 24A-24F, 25A-25C, and 26A-26E illustrate various implementations of a device configured to mate with an IOL such that at least a portion of the IOL is covered by at least a portion of an internal surface of the device.

Figure 24A:
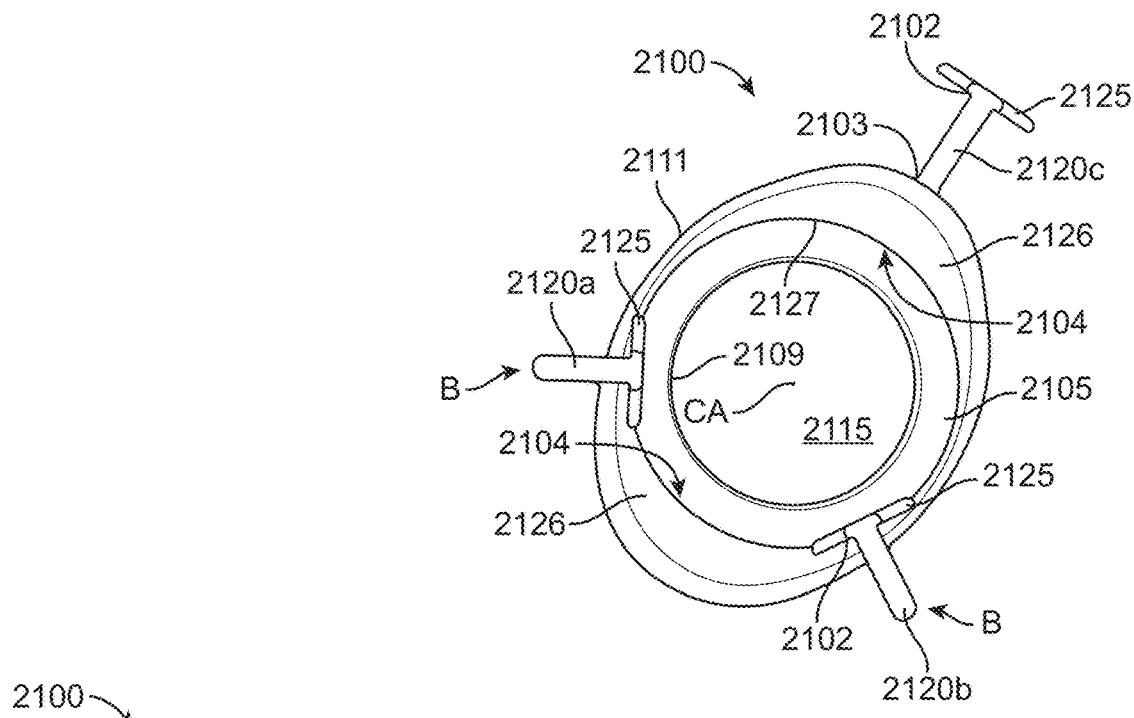
FIGS. 24A-24F show an interrelated implementation of a device having awnings configured to accommodate an IOL.
Figure 24B:
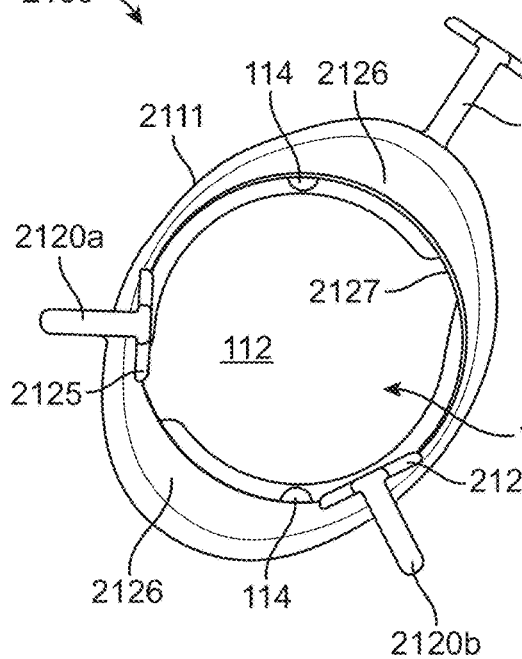
Figure 24C:
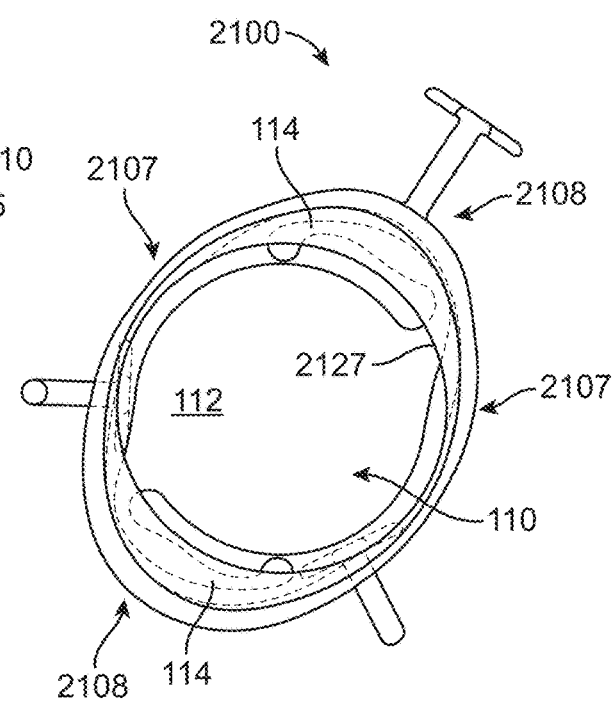
Figure 24D:
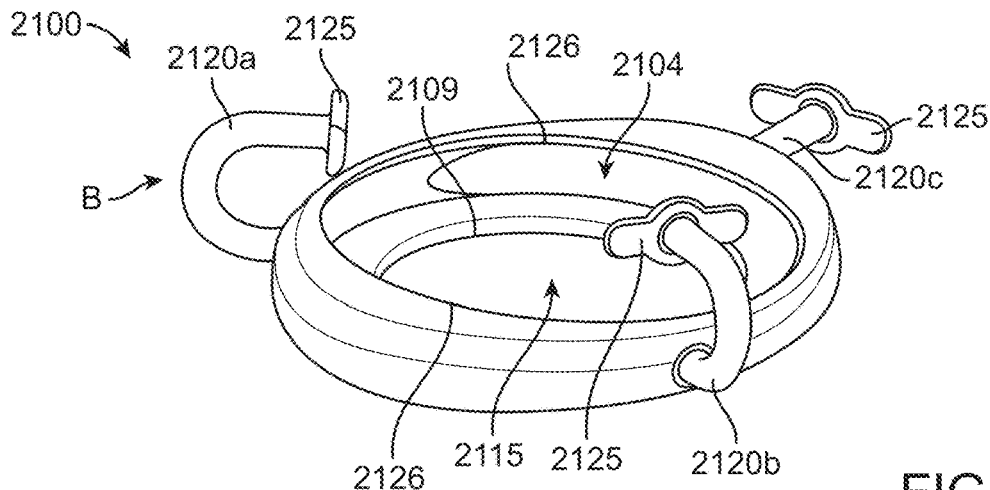
Figure 24E:
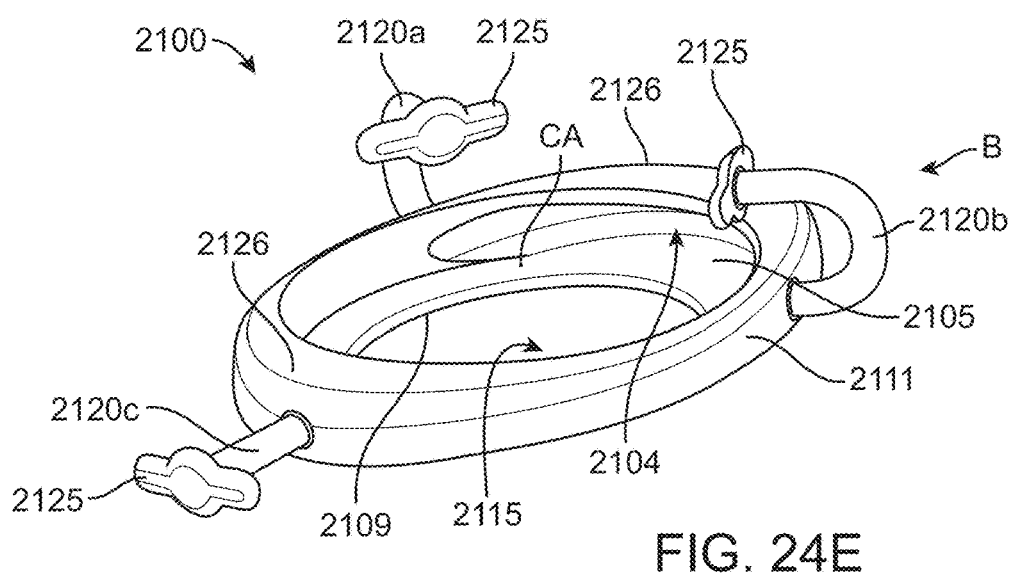
Figure 24F:
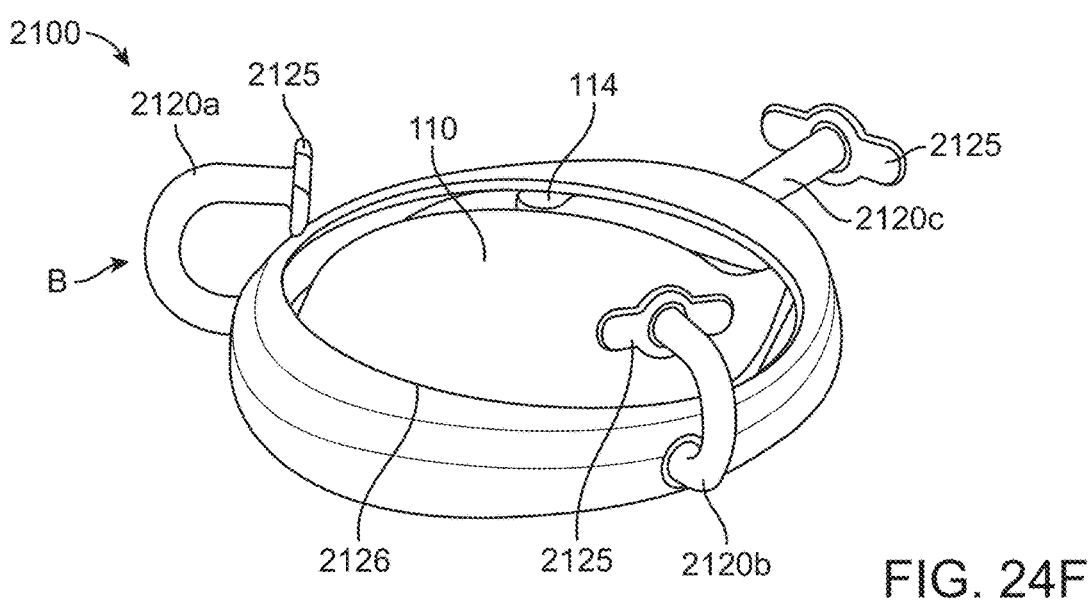
Figure 26A:
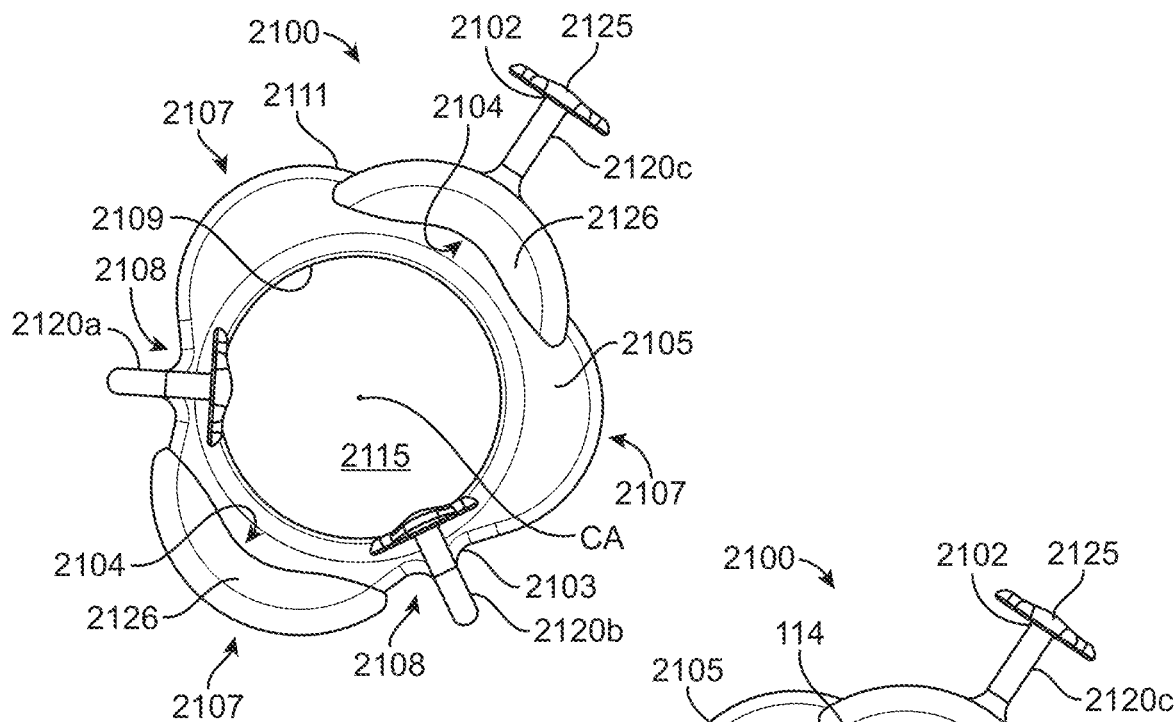
FIGS. 26A-26E show another implementation of a device having awnings configured to accommodate an IOL.
Figure 26B:
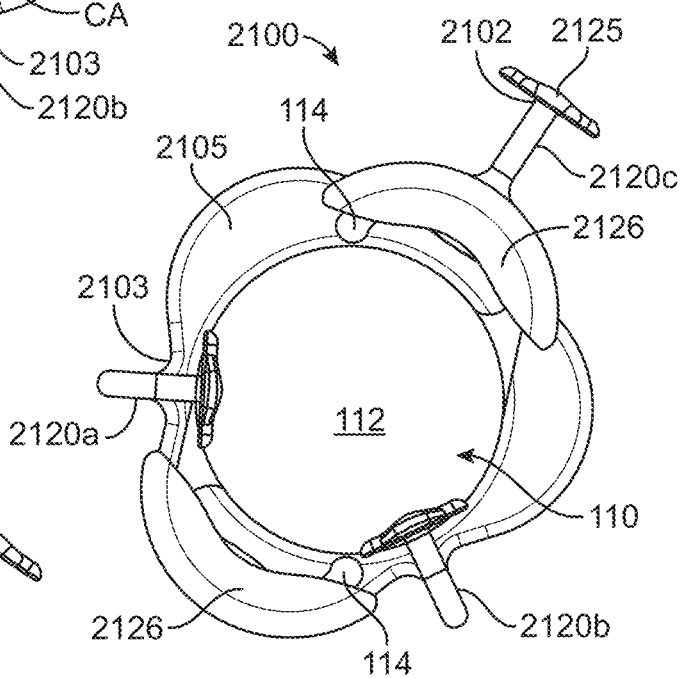
Figure 26C:
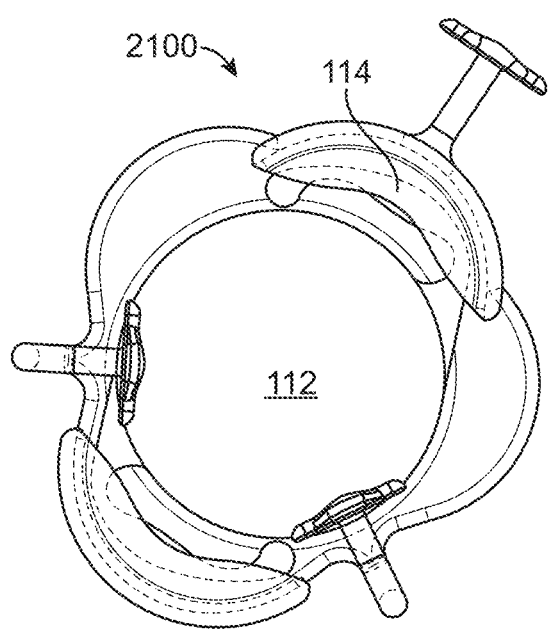
Figure 26D:
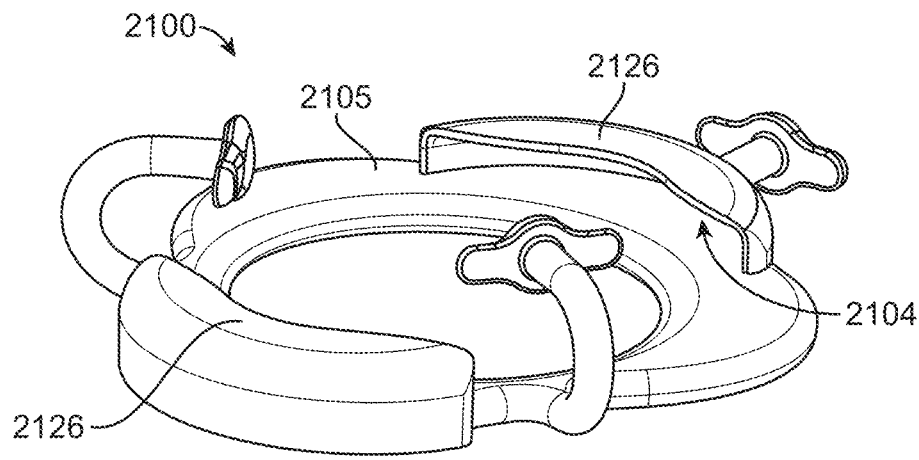
Figure 26E:
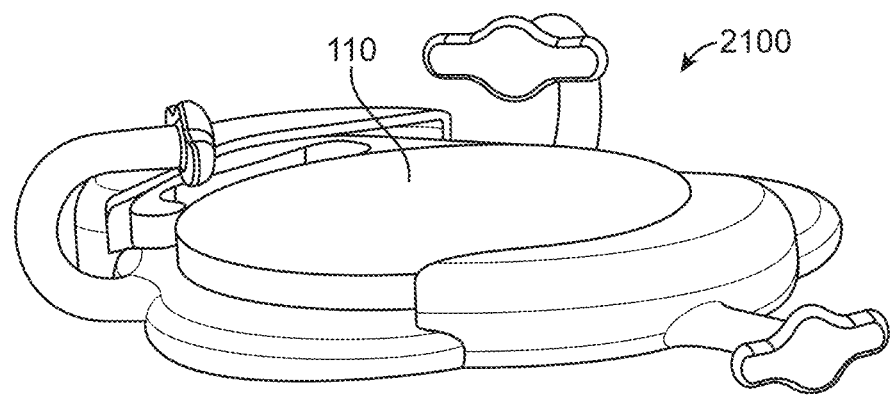

FIGS. 24A-24F illustrate an implementation of a device 2100 having a lens support structure 2105, a central aperture 2115, and a plurality of fixation arms 2120. The central aperture 2115 can be bound by the inner perimeter or inner wall 2109 of the lens support structure 2105. The central aperture 2115 can be circular, but the outer perimeter or outer wall 2111 of the lens support structure 2105 can be non-circular. As described elsewhere herein the outer perimeter of the lens support structure 2105 can have any of a variety of shapes including circular, non-circular, oval, elliptical, rounded rectangle (FIGS. 25A-25C), rounded triangle (FIGS. 26A-26E), etc. The lens support structure 2105 can support the IOL 110, for example, taking the place of a native lenticular capsular bag. The device 2100 can include one or more leaflets or awnings 2126 positioned over an anterior-facing surface of the lens support structure 2105 so that one or more recesses 2104 are formed within which at least a portion of the IOL 110 may be positioned. The recesses 2104 may at least partially surround the central aperture 2115 and be sized to accommodate at least a portion of the IOL, such as the haptics 114. FIGS. 24B, 24C, and 24F show the IOL 110 engaged with the device 2100. The optic 112 of the IOL 110 is positioned over the central opening 2115 and a perimeter region of a posterior-facing surface of the optic 112 is positioned against the anterior-facing surface of the lens support structure 2105. Each of the haptics 114 of the IOL 110 can be positioned substantially within the respective recesses 2104 and a majority of the optic 112 of the IOL 110 remains outside the recesses 2104. The recesses 2104 can be defined by an anterior-facing surface of the lens support structure 2105 and the overhanging leaflet or awning 2126. The volume of the recesses 2104 formed by the space between the anterior-facing surface of the lens support structure 2105 and the posterior-facing surface of the awning 2126 is sufficient to receive the respective one of the haptics 114 in both depth anterior-to-posterior as well as distance away from the central axis CA of the opening 2115. The awnings 2126 can have a smooth geometry and can serve to protect the iris from any sharp edges of the IOL once positioned on the device 2100. Additionally, the central-facing surfaces of the awnings 2126 (facing toward a center axis CA of the device 2100) can additionally serve to provide a surface against which the haptics 114 may abut. These surfaces can provide counter pressure to the haptics and thereby aid in centering the IOL 110 on the device 2100. The awnings 2126 also can limit Z-axis movement of the haptics 114 and help to secure the IOL 110 to the device 2100. The reliable fixation of the IOL, including one-piece IOLs, allow for the use of IOLs that require tight centration tolerances (e.g., torics, multi-focal lenses, extended depth of focus (EDOF) IOLs, and accommodating IOLs).

The IOL 110 may be positioned within the device 2100 prior to implantation in the eye or after implantation in the eye. Similarly, the IOL 110 may be removed from the device 2100 and replaced postoperatively.

FIGS. 24A-24F illustrate an implementation of the device 2100 having an outer perimeter 2111 that is substantially oval in shape having a major axis and a minor axis. Thus, the inner perimeter 2109 may define a circular central aperture 2115 and the outer perimeter 2111 may define a non-circular shape. The recesses 2104 formed by the awnings 2126 are positioned opposite one another relative to the major axis so that the span of the IOL 110 haptics 114 may be accommodated within the recesses 2104.

FIGS. 25A-25C illustrate another implementation of a device 2100 having a circular central aperture 2115 and a non-circular outer perimeter 2111. The non-circular outer perimeter 2111 in FIGS. 25A-25C is a rounded rectangle shape having two substantially flat, elongate sides 2108 and two substantially rounded, short sides or lobes 2107. The recesses 2104 formed by the awnings 2126 may project out over the anterior-facing surface of the lens support structure 2105 such that they are positioned generally opposite one another along a major axis of the rectangle and spaced to accommodate the span of the IOL 110 haptics 114. For example, the awnings 2126 may project out over the anterior-facing surface of the lens support structure 2105 on the short sides of the rounded rectangle (i.e., at the location of the lobes 2107) to accommodate the span of the IOL therebetween within the recesses 2104 along the long sides 2108.

Three fixation arms 2120 can be coupled to the lens support structure 2105. At least one of the fixation arm 2120a, 2120b can be biased into the folded configuration as described elsewhere herein. One fixation arm 2120c can be a leading fixation arm that extends along a single axis orthogonally relative to the lens support structure 2105 so that its terminal end 2102 coupled to the anchor 2125 projects outward away from the center axis CA of the aperture 2115. The leading fixation arm 2120c can be coupled to the lens support structure 2105 at a location of a lobe 2107 and the other fixation arms 2120a, 2120b can be coupled away from the lobe 2107 of the leading fixation arm, for example, on opposite sides 2108 so that the opposite lobe 2107 projects outward between the arms 2120a, 2120b (see FIGS. 25A-25B).

FIGS. 26A-26E illustrate another implementation of a device 2100 having a circular central aperture 2115 and a non-circular outer perimeter 2111. The non-circular shape of the outer perimeter 2111 may be a rounded triangle shape having a plurality of lobes 2107 projecting outward from a plurality of sides 2108 as described elsewhere herein. Each of the three fixation arms 2120 can extend outward from a respective one of the plurality of sides 2108. The awnings 2126 may project out over the anterior-facing surface of the lens support structure 2105 such that they are positioned generally opposite one another. A first awning 2126 may be positioned on a side 2108 near, for example, an origin 2103 of the leading fixation arm 2120c and a second awning 2126 may be positioned on a lobe 2107 between the other two fixation arms 2120a, 2120b (see FIGS. 26A-26B). The arrangement of the awnings 2126 relative to one another can be rotated so that the first awning 2126 may be positioned on a lobe 2107 adjacent the origin 2103 of the leading fixation arm 2120c and the second awning 2126 may be positioned on a side 2108 near an origin 2103 of one of the curved fixation arms 2120a, 2102b. Regardless the orientation, the span of the recesses 2104 defined by the awnings 2126 and the lens support structure 2105 is sufficient to accommodate a span of the IOL haptics 114 therebetween (see FIG. 26C).

The central opening 2115 may have a diameter as described elsewhere herein so that the optic 112 of the IOL may be supported on the anterior-facing surface of the lens support structure 2105 without the optic 112 slipping through its diameter (e.g., between about 4 mm up to about 6 mm). The IOL may be inserted within the recesses 2104 under the awnings 2126. Thus, the diameter between the first and second opposing awnings 2126 is sufficient for IOL insertion. IOLs are typically foldable and therefore the diameter between the first and second awnings 2126 can vary widely. In some implementations, the opposing awnings 2126 are fully connected to one another along the sides 2108 (see FIG. 24C). The opposing awnings 2126 can include extensions along each of the sides 2108 forming a complete overhanging surface above the lens support structure 2105 that defines an upper aperture 2127. The upper aperture 2127 can have a diameter that is larger than a diameter of the central aperture 2115 of the lens support structure 2105. For example, the upper aperture 2127 can be greater than about 6 mm so that the IOL can be manipulated into place and fully unfurl into position with the recesses 2104. The diameter of the upper aperture 2127 can be greater than 6 mm up to about 8 mm.

Figure 27:
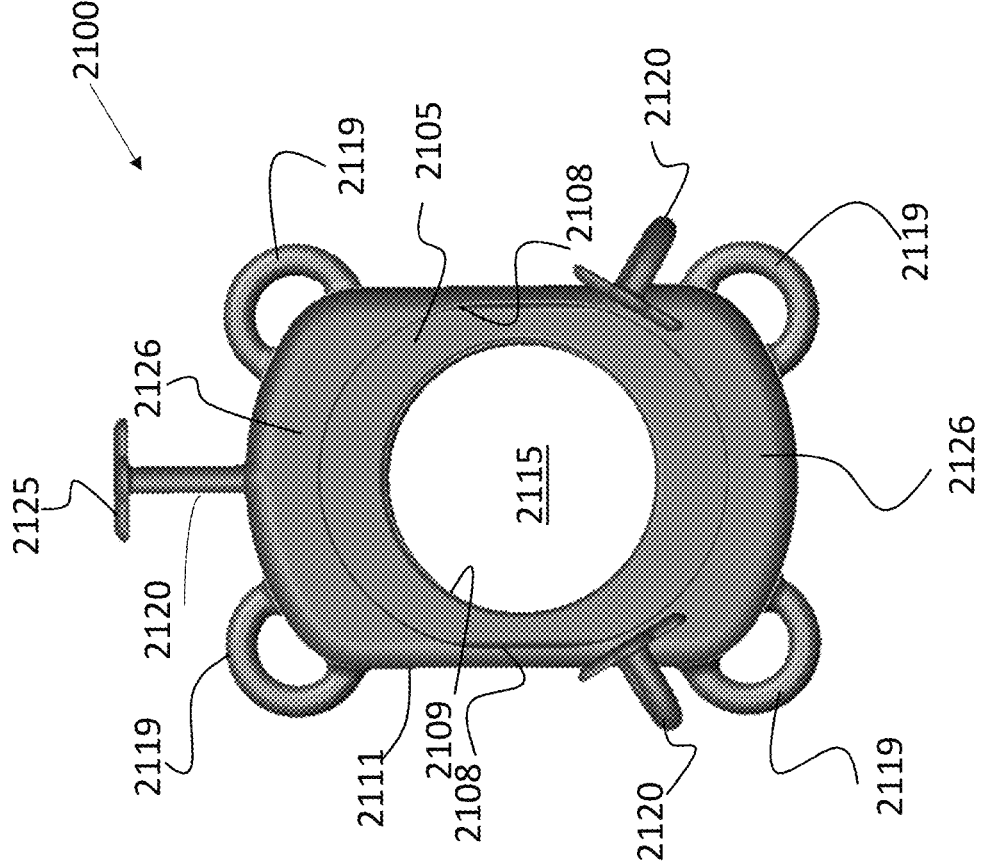
FIG. 27 shows another implementation of a device having awnings configured to accommodate an IOL.

FIG. 27 shows an interrelated implementation of a device 2100 having awnings 2126 that additionally incorporate a plurality of bumpers 2119 to assist in the centration of the device 2100 within the eye. The device 2100 can include four bumpers 2119 projecting outward from each corner of the lens support structure 2105. The bumpers 2119 can be substantially ring-shaped or incomplete rings having a C-shape. The ring-shaped bumper 2119 can include a first end and a second end that are both coupled to the lens support structure 2105. The C-shaped bumper 2119 can have one end coupled to the lens support structure 2105 and the second end that remains separated from the lens support structure 2105. Regardless, the shape or configuration, the bumper 2119 can urge the device 2100 away from the adjacent eye tissue. In some implementations, the bumper 2119 can deform slightly upon coming into contact with a ciliary structure. The deformation can be temporary so that the bumpers return to their original shape urging the device 2100 back towards a centralized position within the eye. As with other implementations described herein, the device 2100 can include a plurality of fixation arms 2120 including at least one that is biased into a folded configuration. Preferably, the bumpers 2119 avoid remaining in contact with the ciliary structures once the device 2100 is implanted. The bumpers 2119 can act as a guide during externalization of the fixation arms 2120. The bumpers 2119 can project sufficiently away from the outer perimeter 2111 of the lens support structure 2105 such that they abut against the ciliary body 15 and/or within the ciliary sulcus 25 to prevent displacement within the Z-plane to maintain proper alignment between the central aperture 2115 and the eye's visual axis during fixation.

A needle or guide wire (with or without suture) can be molded to the terminal footplate or anchor 125 such that the fixation arms 120 can be externalized from within the eye. The needle or guide wire, as applicable, can be externalized in precise locations prior to inserting the body of the device 100 into the eye. Once the surgeon is satisfied with the location of the needle or guide wire, the device 100 can be inserted into the eye, and each fixation arm 120 fixed in place with the appropriate procedures to ensure centration and z-axis location. Once the device 100 is properly fixed, the surgeon can trim the suture and/or needle from the device 100 leaving the anchor 125 in place. Alternatively, a modified sharp tipped forceps/grasper can be inserted through the main corneal wound (used for insertion of the lens fixation device) and then used to engage a fixation arm 120 and externalized. This would allow for a single pass to both create the sclerotomy and externalize the fixation arm anchor 125.

The device 100 can be inserted through a corneal or scleral incision using forceps or other common ophthalmic instruments. Alternatively, the device 100 can be inserted using an injector system similar to an intraocular lens injector. The injector allows the device 100 to unfurl in a manner that presents the fixation arms 120 sequentially to the surgeon. Alternatively, the injector can present the full device 100 into the anterior or posterior chamber in a configuration that limits the risk of surgical error. For instance, the injector can ensure that the device 100 is inserted "right side up." Additionally, the injector can limit the risk of iris 10, endothelial, capsular, or zonular damage during implantation.

The devices 100 described herein provide a stable platform and act as an artificial anterior aspect of the capsular bag for placement of an IOL 110. Reliable centration and axial position of the lens support structure 105 are important for optimal function of the device 100. In some implementations, a guide system can be used to align sclerotomy sites. The guide system can employ features similar to an intraoperative toric marker and pre-operative toric bubble marker. In addition to marking the correct meridional locations, the marker can assist in aligning the incisions relative to the limbus. An acceptable location for the sclerotomy can include posterior to the limbus and anterior to the ora serrota. In a human eye, the sclerotomy can be placed roughly about 0.1 mm to about 4 mm posterior to the limbus. By varying anterior/posterior sclerotomy sites with respect to limbus between about 0.1 mm and about 4 mm (z axis) or about 1.5 mm and about 4 mm, fixation arm tension can be controlled within an acceptable range. With varying diameters of marker/device pairs, the optimal size and location for the device 100 can be determined with the guide/marking system. FIGS. 14A-14B and FIGS. 15A-15I illustrate example sclerotomy guide tools 1000 incorporating a plurality of marking features 1005 that can be used to assist in the identification and marking of sclerotomy sites for insertion of the fixation arms 120 of the device 100. The tool 1000 may incorporate three marking features 1005 projecting from a distal end region 1015 of a handle 1010. The handle 1010 can extending along a first axis A and the distal end region 1015 can angle away from the first axis A. The marking features 1005 can project distal to the angled distal end region 1015 such that the features 1005 are off-set from the first axis A. The distal end region 1015 of the tool 1000 can form a tri-pod 1020 with the features 1005 projection from each prong 1025 of the tri-pod 1020 (see FIG. 14A). The distal end region 1015 of the tool 1000 can include a ring 1030 and the marking features 1005 project from a distal-facing surface of the ring 1030 (see FIG. 14B). The ring 1030 can provide a centering function. A surgeon can use the limbus, pupil, or white-to-white as a reference. The marking features 1005 can create at least three points of contact to define the location of the sclerotomies. The points of contact of the tool 1000 provided by the marking features 1005 can correspond to the number of sclerotomies desired for fixation of the device 100.

Each marking feature 10005 can project a distance outward from the ring 1030 (or tri-pod 1020) as well as a distance distal. FIGS. 15A-15D show an implementation of a tool 1000 that incorporates a larger standoff from the marking features 1005 relative to the ring 1030 compared to the embodiment shown in FIGS. 14A-14B. The marking features 1005 can have a length between their origin at the ring 1030 and the distal-most tip 1035 that provides a standoff of between about 1 mm to about 10 mm or about 3 mm to about 6 mm. The tool 1000 avoids interacting with ophthalmic instruments such as speculums, trocars, or other instruments that may be on the surface of the eye during surgery. In some implementations, the ring 1030 can additionally incorporate cross-hairs 1040 for centering (see FIGS. 15H-15I). The distance between the distal-most tip 1035 of each marking feature 1005 and the ring 1030 provides a sufficiently tall standoff to prevent the ring 1030 (or cross-hairs 1040, if present) from contacting the cornea during use (see FIGS. 15E-15G).

Figure 14A:
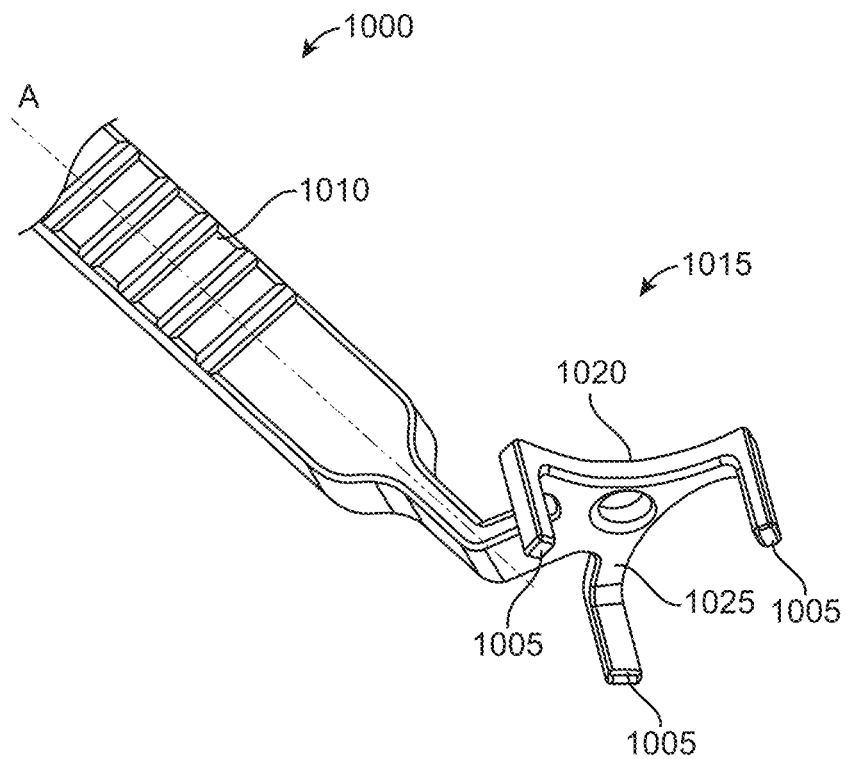
FIGS. 14A-14B shows different implementations of sclerotomy guide tools that can be used to assist in the identification and marking of sclerotomy sites.
Figure 14B:
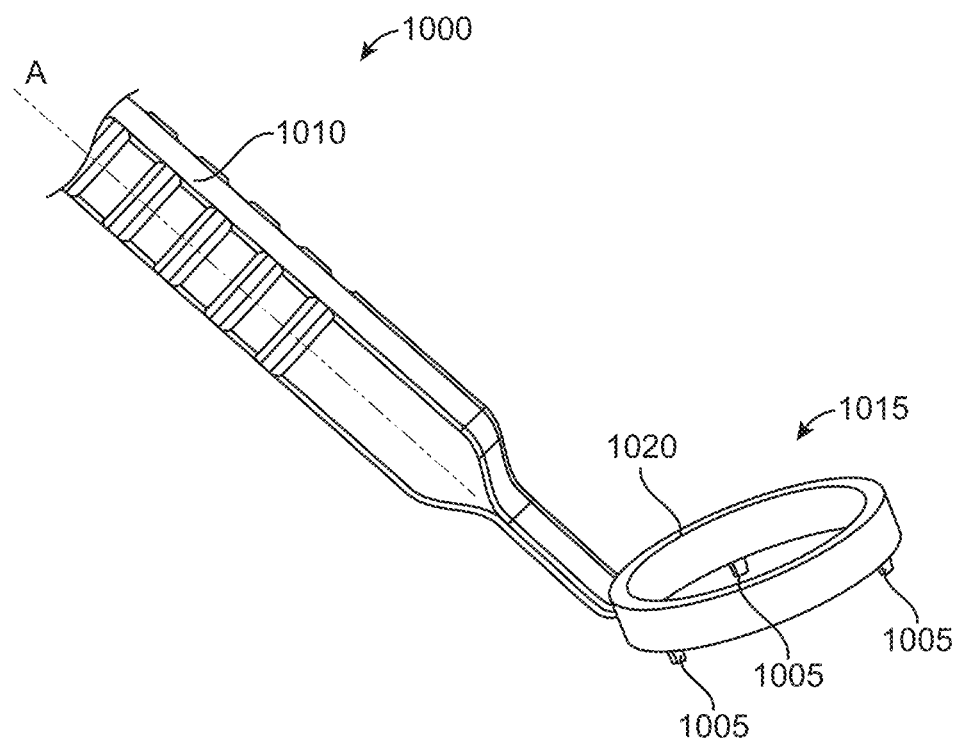
Figure 15A:
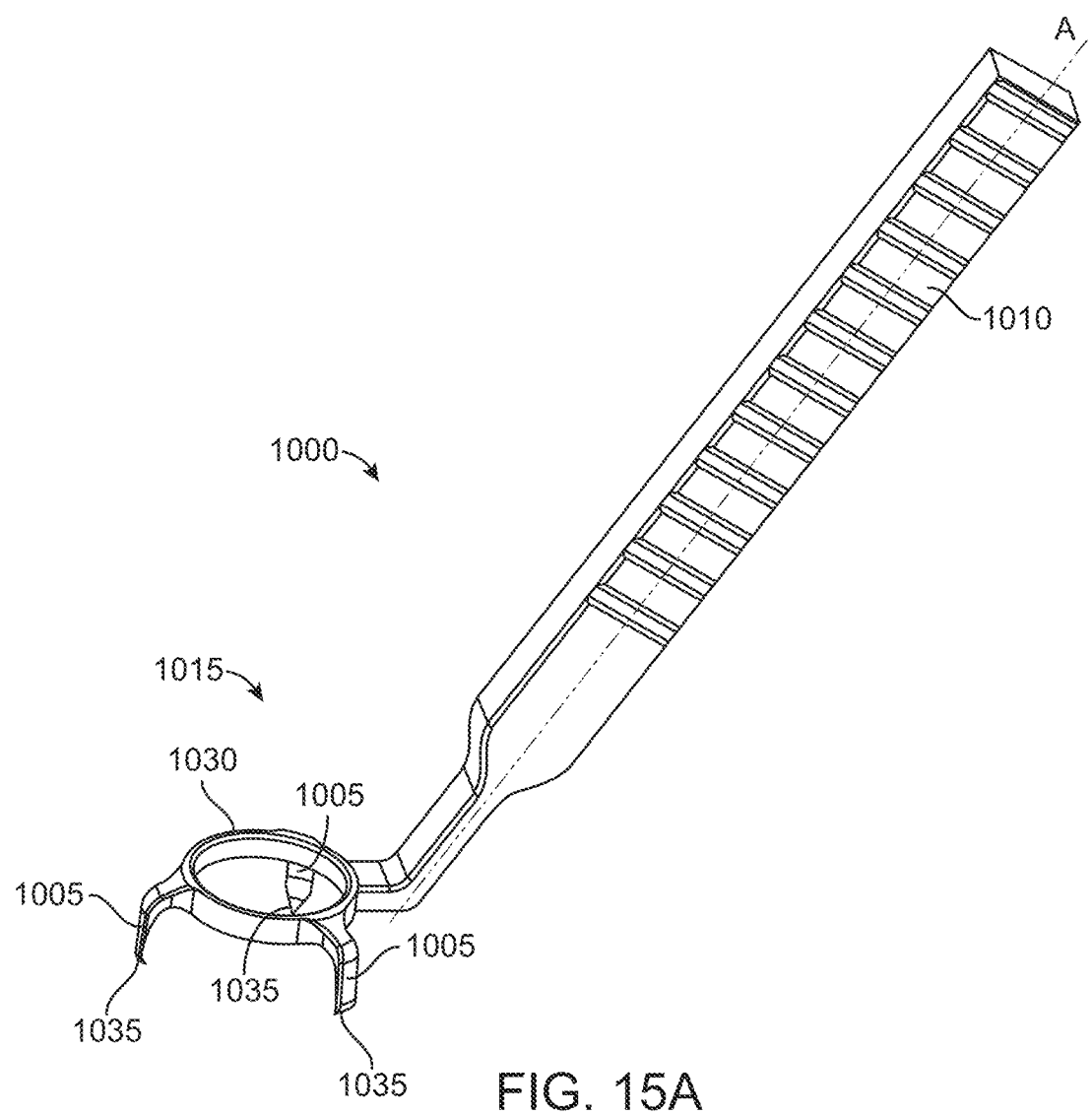
FIGS. 15A-15D show various views of another implementation of a sclerotomy guide tool.
Figure 15B:
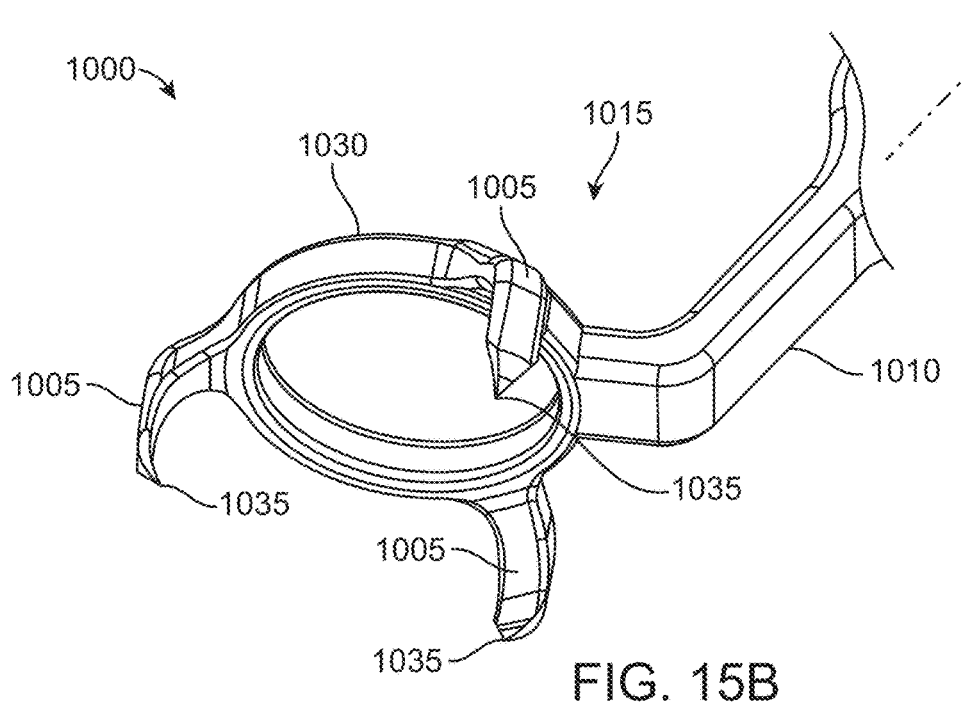
Figure 15C:
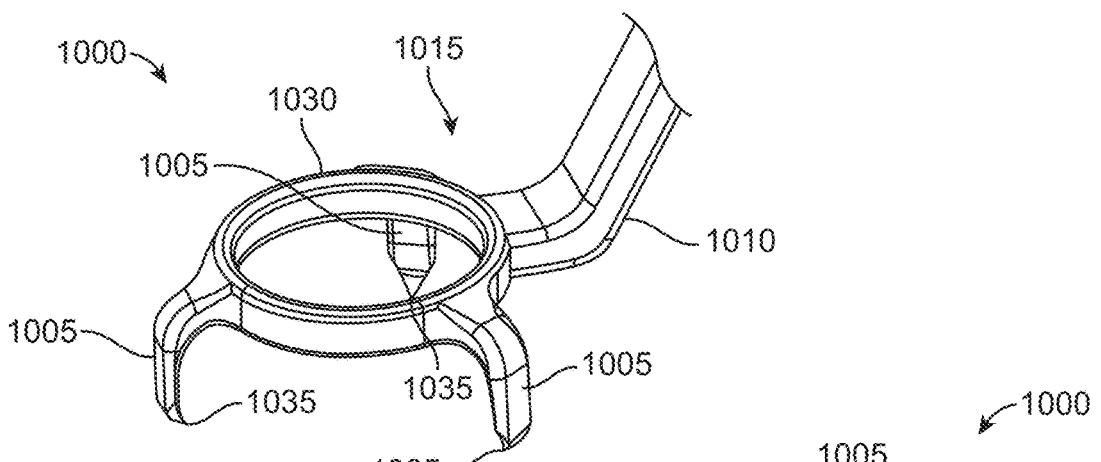
Figure 15D:
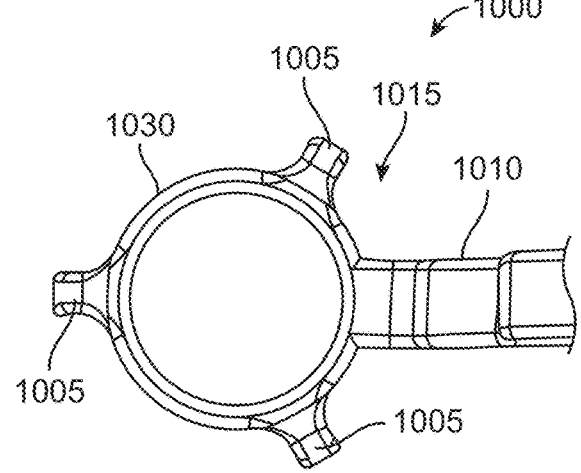
Figure 15G:
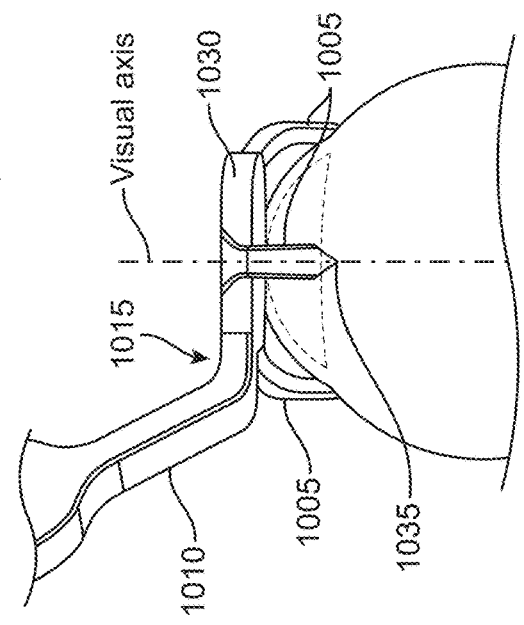
FIGS. 15E-15G show the sclerotomy guide tool of FIGS. 15A-15D positioned over a cornea.
Figure 15E:
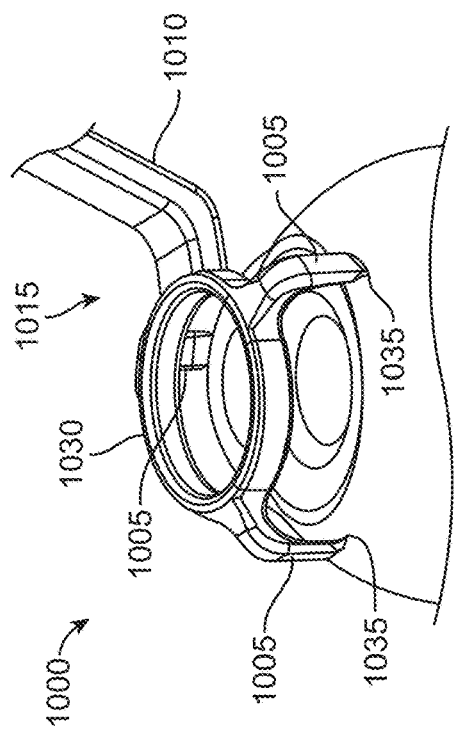
Figure 15F:
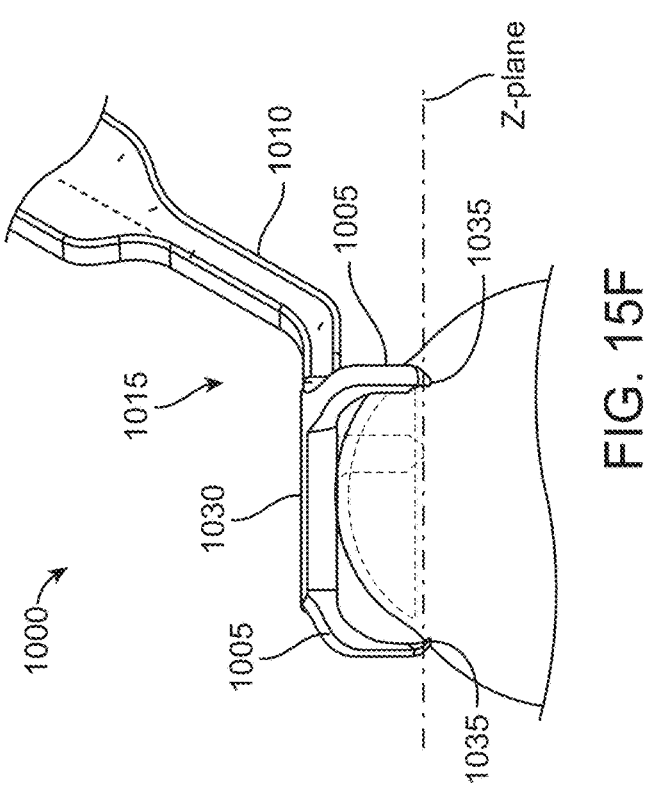
Figure 15H:
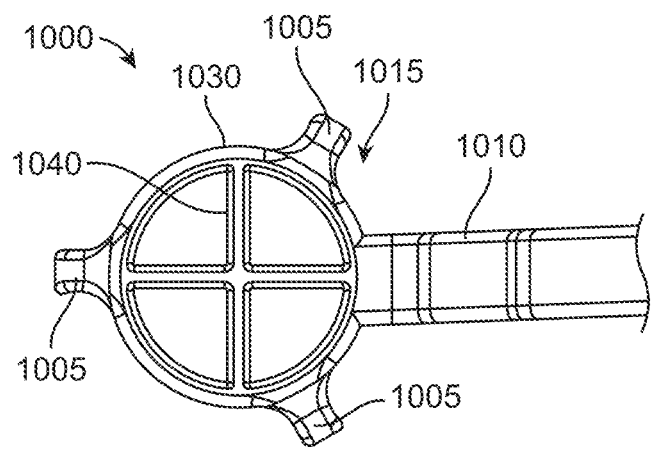
FIGS. 15H-15I show the sclerotomy guide tool of FIGS. 15A-15D having cross-hairs.
Figure 15I:
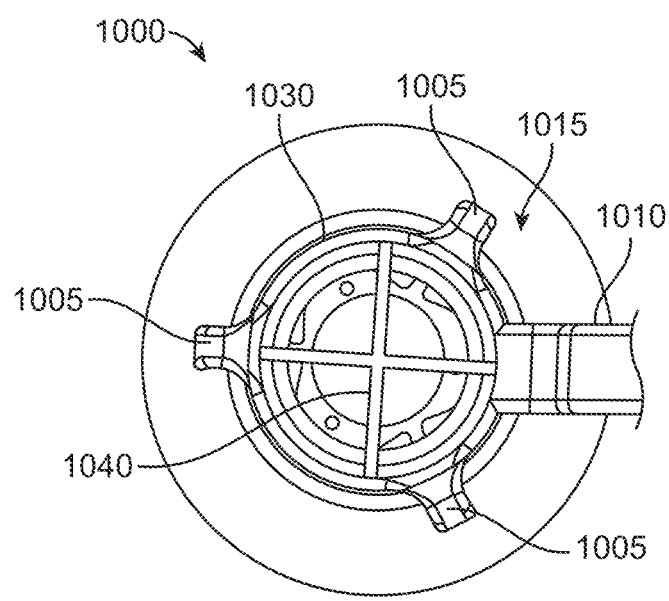
Figure 16A:
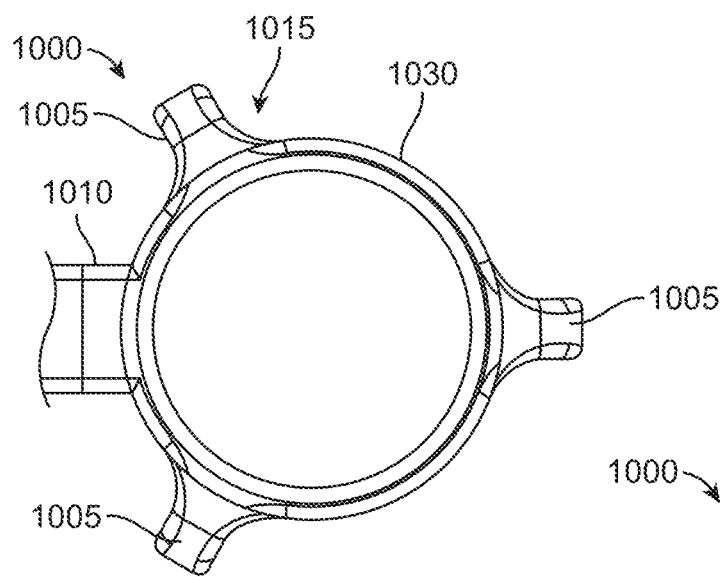
FIGS. 16A-16D show additional views of the sclerotomy guide tool of FIGS. 15A-15D.
Figure 16B:
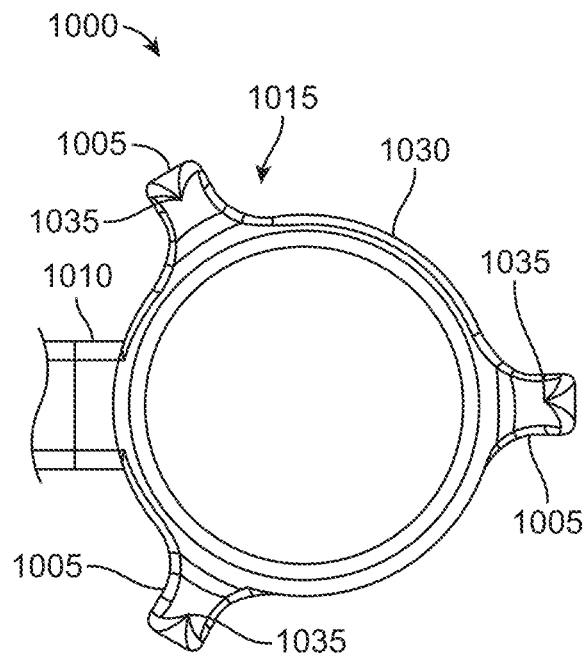
Figure 16C:
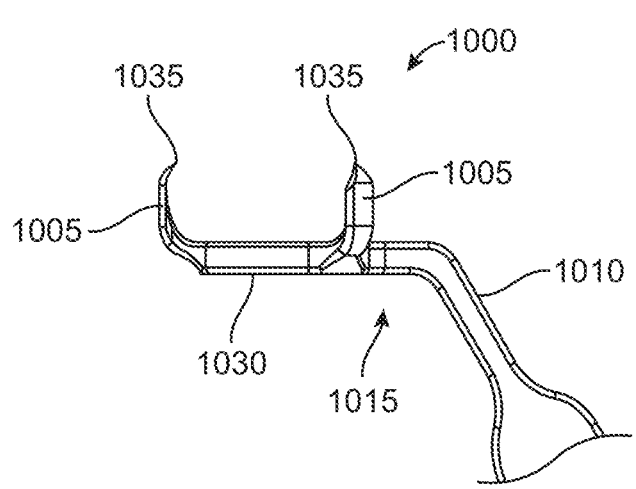
Figure 16D:
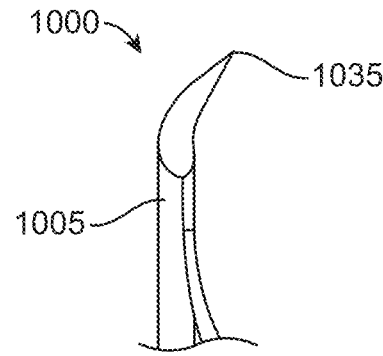

The inner diameter of ring 1030 can be between about 5 mm to about 15 mm (see FIG. 16A). The overall diameter defined by the distal-most tips 1035 of the tool 1000 can be between about 11 mm to about 18 mm, or between about 13 mm to about 17 mm (see FIG. 16B). The marking features 1005 can be distributed symmetrically around the circumference of the ring 1030. For example, if there are three marking features 1005, each one can be positioned around the circumference approximately 120 degrees from one another. Each marking feature 1005 can incorporate a bevel or double bevel leading to the distal-most tip 1035 such that the distal-most tip 1035 forms a generally sharpened point suitable for marking the sclera such as by creating an indentation (see FIG. 16A-16D). The bevel to create the point of the distal-most tip 1035 can extend a length that is about 0.15 mm to about 1.5 mm. The distal-most tip 1035 can angle inward towards a center of the ring 1030 such that the distal-most tip 1035 is off-set from the outermost extent of the marking feature 1005 (see FIG. 16D). The off-set of the tip 1035 relative to the outermost extent of the marking feature 1005 can be a distance from the outermost extent that is between about 0.15 mm to about 1.5 mm. Each marking feature 1005 can have a length that is between about 3 mm and about 10 mm and the beveled portion leading to the distal-most tip 1035 can be between 0.15 mm to about 1.5 mm of this length. The tips 1035 need not be sharpened to provide the marking function to the sclera. The tips 1035 can be blunt as shown in FIGS. 14A-14B and still be used to mark the sclera. The tips 1035, whether blunt or sharpened, can be used to mark the sclera mechanically by creating a plurality of indentations or by applying a separate visual marker to the sclera. For example, the lower end of each tip 1035 can be used to transfer an amount of ink or other visually suitable material transferrable to the sclera from the tip 1035.

Figure 17C:
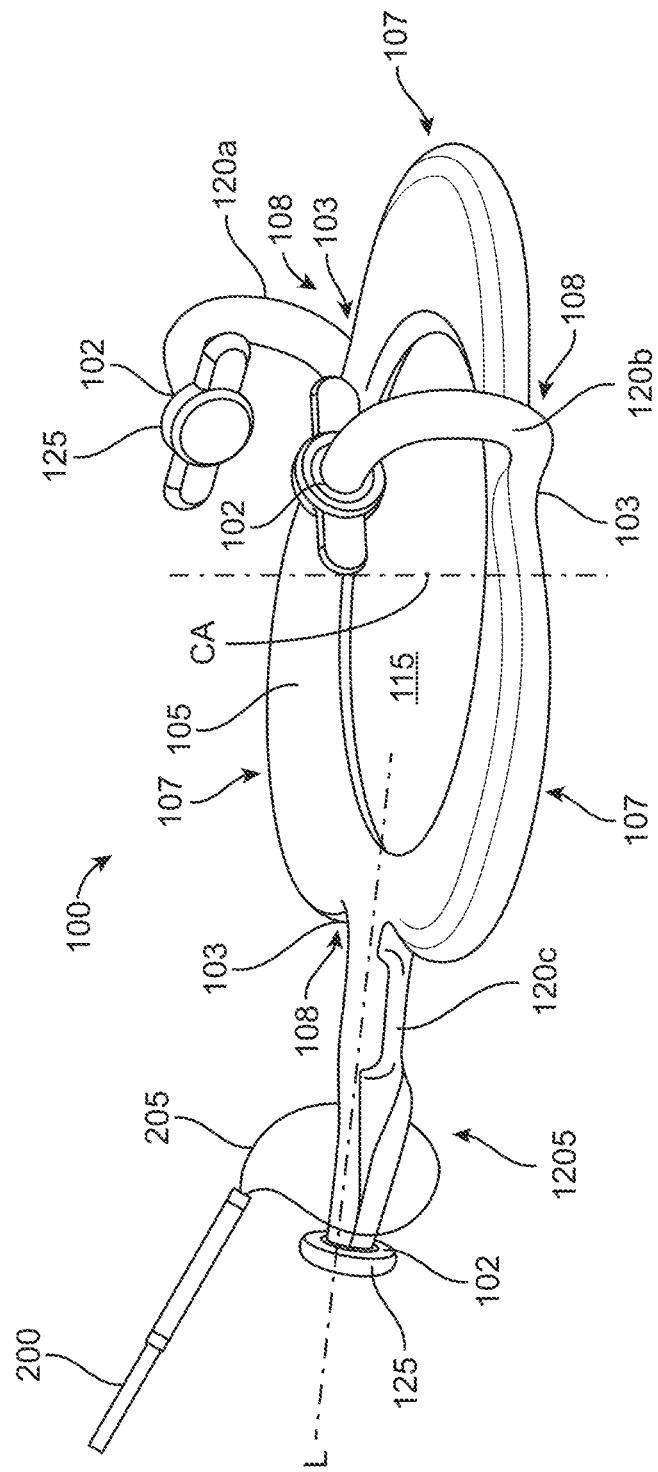
FIGS. 17C-17D shows a snare device looped around the leading fixation arm and used to externalize the anchoring footplates.
Figure 17D:
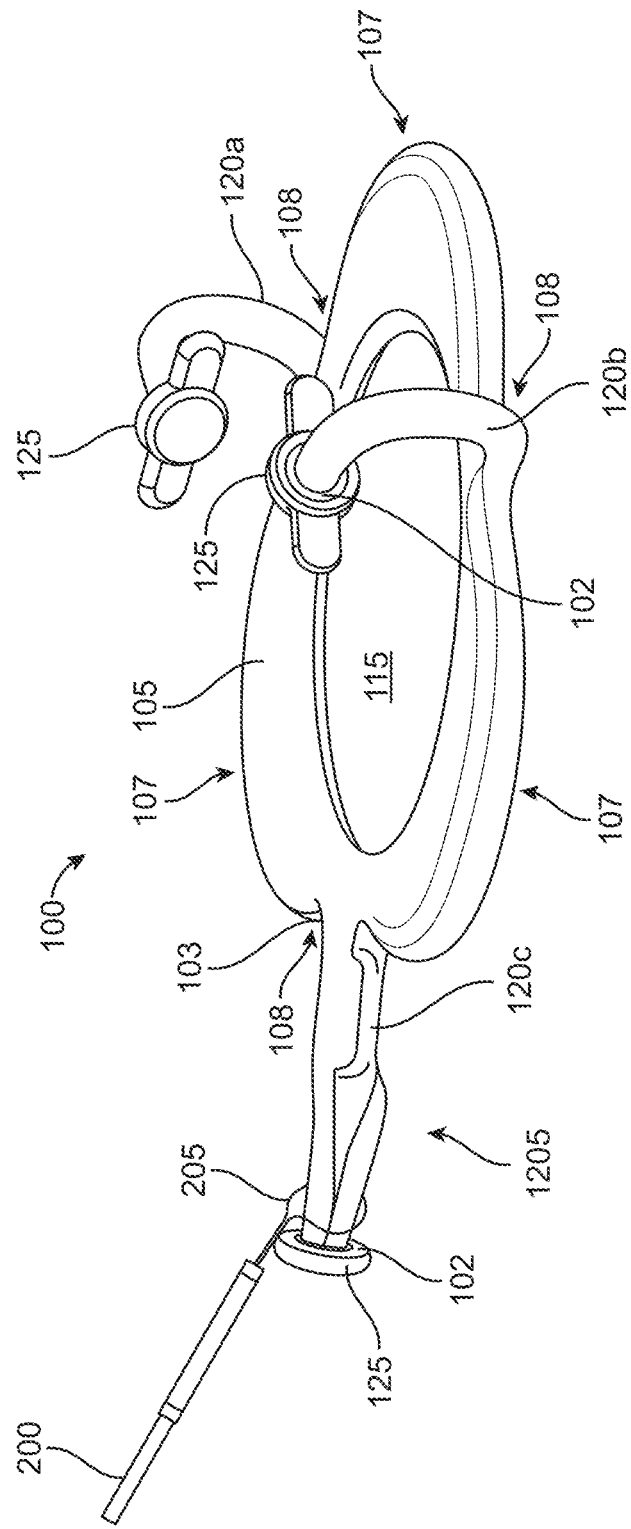
Figure 17E:
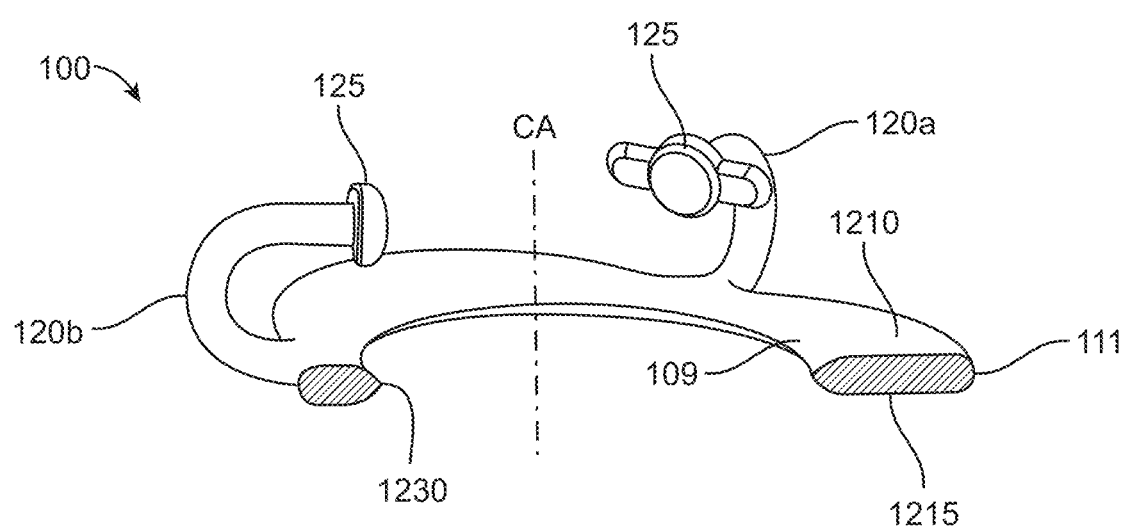
FIG. 17E shows a cross-sectional view of the device of FIG. 17D.

The anchor 125 externalization can be performed using standard tools used in ophthalmology. FIGS. 17C-17D illustrate a snare device 200 for externalization of the anchors 125. As discussed elsewhere herein, the footplates or anchors 125 are designed to be externalized through a sclerotomy (e.g., 23, 25, or 27 gauge sclerotomy). The snare device 200 can be designed to grasp and release the anchors 125 and/or fixation arms 120 of the device in order to fix them trans-sclerally. The snare device 200 can include an adjustable loop 205 configured to be enlarged and collapsed in size. The loop 205 can be passed over a portion of or the complete anchor 125. The loop 205 can be tightened such that the open are of the loop 205 decreases to firmly engage with the anchor and/or fixation arm. The surgeon can use the device 200 having the minimized loop 205 encircling the fixation arm/anchor to externalize the anchor 125 with minimal risk of losing grip on the anchor 125. Upon externalization of the anchor 125, the loop 205 can be at least partially reopened to enlarge the open area of the loop 205 to release the anchor 125. In the fully or partially opened configuration, the loop 205 can have an internal circumference of about 1.5 mm to about 10.0 mm. In the closed capture configuration, the internal circumference of the loop 205 can be about 0.25 mm to about 2.5 mm. The snare device 200 can be designed so that the loop can atraumatically grip the anchor 125 and/or fixation arm 120 so as not to damage the device 100. For example, the snare device 200 can have no sharp corners. The material of the loop 205 can provide mechanical properties that allow the loop 205 to atraumatically capture the arm 120 and repeatedly transition between a large circumference configuration to a small circumference configuration and back again to a large circumference configuration. The material of the loop 205 can provide tight grip with an atraumatic interaction with the fixation arm 120 or anchor 125. The loop 205 while gripping the fixation arm 120 or anchor 125 can deform to a significant degree during the externalization process. At least a portion of the snare device 200 can be bent. For example, the snare device 200 can be manufactured to have a bend near a distal end region or bent manually by a user at the time of use to suit ergonomic needs.

The loop 205 can be a wire-like structure with a full radius of curvature. The wire-like structure can be a rigid material such as stainless steel, titanium, Nitinol, or other metal. Alternatively the wire-like structure can be constructed from a plastic such as polypropylene, polyethylene, Nylon, Gortex, polyimide, PMMA, or other plastic. Alternatively, the wire-like structure of the loop 205 can be made from an elastomeric material such as flexible acrylics, polyurethane, silicone, SIBS, or other elastomeric polymers of similar mechanical properties.

The snare device 200 can also be configured to make the sclerotomy and/or function as an IOL grasper. FIGS. 18A-18D show implementations of snare devices 200. The loop 205 or other snare feature can extending from an inner lumen of the device. The opening from the inner lumen can be at the distal end as shown in FIGS. 17C-17D. The opening from the inner lumen can also be located proximal to the distal end through a side wall of the device as shown in FIGS. 18A-18B or swaged such that the sharpened tip extends distal to the orifice through which the loop 205 exits the lumen as shown in FIGS. 18C-18D. The device may have additional features to protect the snare material and the device from being damaged by the sharp edge of the distal tip 210. For example, the sharp distal tip 210 of the needle may be covered by a sheath or other element having a lumen and that is configured to be extended beyond the distal tip 210. This outer sheath can provide an atraumatic surface against which the loop 205 can be cinched. Alternatively, the puncturing tip 210 can be located a distance from the opening 215 through which the loop 205 is operated, for example, between about 0.2 mm to 10 mm away from the opening 215. The device 200 can incorporate a distal tip 210 suitable for making the sclerotomy. The distal tip 210 can have a variety of geometries such as a non-coring trocar tip as shown in FIGS. 18A-18B or a back bevel needle cannula tip as shown in FIGS. 18C-18D. The geometry of the distal tip 210 can include, but is not limited to a bevel, tri-facet trocar, conical, diamond, pencil point, swaged, skived, or other pointed geometry.

In still further implementations, the anchor 125 can be externalized using a forceps type device. The forceps can be straight or angled. The forceps device can enhance the surgeon's grip by incorporating a locking feature. The forceps device for externalization can transition from a locked to an unlocked and vice versa via any of variety of mechanical motions including twisting, squeezing, sliding, mechanisms that reduce the range of motion of the forceps once engaged. In some implementations, the locking forceps has two grasping faces that are locked in a restricted conformation. In other implementations, the forceps has three or four grasping faces that can be locked into a restricted conformation. The locked or restricted conformation may also encase the anchor 125 within a sheath that assists in the externalization procedure. Fully encasing the anchor 125 can limit interference between the anchor and the sclera as it inserts through the wound. The sheath can define an outermost surface during externalization that can be designed to optimally interact with the ocular tissue. For example, the outermost surface of the sheath can have a profile that is rounded (e.g., circular, elliptical, ovoid, etc.) The sheath may also have a coating to reduce friction with the tissue during externalization. The sheath can be sufficiently rigid so as to substantially retain its shape during externalization.

The devices described herein may be implanted into the posterior chamber of an eye lacking an intact capsular bag. As described elsewhere herein, prior to insertion into the posterior chamber, at least one of the at least three fixation arms can be biased towards a linear configuration and at least a second of the at least three fixation arms can be biased towards a folded configuration. The folded configuration includes the origin portion of the fixation arm extending away from the lens support structure, a central portion of the fixation arm having a bend, fold, or curve so that the anchor of the terminal end portion can be then positioned over or under at least one of a portion of the lens support structure and a portion of the central opening. Once the device inserted into the posterior chamber, at least a portion of the fixation arm in the folded configuration can be visualized through the pupil. The anchor of the straight fixation arm can be grasped and externalized through and over a first portion of the sclera. The anchor of a curved fixation arm can be grasped, unfolded, and externalized through and over a second portion of the sclera. A third of the fixation arms can then be grasped, tensioned, and externalized through and over a third portion of the sclera to locate and stabilize the device within the posterior chamber of the eye.

Suitable materials or combinations of materials for the preparation of the various components of the devices disclosed herein are provided throughout. It should be appreciated that other suitable materials are considered. The device 100 can be constructed from any implant grade material that can provide the functions required of the lens support structure 105, fixation arms 120, and anchors 125. Materials that may be employed in this device could be but are not limited to silicone elastomer, fluorosilicone elastomer, polyurethane, hydrophilic or hydrophobic acrylics, polyolefins, nylons, PVDF, PMMA, polyimide, nitinol, titanium, stainless steel, or other implant grade materials. The device may be made from a combination of materials that are geometrically mated together, chemically bonded or welded to one another, overmolded, encapsulated, or other means for joining multiple materials. A given device element may be made of multiple materials. The fixation arms 120 may be constructed from an inelastic or semi-rigid material common to ophthalmic applications such as polypropylene, Nylon, PVDF, polyimide, PMMA, polyurethane, hydrophilic or hydrophobic acrylics, or high durometer silicones. The fixation arms 120 can incorporate or be formed of elastic materials such as acrylics, polyurethanes, silicone elastomers or copolymers thereof that facilitate manipulation of the fixation arm 120 during implantation. In still further implementations, the fixation arm 120 can be formed of a semi-rigid or rigid plastic material such as polypropylene, Nylon, PVDF, polyimide, PMMA, polyurethane, hydrophilic or hydrophobic acrylics, or high durometer silicones embedded or coated with a soft, elastomeric material such as acrylics, polyurethanes, silicone elastomers or copolymers thereof.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detain in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various placed throughout this specification are not necessarily referring to the same embodiment or implementation. Furthermore, the particular features, structures, configurations, or characteristics may be combined in any suitable manner in one or more implementations.

The devices and systems described herein can incorporate any of a variety of features. Elements or features of one implementation of a device and system described herein can be incorporated alternatively or in combination with elements or features of another implementation of a device and system described herein. For the sake of brevity, explicit descriptions of each of those combinations may be omitted although the various combinations are to be considered herein. Additionally, the devices and systems described herein can be positioned in the eye and need not be implanted specifically as shown in the figures or as described herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

The use of relative terms throughout the description may denote a relative position or direction or orientation and is not intended to be limiting. For example, "distal" may indicate a first direction away from a reference point. Similarly, "proximal" may indicate a location in a second direction opposite to the first direction. Use of the terms "upper," "lower," "top", "bottom," "front," "side," and "back" as well as "anterior," "posterior," "caudal," "cephalad" and the like or used to establish relative frames of reference, and are not intended to limit the use or orientation of any of the devices described herein in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together."

A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A method for preparing to support an artificial intraocular lens in an eye, the method comprising:
    inserting a device into a position behind an iris of the eye, wherein said device comprises:
        a lens support structure comprising an inner perimeter surface defining, at least in part, a central opening, wherein, when the device is implanted in the eye, light may pass through the central opening towards the retina; and
        at least three fixation arms, wherein each of the at least three fixation arms comprises an origin portion coupled to the lens support structure and a terminal portion comprising an anchor;
        wherein, after said inserting, the device comprises at least one fixation arm of the at least three fixation arms in a folded configuration, wherein said at least one fixation arm is flexible and is biased towards said folded configuration, and wherein said anchor of said at least one fixation arm is both visible by a user through a pupil of said eye and is positioned adjacent to, over, or under a portion of the lens support structure and/or a portion of the central opening;
    grasping at least a portion of said at least one fixation arm to unfurl said at least one fixation arm; and
    securing said anchor of said at least one fixation arm to a sclera of the eye.

2. The method of claim 1, wherein the at least a portion grasped is the at least one fixation arm between the origin portion and the terminal portion.

3. The method of claim 1, wherein the at least a portion grasped is the anchor.

4. The method of claim 1, wherein the anchor of the at least one fixation arm in the folded configuration, when the device is inserted behind the iris and before securing the anchor, is positioned over and anterior to the portion of the lens support structure relative to the retina, or is positioned over and anterior to the portion of the central opening relative to the retina, or wherein at least a first portion of the anchor is over and anterior to the portion of the central opening and at least a second portion of the anchor is over and anterior to the portion of the lens support structure relative to the retina.

5. The method of claim 1, wherein the anchor of the at least one fixation arm in the folded configuration, when the device is inserted behind the iris and before securing the anchor, is positioned under and posterior to the portion of the lens support structure relative to the retina or is positioned under and posterior to the portion of the central opening relative to the retina, or wherein at least a first portion of the anchor of the at least one fixation arm in the folded configuration is under and posterior to the portion of the central opening and at least a second portion of the anchor of the at least one fixation arm in the folded configuration is under and posterior to the portion of the lens support structure relative to the retina.

6. The method of claim 1, wherein the folded configuration comprises the terminal portion of the at least one fixation arm folded over or under the origin portion of the at least one fixation arm.

7. The method of claim 1, wherein the anchor of the at least one fixation arm in the folded configuration is positioned within a distance from a central axis of the device, the central axis extending anterior-to-posterior through the central opening, wherein the distance is no greater than about 4.0 mm.

8. The method of claim 1, wherein the at least one fixation arm in the folded configuration curves such that the anchor of the terminal portion of the at least one fixation arm projects back towards the central opening of the device.

9. The method of claim 1, where the anchor of the at least one fixation arm is adapted for sutureless scleral fixation.

10. The method of claim 1, wherein the lens support structure further comprises an outer perimeter, wherein the outer perimeter of the lens support structure is non-circular, and wherein the inner perimeter surface is circular.

11. The method of claim 1, wherein the lens support structure further comprises an outer perimeter, and wherein the outer perimeter comprises a plurality of lobes projecting radially away from the central opening.

12. The method of claim 1, wherein at least a second fixation arm of the at least three fixation arms is biased towards the folded configuration when the device is implanted behind the iris and before the anchor of the at least a second fixation arm is secured.

13. The method of claim 1, wherein at least one other fixation arm of the at least three fixation arms is biased towards an unfolded configuration at rest prior to insertion behind the iris and before the anchor of the at least one other fixation arm is secured.

14. The method of claim 13, wherein the at least one other fixation arm of the at least three fixation arms has a larger cross-sectional area compared to a cross-sectional area of the at least one fixation arm in the folded configuration to provide an increased rigidity of the at least one other fixation arm relative to a rigidity of the at least one fixation arm of the at least three fixation arms.

15. The method of claim 1, wherein the lens support structure comprises a geometry adapted to mate with a perimeter of an intraocular lens or with one or more haptics of the intraocular lens.

16. The method of claim 15, wherein the geometry comprises a concavity, recess, channel, or groove for mating with the perimeter of the intraocular lens or with the one or more haptics of the intraocular lens.

17. The method of claim 1, wherein the flexibility of the at least one fixation arm of the at least three fixation arms facilitates unfurling of the at least one fixation arm from the folded configuration to an unfolded configuration in order to facilitate securing the anchor.

18. The method of claim 1, wherein the device comprises three fixation arms,
 wherein, after inserting the device into the position behind the iris and before securing the anchor, two of the three fixation arms are in a folded configuration, flexible, and are biased towards the folded configuration, and
 wherein a third fixation arm is less flexible than the two of the three fixation arms, and is biased towards an unfolded configuration.

19. The method of claim 1, further comprising positioning the artificial intraocular lens in the eye and against the lens support structure of the device, the artificial intraocular lens comprising a central optic and one or more haptics.

20. The method of claim 19, wherein positioning comprises passing the central optic of the artificial intraocular lens through the central opening to a posterior side of the lens support structure while the one or more haptics of the artificial intraocular lens remain anterior to the lens support structure.

21. The method of claim 19, wherein the device further comprises one or more awnings positioned over an anterior-facing surface forming one or more recesses at least partially surrounding the central opening.

22. The method of claim 21, wherein positioning the artificial intraocular lens against the lens support structure further comprises positioning at least a portion the artificial intraocular lens within the one or more recesses.

23. The method of claim 19, wherein positioning the artificial intraocular lens against the lens support structure allows for the artificial intraocular lens to be removed for lens replacement.

24. The method of claim 1, wherein securing said anchor comprises suturelessly securing said anchor external to the sclera, within the sclera, or internal to the conjunctiva.

25. The method of claim 1, further comprising forming at least one sclerotomy using a sclerotomy guide tool positioned over a cornea of the eye.

26. The method of claim 25, wherein the at least one sclerotomy is located about 0.1 mm to about 4 mm posterior to the limbus.

27. The method of claim 1, further comprising using a single tool to enter the eye through the sclera, grasp the at least one fixation arm or the anchor of the at least one fixation arm, and externalize the anchor through the sclera in a single pass with the single tool.

28. The method of claim 1, wherein securing the anchor comprises externalizing the anchor through a sclerotomy.

29. The method of claim 1, wherein grasping further comprises using a forceps-type device or a snare device to grasp the at least a portion of said at least one fixation arm.

30. The method of claim 1, further comprising grasping at least a portion of a second fixation arm of the at least three fixation arms and securing the anchor of the second fixation arm to the sclera, or at least a portion of a third fixation arm of the at least three fixation arms and securing the anchor of the third fixation arm to the sclera.

* * * * *